(12) United States Patent
Kerr et al.

(10) Patent No.: US 6,653,451 B1
(45) Date of Patent: *Nov. 25, 2003

(54) SOYBEAN PRODUCTS WITH IMPROVED CARBOHYDRATE COMPOSITION AND SOYBEAN PLANTS

(75) Inventors: Phillip Scott Kerr, Urbandale, IA (US); Scott Anthony Sebastian, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/642,337

(22) Filed: Aug. 21, 2000

Related U.S. Application Data

(60) Division of application No. 08/976,977, filed on Nov. 25, 1997, now Pat. No. 6,147,193, which is a division of application No. 08/382,313, filed on Jan. 31, 1995, now Pat. No. 5,710,365, which is a continuation-in-part of application No. 08/211,709, filed as application No. PCT/US92/08958 on Oct. 26, 1992, now abandoned, which is a continuation-in-part of application No. 07/782,033, filed on Oct. 24, 1991, now abandoned.

(51) Int. Cl.[7] .............................................. C07K 14/00
(52) U.S. Cl. ...................... 530/378; 426/629; 426/630; 426/658; 435/172.1
(58) Field of Search ........................... 530/378; 426/629

(56) References Cited

U.S. PATENT DOCUMENTS

| | | | |
|---|---|---|---|
| 3,903,645 A | | 9/1975 | Bradner ........................ 47/58 |
| 3,971,856 A | * | 7/1976 | Daftary ....................... 426/417 |
| 5,100,679 A | | 3/1992 | Delrue .......................... 426/44 |
| 5,710,365 A | * | 1/1998 | Kerr et al. ................... 800/200 |
| 5,858,449 A | | 1/1999 | Crank et al. ................ 426/656 |
| 5,936,069 A | | 8/1999 | Johnson ...................... 530/378 |
| 6,147,193 A | * | 11/2000 | Kerr et al. .................. 530/378 |

OTHER PUBLICATIONS

Lehl et al, *Methods in Enzymol.*, 28, 522–530 (1972).
Bernard et al, *Regional Soybean Lab. Manual*, 230, 1–3, 60–61 (Sep. 1966).
Snyder et al, *Soybean Utilization*, Van Nostrand Reinhold Comp., New York, Chap. 2, pp 58–59; Chap. 3, pp. 74–94 (1987).
Poehlman, *Breeding Fieldcrops*, Van Nostrand Reinhold Comp., New York, Chap. 17, pp. 421–450 (1986).
Y.P.S. Bajaj Ed., "Biotechnology in Agriculture and Forestry", vol. 2 Crops I., Springer Verlag, Berlin, Chap. II.1, pp. 283–308; Hildebrand et al: "Soybean (Glycine max(L.) Merr)".
Murphy et al, *J. Agr. Food Ceh.*, 20 813–817 (1972).
Cristofara et al, *Sugars in Nutrition*, H.L. Sipple & H.W. McNutt Eds., Academic Press, New York, Chap. 20, pp. 313–335 (1974).
Reddy et al, *J. Food Science*, 45, 1161–1164 (1980).
Dey, *Biochemistry of Storage Carbohydrates in Green Plants*, P.M. Dey & R.A. Dixon Eds., Academic Press, London, pp. 53–129 (1985).
Gitzelmann et al, *Pediatris*, 36, 231–236 (1965).
Rutloff et al, *Nahrung*, 11, 39–46 (1967).
Oil Crops Situation and Outlook report (Apr. 1989).
Soy Protein Products. Characteristics, Nutritional Aspects and Utilization 91987.
Potter et al, *Proceedings World Soybean Conference III*, pp. 218–224 (1984).
Coon et al, *Proceedings Soybean Utilization Alternatives*, Univ. of Minnesota, pp. 203–211 (1988).
Mustakas et al, *J. Amer. Oil Chemists Soc.*, 39, 222 (1962).
Smiley et al, *Applied and Environmental Microbiology*, 31, 615–617 (1976).
Rackis, *J. Amer. Oil Chemists Soc.*, 58, 503–509 (1981).
Hymowitz et al, *Comm. in Soil Science and Plant Analysis*, 3, 367–373 (1972).
Hymowitz et al, *Agronomy J.*, 64, 613–616 (1972).
Hymowitz et al, *Agronomy J.*, 66, 239–240 (1984).
Openshaw et al, *Crop Science*, 18, 581–584 (1978).
Openshaw et al, *Crop Science*, 21, 805–808 (1981).
Jacorzynski et al, *Acta Agrobotanica*, 36, 41–48 (1983).
Ovacharov et al, *Fiziol. Rast.*, 21, 969–974.
Caffrey et al, *Plant Physiol.*, 86, 754–758 (1988).
Schleppi et al, *Iowa Seed Science*, 11, 9–12 (1989).
Saravitz et al, *Plant Physiol.*, 83, 185–189 (1987).
Yasui, Takeshi, Dissimilarity in Low Molecular Weight Carbohydrate Composition of the Seeds of Cultivated Soybean.[*Glycine max* (L.) Merrill subsp. max] and Wild Soybean[*G. max* subsp. soja(Sieb et Zucc.) Ohashi], *Agric. Biol. Chem.*, 49 (4), 933–937, 1985.

* cited by examiner

Primary Examiner—Brenda Brumback
Assistant Examiner—Roy Teller

(57) ABSTRACT

There is provided soybean protein products of significantly lower stachyose content as a function of an improved soybean having a seed stachyose content of less than 50 μmol/g. Improved soybean lines are provided as are methods of using such reduced stachyose soybeans.

7 Claims, 3 Drawing Sheets

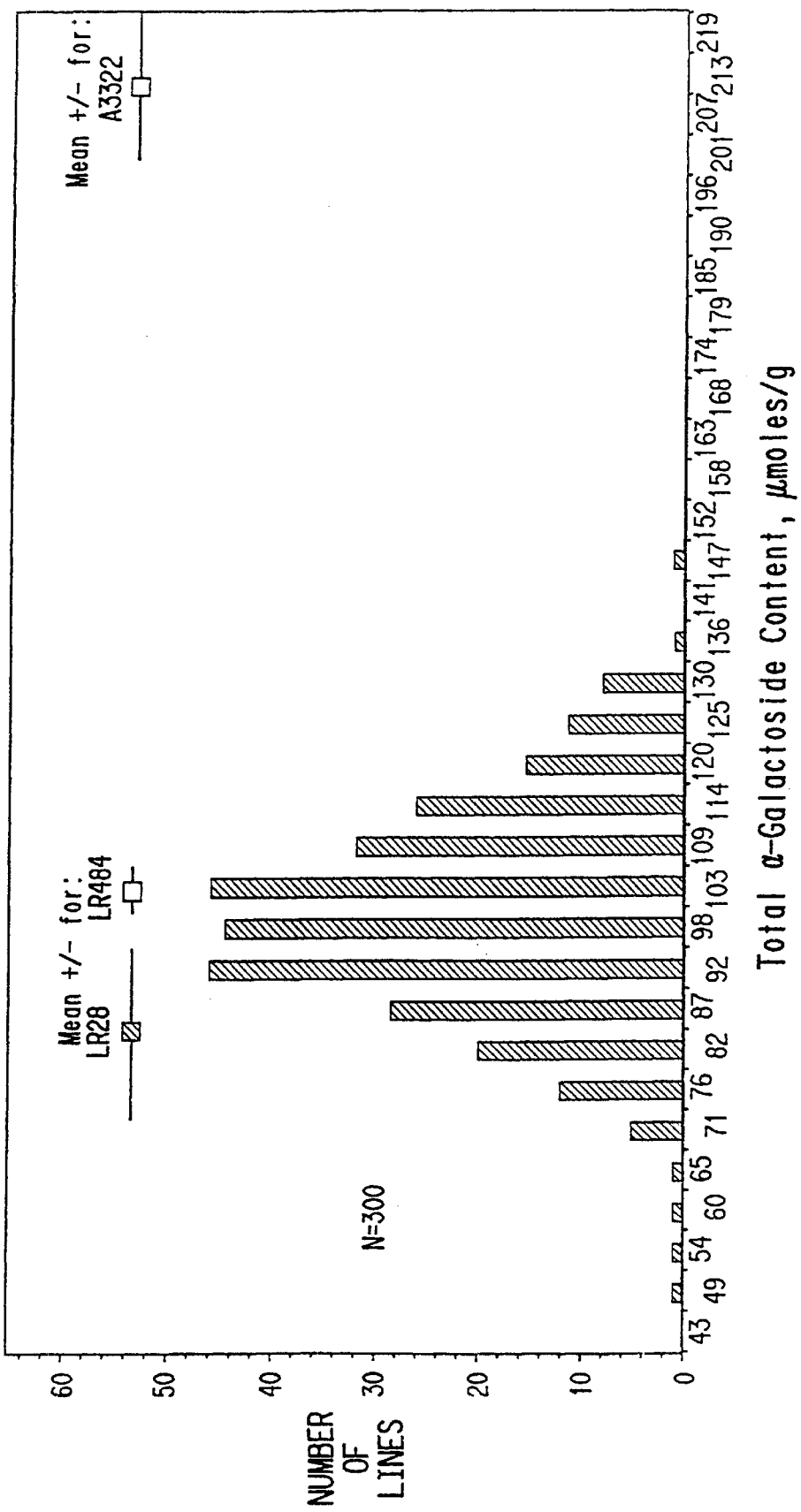

SOYBEAN PRODUCTS WITH IMPROVED CARBOHYDRATE COMPOSITION AND SOYBEAN PLANTS

This is a division of application Ser. No. 08/976,977 filed Nov. 25, 1997, now U.S. Pat. No. 6,147,193, which is a division of application Ser. No. 08/382,313, filed Jan. 31, 1995 granted as U.S. Pat. No. 5,710,365 on Jan. 20, 1998, which is a continuation-in-part of application Ser. No. 08/211,709 filed Apr. 21, 1994 now abandoned from PCT/US92/08958 filed Oct. 26, 1992, which is a continuation-in-part of application Ser. No. 07/782,033 filed Oct. 24, 1991, now abandoned.

FIELD OF THE INVENTION

This invention relates to soybean protein products having significantly lower stachyose content as a function of using the seeds of a soybean line having a heritable seed stachyose content of less than 50 $\mu$mol/g (dry seed basis). The present invention also relates to such low stachyose-containing soybeans.

BACKGROUND OF THE INVENTION

Raffinose saccharides are a group of D-galactose-containing oligosaccharides of sucrose that are widely distributed in plants. Raffinose saccharides are characterized by having the general formula: [O-$\beta$-D-galactopyranosyl-(1$\rightarrow$6)$_n$-$\alpha$-glucopyranosyl-(1$\rightarrow$2)-$\beta$-D-fructofuranoside where n=0 through n=4 are known respectively as sucrose, raffinose, stachyose, verbascose, and ajugose.

Extensive botanical surveys of the occurrence of raffinose saccharides have been reported in the scientific literature [see Dey, P. M. In *Biochemistry of Storage Carbohydrates in Green Plants,* Academic Press, London, (1985) pp 53–129]. Raffinose saccharides are thought to be second only to sucrose among the nonstructural carbohydrates with respect to abundance in the plant kingdom. In fact, raffinose saccharides may be ubiquitous, at least among higher plants. Raffinose saccharides accumulate in significant quantities in the edible portion of many economically significant crop species. Examples include soybean (*Glycine max* L. Merrill), sugar beet (*Beta vulgaris*), cotton (*Gossypium hirsutum* L.), canola (Brassica sp.) and all of the major edible leguminous crops including beans (Phaseolus sp.), chick pea (*Cicer arietinum*), cowpea (*Vigna unguiculata*), mung bean (*Vigna radiata*), peas (*Pisum sativum*), lentil (*Lens culinaris*) and lupine (Lupinus sp.).

The biosynthesis of raffinose saccharides has been fairly well characterized [see Dey, P. M. In *Biochemistry of Storage Carbohydrates in Green Plants* (1985)]. The committed reaction of raffinose saccharide biosynthesis involves the synthesis of galactinol (O-$\alpha$-D-galactopyranosyl-(1$\rightarrow$1)-myo-inositol) from UDP galactose and myo-inositol. The enzyme that catalyzes this reaction is galactinol synthase. Synthesis of raffinose and higher homologues in the raffinose saccharide family from sucrose is thought to be catalyzed by distinct galactosyltransferases (e.g., raffinose synthase, stachyose synthase, etc.).

Although abundant in many species, raffinose saccharides are an obstacle to the efficient utilization of some economically important crop species. Raffinose saccharides are not digested directly by animals, primarily because $\alpha$-galactosidase is not present in the intestinal mucosa [Gitzelmann and Auricchio *Pediatrics* (1965) 36:231–236, Rutloff et al *Nahrung* (1967) 11:39–46]. However, microflora in the lower gut are readily able to ferment the raffinose saccharides which results in an acidification of the gut and production of carbon dioxide, methane and hydrogen [Murphy et al. (1972) *J. Agr. Food Chem.* 20:813–817, Cristofaro et al. In *Sugars in Nutrition,* (1974) Chapter 20, 313–335, Reddy et al. *J. Food Science* (1980) 45:1161–1164). The resulting flatulence can severely limit the use of leguminous plants in animal, including human, diets. It is unfortunate that the presence of raffinose saccharides restricts the use of soybeans in animal, including human, diets because otherwise this species is an excellent source of protein and fiber.

The soybean is well-adapted to machinery and facilities for harvesting, storing and processing that are widely available in many parts of the world. In the U.S. alone, approximately 28 million metric tons of meal were produced in 1988 (*Oil Crops Situation and Outlook Report,* April 1989, U.S. Dept of Agriculture, Economic Research Service). Typically, hulls are removed and then the oil is extracted with hexane in one of several extraction systems. The remaining defatted flakes can then be used for a variety of commercial soy protein products [see *Soy Protein Products, Characteristics, Nutritional Aspects and Utilization* (1987) Soy Protein Council]. Foremost among these in volume of use is soybean meal, the principle source of protein in diets used for animal feed, especially those for monogastric animals such as poultry and swine.

Although the soybean is an excellent source of vegetable protein, there are inefficiencies associated with its use that appear to be due to the presence of raffinose saccharides. Compared to maize, the other primary ingredient in animal diets, gross energy utilization for soybean meal is low [see Potter and Potchanakorn In *Proceedings World Soybean Conference III,* (1984) 218–224]. For example, although soybean meal contains approximately 6% more gross energy than ground yellow corn, it has about 40 to 50% less metabolizable energy when fed to chickens. This inefficiency of gross energy utilization does not appear to be due to problems in digestion of the protein fraction of the meal, but rather due to the poor digestion of the carbohydrate portion of the meal. It has been reported that removal of raffinose saccharides from soybean meal by ethanol extraction results in a large increase in the metabolizable energy for broilers [Coon, C. N. et al. *Proceedings Soybean Utilization Alternatives,* University of Minnesota, (1988) 203–211]. Removal of the raffinose saccharides was associated with increased utilization of the cellulosic and hemicellulosic fractions of the soybean meal.

A variety of processed vegetable protein products are produced from soybean. These range from minimally processed, defatted items such as soybean meal, grits, and flours to more highly processed items such as soy protein concentrates and soy protein isolates. In other soy protein products the oil is not extracted, full-fat soy flour for example. In addition to these processed products, there are also a number of speciality products based on traditional Oriental processes, which utilize the entire bean as the starting material. Examples include soy milk, soy sauce, tofu, natto, miso, tempeh, and vuba.

Examples of use of soy protein products in human foods include soy protein concentrates, soy protein isolates, textured soy protein, soy milk, and infant formula. Facilities and methods to produce protein concentrates and isolates from soybeans are available across the world. One of the problems faced by producers of soy protein concentrates and isolates is the challenge of selectively purifying the protein away from the raffinose saccharides. Considerable equipment and operating costs are incurred as a result of removing the large amounts of raffinose saccharides that are present in soybeans.

The problems and costs associated with raffinose saccharides could be reduced or eliminated through the availability of genes that confer a reduction of raffinose saccharide content of soybean seeds. Such genes could be used to develop soybean varieties having inherently reduced raffinose saccharide content. Soybean varieties with inherently reduced raffinose saccharide content would improve the nutritional quality of derived soy protein products and reduce processing costs associated with the removal of raffinose saccharides. Said low raffinose saccharide soybean varieties would be more valuable than conventional varieties for animal and human diets and would allow mankind to more fully utilize the desirable nutritional qualities of this edible legume.

Efforts have been made to identify soybean germplasm that may contain genes that confer a low seed raffinose saccharide content phenotype. Surveys of the soybean germplasm collection, including *Glycine max, Glycine soja,* and *Glycine hirsutum,* tentatively identified PI lines that seemed to offer the potential for reducing raffinose saccharide content via conventional breeding [see Hymowitz, T., et al. Comm. In *Soil Science and Plant Analysis* (1972) 3:367–373, Hymowitz, T., et al. *Agronomy J.* (1972) 64:613–616, Hymowitz, T., and Collins, F. I. *Agronomy J.* (1974) 66:239–240, Openshaw, S. J., and Hadley, H. H. *Crop Science* (1978) 18:581–584, Openshaw, S. J., and Hadley, H. H. *Crop Science* (1981) 21:805–808, and Saravitz (1986) Ph.D. Thesis, North Carolina State University, Horticultural Science Department]. However, when assayed under identical analytical conditions, none of the lines suggested in these prior surveys proved to be significantly lower in raffinose saccharide content than the currently available elite soybean lines. The primary reason for this may be due to the instability of the low raffinose saccharide phenotype. Results from germplasm collection surveys are highly influenced by the quality of the seed obtained from the collection. This is particularly true for raffinose saccharides in that seed carbohydrate composition has been shown to be influenced by seasonal, genetic and environmental factors [Jacorzynski, B. and Barylko-Pikielna, N. *Acta Agrobotanica* (1983) 36:41–48, Saravitz (1986) Ph.D. Thesis, North Carolina State University, Horticultural Science Department]. Furthermore, seed storage conditions prior to analysis can also influence the composition [Ovacharov and Koshelev *Fiziol. Rast.* (1974) 21:969–974, Caffrey et al. *Plant Physiol.* (1988) 86:754–758, Schleppi and Bums *Iowa Seed Science* (1989) 11:9–12]. As a result, the potential exists for falsely identifying soybean germplasm whose reduced raffinose saccharide content is not heritable, but rather dur to the environment in which the seeds were produced or stored prior to analysis. Collectively, these factors have severely limited efforts to identify soybean genes that reduce raffinose saccharide content.

The difficulty and unreliability of screens for raffinose saccharide content is reflected by the paucity of publicly available soybean carbohydrate data as compared to protein and oil quality data. For example, the USDA has numerous publications revealing the protein and oil quality contents for almost all (ca. 14,000) of the soybean PI lines in the USDA collection. However, although raffinose saccharide content is known to be a serious problem in soybeans, very little of the PI collection has actually been screened for this trait.

Demonstration of the stability of a low raffinose saccharide phenotype in subsequent generations (heritability of the phenotype) is required if the germplasm is to be of any utility in improving seed quality. It is therefore essential that any putative germplasm source be regrown to obtain fresh seed and reassayed (with appropriate lines as experimental controls) before it is declared as a potential source of low raffinose saccharide genes. Once the heritability (stability) of the phenotype is demonstrated, it is desirable to determine the inheritance (number and nature of genes that are involved) of the low raffinose saccharide phenotype. Heritability and inheritance information is extremely valuable for attempts to breed new soybean varieties that contain the low raffinose saccharide trait.

In light of the above described factors, it is apparent that soybean plants with heritable, substantially reduced raffinose saccharide content useful for preparing soy protein products with an improved carbohydrate content are needed. Heretofore, the only means to acheive a desirable raffinose saccharide content was to physically and/or chemically treat the soybean.

SUMMARY OF THE INVENTION

The present invention comprises soybean line(s) with a heritable phenotype of a seed stachyose content of less than 50 $\mu$mol/g or a seed total raffinose saccharide content of less than 120 $\mu$mol/g. Soybean seeds with this stachyose content are also an embodiment of this invention. Soybean line(s) having a genotype at the Stc1 locus that confers a phenotype of a seed stachyose content of less than 50 $\mu$mol/g or a total raffinose saccharide content of less than 120 $\mu$mol/g is also an embodiment of this invention. Preferred are seeds, plant lines producing seeds, plants producing seeds and the progeny of such plant lines, plants and seeds that have a heritable phenotype of a seed stachyose content of less than 30 $\mu$mol/g or less than 15 $\mu$mol/g, respectively. A further embodiment of the invention is a soybean line(s) or seeds having the stachyose or total raffinose saccharide contents set forth above and a seed protein content of greater than 42%.

A further embodiment of the invention is a method of using a soybean line having a heritable phenotype of a seed stachyose content of less than 50 $\mu$mol/g, the method comprising processing said seeds to obtain a desired soy protein product. A further embodiment of the invention is a method of making a soy protein product comprising processing seeds of a soybean line having a heritable phenotype of a seed stachyose content of less than 50 $\mu$mol/g. Preferred embodiments are methods of using a soybean line having a genotype at the Stc1 locus phenotype of a seed stachyose content of less than 50 $\mu$mol/g, 30 $\mu$mol/g, and 15 $\mu$mol/g, respectively to process said seeds to obtain a desired soy protein product. Additional preferred embodiments are methods of making a soy protein product comprising processing seed of a soybean line having a genotype at the Stc1 locus phenotype that confers a seed stachyose content of less than 50 $\mu$mol/g, less than 30 $\mu$mol/g, or less than 15 $\mu$mol/g respectively.

The present invention further comprises methods for making a full fat soy protein product, the method comprising: (a) cracking seeds from a soybean line having a heritable phenotype of a seed stachyose content of less than 50 $\mu$mol/g to remove the meats from the hulls; (b) flaking the meats obtained in step a to obtain a desired flake thickness; (c) heat-denaturing the flakes obtained in step (b) to obtain a desired Nitrogen Solubility Index; and (d) grinding the denatured flakes of step (c) to obtain a desired particle size. The present invention further comprises adding soybean hulls to the product of step (c) to obtain a full fat soy protein product having a maximum fibre content of 7% at a moisture content of 12%.

The present invention further comprises a method of making a defatted soy protein product comprising: (a) cracking seeds from a soybean line having a heritable phenotype of a seed stachyose content of less than 50 μmol/g to remove the meats from the hulls; (b) flaking the meats obtained in step (a) to obtain a desired flake thickness; (c) contacting the full flakes obtained in step (b) with a solvent to extract oil from the flakes to a desired content level; (d) heat-denaturing the defatted flakes obtained in step (c) to obtain a desired Nitrogen Solubility Index; and (e) grinding the denatured, defatted flakes obtained in step (d) to obtain a desired particle size. The present invention further comprises adding soybean hulls to the product of step (c) to obtain a defatted soy protein product having a maximum fibre content of 7% at a moisture content of 12%. The heat-denaturing may be accomplished by flash desolventization. Extruding the full fat soy protein product or the defatted soy protein product to texturize or structure the product after the grinding step is also included in the present invention.

The present invention further comprises a method of making a soy protein concentrate product comprising: (a) cracking seeds from a soybean line having a heritable phenotype of a seed stachyose content of less than 50 μmol/g to remove the meats from the hulls; (b) flaking the meats obtained in step (a) to obtain a desired flake thickness ; (c) contacting the full fat flakes obtained in step (b) with a first solvent to extract oil from the flakes to a desired oil content level; (d) contacting the defatted flakes obtained in step (c) with a second solvent to obtain a soy protein concentrate product with a protein content (6.25×N) of not less than 65% (db). A preferred embodiment of this invention uses an aqueous alcohol solution from 55% to 90% as a second solvent, the soy protein concentrate product obtained in step (d) having a protein content (6.25×N) of not less than 70% (db). A second preferred embodiment of this invention uses an acidic solution of pH 4 to pH 5 as a second solvent.

The present invention further comprises a method of making an isoelectric soy protein isolate product comprising: (a) cracking seeds from a soybean line having a heritable phenotype of a seed stachyose content of less than 50 μmol/g to remove the meats from the hulls; (b) flaking the meats obtained in step (a) to obtain a desired flake thickness; (c) contacting the full fat flakes obtained in step (b) with a first solvent to extract oil from the flakes to a desired oil content level; (d) contacting the defatted flakes obtained in step (c) with an aqueous solution of pH 8 to pH 9; (e) separating the soluble and insoluble fractions of the product of step (d) by physical means; (f) adjusting the pH of the soluble fraction obtained in step (e) to obtain a protein precipitate; (g) separating the protein precipitates of step (f) from the soluble fraction by physical means to obtain a soy protein isolate; (h) washing the product of step (g) with water; and (i) spray-drying the washed product of step (h) to obtain an isoelectric soy protein isolate product. A further embodiment of this invention comprises mixing the soy protein isolate product obtained in step (i) with sufficient alkali to increase the solubility of the product to a desired level.

The present invention further comprises a method of making a pet food product comprising: (a) combining farinaceous materials, a soy protein product derived from the processing of soybean seed with a heritable stachyose content of less than 50 μmol/g at an inclusion rate of less than 41%, animal fat, vitamins, minerals, and salt into a mixture; (b) extruding the mixture of step (a) through a die at an elevated temperature and pressure; (c) portioning the extruded mixture of step (b) into pieces of a desirable size; and (d) drying the products of step (c) to a desirable moisture content preferably a moisture content of less than 10%.

The present invention further comprises a full fat soy protein product derived from the processing of soybean seed with a heritable stachyose content of less than 50 μmol/g, preferably less than 30 μmol/g, or more preferably less than 15 μmol/g. A further embodiment of the invention also contains a protein content of greater than 42% at each of the stachyose content levels stated.

The present invention further comprises an undenatured, defatted soy protein product derived from the processing of soybean seeds with a heritable seed stachyose content of less than 50 μmol/g, preferably less than 30 μmol/g, or more preferably less than 15 μmol/g.

The invention further includes a heat-processed, defatted, desolventized, and toasted soy protein product derived from the processing of soybean seeds with a heritable seed stachyose content of less than 50 μmol/g, preferably less than 30 μmol/g, or more preferably less than 15 μmol/g.

The present invention further comprises a heat-processed, defatted, desolventized and toasted soy protein product that (a) is derived from the processing of soybean seeds with a heritable seed stachyose content of less than 50 μmol/g, preferably less than 30 μmol/g, or more preferably less than 15 μmol/g and (b) has a true metabolizable energy (TME$_N$) content of greater than 2850 Kcal/Kg (db).

The present invention further comprises a heat-processed, defatted, desolventized and toasted soy protein product that (a) is derived from the processing of soybean seeds with a heritable seed stachyose content of less than 50 μmol/g, preferably less than 30 μmol/g, or more preferably less than 15 μmol/g and (b) is derived from soybean seeds with a protein content of greater than 42%.

The present invention further comprises a heat-processed, defatted, flash-desolventized soy protein product derived from the processing of soybean seeds with a heritable seed stachyose content of less than 50 μmol/g, preferably less than 30 μmol/g, or more preferably less than 15 μmol/g.

The invention further includes an undenatured, defatted, flash desolventized soy protein product that (a) is derived from the processing of soybean seeds with a heritable seed stachyose content of less than 50 μmol/g, preferably less than 30 μmol/g, or more preferably less than 15 μmol/g amd (b) is derived from soybean seeds with a protein content of greater than 42%.

The present invention further comprises a heat-processed, defatted soy protein product derived from the processing of soybean seeds with a heritable seed stachyose content of less than 50 μmol/g, preferably less than 30 μmol/g, or more preferably less than 15 μmol/g. A preferred embodiment of this invention is a protein product that has a Nitrogen Solubility Index of greater than 60, a more preferred embodiment has a Nitrogen Solubility Index of between 20 and 60, and the most preferred embodiment has a Nitrogen Solubility Index of less than 20.

The present invention further comprises a soy protein concentrate product having a protein content (6.25×N) of not less than 65% (db) produced by the method comprising: (a) cracking seeds from a soybean line having a heritable phenotype of a seed stachyose content of less than 50 μmol/g to remove the meats from the hulls; (b) flaking the meats obtained in step (a) to obtain a desired flake thickness; (c) contacting the full fat flakes obtained in step (b) with a first solvent to extract oil from the flakes to a desired oil content level; (d) contacting the defatted flakes obtained in step (c)

with a second solvent to obtain a soy protein concentrate product with a protein content (6.25×N) of not less than 65% (db).

The present invention further comprises a pet food product that (a) is derived from the processing of soybean seeds with a heritable seed stachyose content of less than 50 $\mu$mol/g, preferably less than 30 $\mu$mol/g, or more preferably less than 15 $\mu$mol/g and (b) has a soybean protein product inclusion rate of between 25% and 41%.

The present invention further comprises mutant soybean lines that have been deposited under the terms of the Budapest Treaty at ATCC (Americal Type Culture Collection, 12301 Parklawn Drive, Rockville, Md. 20852), and bear the following accession numbers:

| Mutant Soybean Line | Accession Number |
| --- | --- |
| LR484 | ATCC 75325 |
| LR33*LR28 | ATCC XXXX |
| LR3705 | ATCC XXXX |
| LR4271 | ATCC XXXX |

The present invention further comprises a soybean line derived from a cross between any soybean line, preferably an agronomically elite line, and LR28, LR484 (ATCC 75325), LR3705, LR4271, or LR33*LR28, the cross yielding a soybean line with a heritable phenotype of less than 50 $\mu$mol/g seed stachyose content or a seed total raffinose saccharide content of less than 120 $\mu$mol/g. Progeny from any pedigree involving LR28, LR484 (ATCC 75325), LR3705, LR4271, or LR33*LR28 as at least one parent, the plant having a heritable phenotype of less than 50 $\mu$mol/g seed stachyose or less than 120 $\mu$mol/g total raffinose saccharide, are also embodiments of the present invention. Seeds of these crosses displaying these stachyose and total raffinose saccharide levels are also an embodiment of this invention. This invention preferably has an additional characteristic of protein content greater than 42%.

The present invention further comprises a method for producing a soybean protein product derived from processing soybean seeds having a heritable total raffinose saccharide content of less than 120 $\mu$mol/g or a stachyose content of less than 50 $\mu$mol/g comprising: (a) crossing any soybean line, preferably an agronomically elite soybean line, with LR28, LR484, LR3705, LR4271, or LR33*LR28 to obtain an F1 hybrid; (b) crossing and/or selfing the F1 hybrid for at least one generation to obtain segregating progeny; (c) identifying the progeny of step (b) with a heritable total raffinose saccharide seed content of less than 120 $\mu$mol/g or a seed stachyose content of less than 50 $\mu$mol/g; and (d) processing the seed selected in step (c) to obtain the desired soybean protein product.

A further aspect of the invention is a method of using a soybean line having a genotype at the Stc1 locus that confers a heritable seed phenotype of less than 50 $\mu$mol/g stachyose or less than 120 $\mu$mol/g total raffinose saccharide content to produce progeny lines, the method comprising: (a) crossing a soybean plant containing a stc1x allele with any soybean parent, preferably an agronomically elite soybean parent, which does not contain said allele, to yield a F1 hybrid; (b) crossing and/or selfing the F1 hybrid for at least one generation to obtain segregating progeny; (c) identifying the progeny of step (b) with a heritable seed stachyose content of less than 50 $\mu$mol/g or a total raffinose saccharide content of less than 120 $\mu$mol/g.

BRIEF DESCRIPTION OF THE DRAWINGS

FIG. 2 shows a unimodal distribution of F2 phenotypes resulting from the LR28*LR484 cross. None of the F2 plants produced seed in the $\alpha$-galactoside range of conventional soybean plants.

DETAILED DESCRIPTION OF THE INVENTION

Figure 1A:
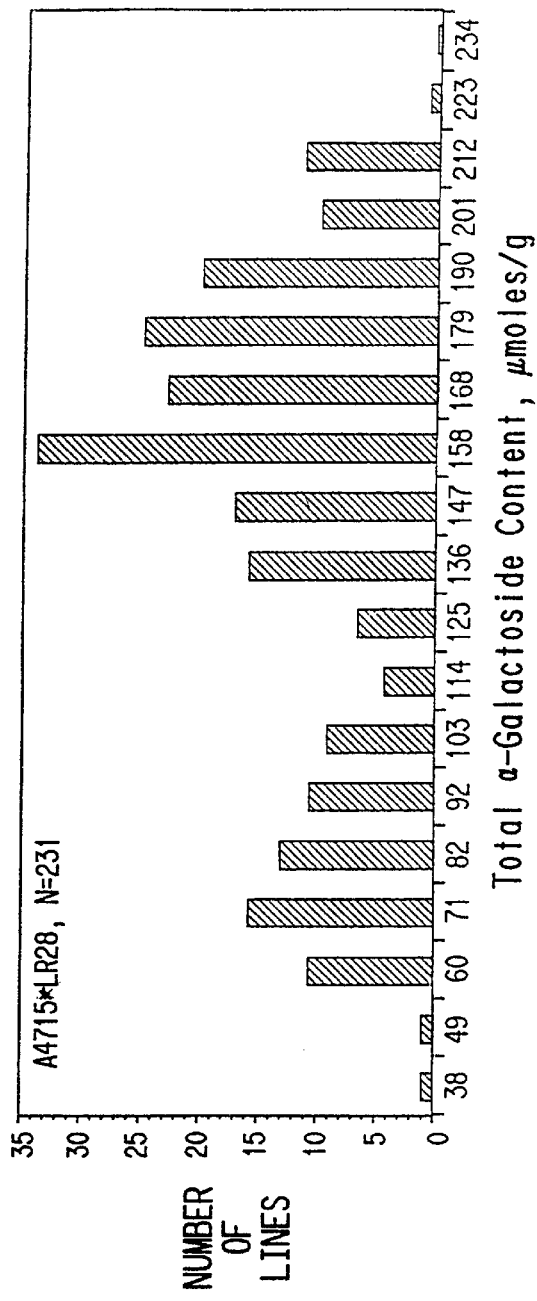
FIGS. 1(A–D) show the distribution of total $\alpha$-galactoside content in four segregating F2 populations resulting from the cross between LR28 and four agronomically elite lines. The figures graphically support the levels of total raffinose saccharides ["less than 120 $\mu$mol/g]".

This invention provides soybean genes and methods to improve the carbohydrate composition of soybean seeds and derived products. The invention teaches examples of major genes stc1a and stc1b that can be used to reduce the raffinose saccharide content of soybean seeds. This invention also teaches examples of modifier genes than can be used to enhance the expression of said major genes. This invention also teaches methods of discovering new major genes and modifier genes that can be used to reduce the raffinose saccharide content in soybean seeds.

Through breeding techniques, improved seed carbohydrate traits can be combined with any other desirable seed or agronomic traits. Examples of other desirable traits include, but are not limited to, high seed protein content and high seed yield. Processing of seeds from soybean lines containing stc1a or stc1b will produce soy protein products with reduced raffinose saccharide content and improved metabolizable energy and thus possess added value for individuals who either produce soy protein products for animal, including human, food uses or use soy protein products as major components in the diets for themselves or their animals.

In the context of this disclosure, a number of terms shall be utilized. As used herein, "soybean" refers to the species *Glycine max, Glycine soja,* or any species that is sexually cross compatible with *Glycine max*. A "line" is a group of plants of similar parentage that display little or no genetic variation between individuals for a least one trait. Such lines may be created by one or more generations of self-pollination and selection, or vegetative propagation from a single parent including by tissue or cell culture techniques. "Germplasm" refers to any plant(s), line(s), or population of plants that has/have the potential to be used as parent(s) in a plant breeding program. As used herein, "PI" or "plant introduction" refers to one of many soybean germplasm lines collected and maintained by the the United States Department of Agriculture. "Agronomic performance" or "agronomics" refers to heritable crop traits such as good emergence, seedling vigor, vegetative vigor, herbicide tolerance, adequate disease tolerance and, ultimately, high seed yield. "Seed yield" or "yield" refers to productivity of seeds per unit area (e.g., bushels/acre or metric tons/hectare) that a particular soybean line is capable of producing in a specific environment or generally in many environments. An "agronomically elite line" or "elite line" refers to a line with desirable agronomic performance that may or may not be used commercially. A "variety", "cultivar", "elite variety", or "elite cultivar" refers to an agronomically superior elite line that has been extensively tested and is (or was) being used for commercial soybean production. "Mutation" refers to a detectable and heritable genetic change (either spontaneous or induced) not caused by segregation or genetic recombination. "Mutant" refers to an individual, or lineage of individuals, possessing a mutation. A "population" is any group of individuals that share a common gene pool. In the instant invention, this includes M1, M2, M3, M4, F1, and F2 populations. As used herein, an "M1 population" is the progeny of seeds (and resultant plants) that have been exposed to a mutagenic agent, while "M2 population" is the progeny of self-pollinated M1 plants, "M3 population" is the progeny of self-pollinated M2 plants, and "M4 population" is the progeny of self-pollinated M3 plants. As used herein, an "F1 population" is the progeny resulting from cross pollinating one line with another line. The format used herein to depict such a cross pollination is "female parent*male parent". An "F2 population" is the progeny of the self-pollinated F1 plants. An "F2-derived line" or "F2 line" is a line resulting from the self-pollination of an individual F2 plant. An F2-derived line can be propagated through subsequent generations (F3, F4, F5 etc.) by repeated self-pollination and bulking of seed from plants of said F2-derived line. A "pedigree" denotes the parents that were crossed to produce the segregating population from which a given line was selected. For example, a pedigree of A*B for a given line C indicates A and B are the parents of C. Although lines of similar pedigree may have a trait in common (due to selection for said trait), said lines of similar pedigree may be quite different in terms of other traits. "Heritability" is a relative term referring to the extent to which a given phenotype is determined by genetic factors as opposed to environmental or analytical error factors. An "environment" is used to define a specific time, general geographical area, and climatic conditions in which soybean plants were grown to produce seeds. Within the context of this application, soybean seeds produced in a common environment were seeds that were produced on plants that were planted during the same day, within the same 1 km radius, and under similar growing conditions. Environments within this application are identified by the year and geographical site at which seeds were produced. A "heritable trait" refers to a phenotype that is largely determined by genetic factors and is relatively stable and predictable over many environments. "Heritability" does not necessarily imply that said genetic factors have been characterized. "Inheritance" refers to the actual number and nature of genes that confer a given heritable trait. For example, Mendelian segregation patterns are used to deduce the "inheritance" of a trait. "Inherent" is used to denote a plant material or seed characteristic that is conferred by the genetic makeup of the plant producing said material or seed as opposed to the environment in which the plant was grown or the way that the plant material or seed was stored or processed. Since raffinose saccharide content of soybean seeds is known to decrease with weathering and aging of seeds [Ovacharov and Koshelev *Fiziol. Rast.* (1974) 21:969–974, Caffrey et al. *Plant Physiol.* (1998) 86:754–758, Schleppi and Burns *Iowa Seed Science* (1989) 11:9–12], all claims regarding the heritable carbohydrate content of seeds in the current application are in reference to the carbohydrate content of seeds that have been stored for less than one year at 1 to 27° C. and at 0 to 70% relative humidity.

As used herein, "total α-galactoside" content refers to all seed α-linked carbohydrate soluble in the solvent system described herein and is capable of being assayed using the α-galactosidase/galactose dehydrogenase method described herein. "Total raffinose saccharides" refers to the seed α-galactose content soluble in the solvent system described herein and represented by the sum of stachyose (2 moles α-galactose/mole), raffinose (1 mole α-galactose/mole) and galactinol (1 mole α-galactose/mole) as determined by methods described herein. "Raffinose saccharide content" is a general term referring to the seed raffinose saccharide content as determined by any type of analytical method. The term "protein content (6.25×N)" as used herein refers to the relative protein content of instant soybean products as ascertained by A.O.C.S. Recommended Practice Ba 4a-38 ("determines as ammonia the total nitrogen content and protein as 6.25 times the nitrogen content of the sample").

The term "as is" refers to the basis (i.e., moisture content at the time of analysis, as determined by A.O.C.S. Method Ba 2a-38, of a given seed or soy protein product) used to express the units of carbohydrate and protein content. The term "dry basis" or "db" refers to materials that have 0% moisture. Dry basis measurements can be obtained by analyzing materials that have been placed in a 45° C. oven until they have reached constant weight or by mathematically converting "as is" measurements to 0% moisture. Most of the dry basis measurements with this specification have been obtained through mathematical conversion. Although mature soybeans and protein products can vary in moisture content from 6 to 13%, Inventor's own measurements and those of the United States Department of Agriculture indicate that the normal moisture content of mature soybeans is 7 to 10% with an average of 8%. Accordingly, "as is" measurements have been converted to dry basis using an average moisture content of 8%. This was done by dividing all "as is" values by 0.92. All carbohydrate and protein phenotypes within this specification are expressed as dry basis unless otherwise specified.

The term "Stc1 locus" refers to a genetic locus within soybean that affects raffinose saccharide content in soybean seeds. The term "Stc1" (with a capital "S") refers to the wild type allele that confers a normal raffinose saccharide content. The terms "stc1a" and "stc1b" (with a lower case "s") refer to two separate but allelic soybean genes at the Stc1 locus, that confer low raffinose saccharide content. The term "stc1x" (lower case "s") is a general term referring to any allele at the Stc1 locus (including stc1a, stc1b, and other possible alleles) that confer a low total raffinose saccharide phenotype. "LR28" (an abbreviation synonymous with "PI 200.508") is the designation for a soybean line that was the source of the stc1a gene discovered by the Inventors. "LR484" is the designation for a soybean line derived from mutagenesis of elite cultivar "Williams 82". LR484 is the source of gene "stc1b" discovered by the Inventors. The phrase "line(s) containing stc1a" or "stc1a line(s)" indicates that the line(s) is homozygous for stc1a as evidenced by the line's pedigree and abnormally low raffinose saccharide content. The phrase "line(s) containing stc1b" or "stc1b line(s)" indicates that the line(s) is homozygous for stc1b as evidenced by the line's pedigree and abnormally low raffinose saccharide content. The phrase "lines containing stc1x" or "stc1x line(s)" indicates that the line(s) is homozygous for stc1x as evidenced by the line's pedigree and abnormally low raffinose saccharide content. "Conventional soybean lines" refers to lines that do not contain an stc1x allele.

A "major" gene is a gene, such as stc1a or stc1b, that causes a significant change in phenotype in most or all genetic backgrounds. For example, stc1a or stc1b, when inherited by any soybean line, will greatly reduce raffinose saccharide production in seed of said line. "Modifier(s)" or "modifier gene(s)" are genes that have a phenotypic effect but only when inherited in combination with a major gene. Hence said gene(s) "modify" the expression of a major gene. For example, as revealed in the current application, when a stc1x line is crossed with certain conventional lines, some of the progeny from such crosses have a heritably lower raffinose saccharide content than the parent line from which the stc1x gene was obtained. This is sufficient evidence that the conventional line contains gene(s) that enhance or "modify" the expression of the stc1x gene. Although the Mendelian inheritance pattern of such modifier genes may be difficult to ascertain, the heritability of the modified phenotype alone is proof that such modifier gene(s) exist.

An "unmodified stc1x line" is a descendent of either LR28 or LR484 that is not significantly lower in raffinose saccharide content than LR28. Hence, when soybean plants are produced side by side in a given environment, LR28 or any unmodified stc1x line can serve as a control for comparison to other lines that are being tested for the presence of modifier genes.

In order to simplify the description of the various raffinose saccharide phenotypes discovered by the Inventors, certain terms are used within the context of this application. All of the carbohydrate phenotypes in this Application are given in $\mu$mol per gram of seed on a dry basis (values adjusted to 0% seed water content). Since stachyose is the most prevelant of the raffinose saccharides found in soybean. Inventors have found stachyose to be the most reliable monitor of genes that affect the raffinose saccharide pool in soybean seed. Although seed galactinol content of stc1x lines is more prone to environmental (non-genetic) variation, certain modifier genes disclosed herein can be tracked by their ability to limit accumulation of galactinol in stc1x lines. Therefore, all phenotypes disclosed herein are based on stachyose content while a subset of said phenotypes are based on a combination of both stachyose and galactinol content. Raffinose content, although practically eliminated by stc1x genes, is a less effective monitor of Inventors' disclosed genes than stachyose and galactinol content. Table 1 shows the typical raffinose saccharide ranges for the phenotypes described below. The following abbreviations are used in table throughout this text: STC=seed stachyose content; RAF=seed raffinose content; GAL=seed galactinol content; RSA=seed total raffinose saccharide content.

TABLE 1

Typical Seed Raffinose Saccharide Phenotypic Ranges for Inventors' Soybean Germplasm Versus Conventional Germplasm

| PHENO-TYPE | STC | RAF | GAL | RSA | GENES INVOLVED |
|---|---|---|---|---|---|
| | | $\mu$mol/g db | | | |
| "high" | 50–100 | 10–20 | 0–5 | 120–220 | conventional |
| "low" | <50 | | | <120 | general term |
| "low1" | 15–35 | 2–5 | 20–50 | 50–100 | stc1x only |
| "low2" | 5–10 | 0–5 | 20–50 | 30–80 | stc1x + modifier(s) |
| "low3" | 5–10 | 0–5 | 10–20 | 20–30 | stc1x + modifier(s) |
| "low4" | 0–10 | 0–5 | 0–5 | 0–20 | stc1x + LR33 modifier |

The "high" phenotype disclosed herein refers to the raffinose saccharide content of conventional soybean lines. "High" is more precisely defined as a seed stachyose content greater than 50 $\mu$mol/g, the range observed in conventional soybeans that have been allowed to reach full maturity. Occasionally, conventional soybeans will produce less than 50 $\mu$mol/g stachyose but these have invariably been soybeans that were harvested prematurely and not permitted to accumulate stachyose to their genetic potential. Such artificially low stachyose contents are not heritable.

The term "low" seed raffinose saccharide content is a term that can be used in a general sense to include anything that lies below the range of seed raffinose saccharide contents displayed by conventional soybean lines. Based on data disclosed within this specification, anything below 50 $\mu$mol/g seed stachyose content or 120 $\mu$mol/g seed total raffinose saccharide content was considered to be a phenotype below the range normally displayed by conventional soybean lines when the seed is allowed to reach full maturity before harvest. When appropriate, the term "low" is displaced by the more specific phenotypes "low1", "low2", "low3", and "low4" as the discovery of the specific phenotypes is revealed within the application.

The "low1" phenotype, as used herein, is a seed stachyose phenotype that is not significantly different from that of LR28 seed or an unmodified stc1x line grown in a given environment. The typical "low1" seed stachyose content range for unmodified stc1x lines is 15 to 35 $\mu$mol/g. As disclosed previously, stc1x also reduced raffinose. Although stc1x increases galactinol content, the net effect of stc1x is a dramatic reduction in the total seed raffinose saccharide pool.

The "low2" phenotype, as used herein, refers to a seed phenotype that is significantly (statistically) lower in stachyose than the low1 phenotype of LR28 or other unmodified stc1x lines when grown in the same environment. The low2 phenotype is derived from the combination of stc1x (from LR28 or LR484) and modifier gene(s) from other germplasm lines. Although the low2 phenotype is typically in the range of 5 to 10 $\mu$mol/g seed stachyose content, the statistical borderline between low1 and low2 check lines has been about 14 $\mu$mol/g in tests conducted by the Inventors over many environments. Due to the effect of environment on galactinol content of low1 and low2 lines, there is some overlap between these two phenotypes in terms of the total raffinose saccharide pool. Therefore, stachyose content is the primary criterion used to differentiate between the low1 and low2 phenotypes.

The "low3" phenotype, as used herein, is similar to a low2 phenotype in terms of stachyose content but with a significant reduction in the galactinol accumulation than is normally observed in seed of low1 and low2 stc1x lines. In addition to a stc1x gene, low3 types contain modifier gene(s) that reduce both stachyose content and galactinol content.

The "low4" phenotype, as used herein, refers to a low3 phenotype with little or no galactinol accumulation. The low4 phenotype results from a combination of stc1x plus modifier gene(s) derived from mutant LR33 described herein.

Although the above phenotypes have been very repeatable over environments, atypical environmental conditions can affect the phenotypic expression of many genes including genes that control seed raffinose saccharide content. Of particular significance is the fact that soybean breaders commonly use Puerto Rico and other tropical environments to advance soybean populations through 1 or 2 generations of inbreeding during the fall/winter months. As these environments get closer to the equator, the resultant photoperiod (daylength) gets closer to 12 hours on a year-round basis. This is much different than the peak summer photoperiod of most commercial soybean production areas which have a 14 to 16 hour peak photoperiod. Soybean plant development is very sensitive to photoperiod and commercial varieties are therefore bred to mature within 4 to 6 months after planting (the "generation time") when grown in the region targeted for commercial production. Although soybeans can be grown to maturity in the tropics, the short photoperiod hastens development and shortens the generation time to approximately 3 months. The short generation time compresses flowering, seed set, and seed filling periods. This abnormal development may affect the expression of many traits including seed raffinose saccharide content.

As demonstrated by the instant disclosure, tropical environments such as Puerto Rico have been and will be a valuable resource for the discovery of valuable raffinose saccharide germplasm. Inventors have found that seeds of check lines produced in Puerto Rico are quite similar in raffinose saccharide phenotype to the same lines grown in the mainland United States. Although the actual ranges of stachyose, raffinose, and galactinol may be shifted, the relative differences among replicated plants of known high, low1, low2, low3, and low4 control lines remain the same. Puerto Rico has also been used as an environment to grow segregating F2 populations and then make single plant selections for raffinose saccharide content. This has been a very effective method of differentiating stc1x from conventional soybean lines. However, selections among low phenotypes (low1, low2, low3, low4) based on single plants grown in Puerto Rico are not always accurate. Therefore, a selection protocol that requires subsequent testing of replicated progeny of said selections in an environment typical of commercial soybean production has been established.

Due to the effect of environment on the expression of genes affecting raffinose saccharide content, putative germplasm with major genes for raffinose saccharide should be confirmed by growing said germplasm in least 2 different test environments and analyzing seed of said germplasm produced in those environments. At least one of the test environments should be one that closely approximates the targeted commercial production conditions. Plants of said germplasm lines should be replicated in each environment so that a statistical measure of raffinose saccharide phenotype can be calculated. In addition, claims about the phenotypic expression of said germplasm should be based on seeds produced in the environment that approximates commercial production conditions.

Due to the effect of environment on seed raffinose saccharide content, the Inventors have also devised a method of discovering and confirming the heritability of modifier genes that enhance the expression of major genes such as stc1x. The following method referred to as the "modifier discovery procedure" can also be used to discover and confirm modifiers that affect any trait of interest. The procedure comprises:

1) crossing germplasm lines of any type with unmodified stc1x lines to obtain F1 progeny, 2) self pollinating said F1 progeny for one or more generations to obtain a population of segregating inbred lines, 3) planting said segregating lines in one environment and measuring the raffinose saccharide content of seed produced by each line in that environment, 4) selecting lines from step 3 with lower raffinose saccharide content than unmodified stc1x lines, 5) growing replicated plants of selected lines side-by-side with replicated plants of unmodified stc1x control lines in a second environment that approximates commercial soybean production conditions, 6) measuring the raffinose saccharide content of seed produced by replicated plants of each line grown in said second environment, and 7) using phenotypes from the second environment to identify lines that are inherently and significantly lower in seed raffinose saccharide content than the unmodified stc1x check lines.

Soybean inheritance and/or heritability studies are commonly initiated by crossing two parents that differ in the trait of interest to produce F1 and then segregating F2 progeny. The F2 progeny are then evaluated for the trait of interest and conclusions about the inheritance and/or heritability of a trait are drawn. It is often desirable to further inbreed F2 plants to improve the chances of selecting lines that are homozygous (true breeding) for all genes that affect the trait of interest. The inbred seed from each F2 plant can also be planted in another environment and used to replicate the genotype of each F2 plant so that a more reliable statistical measure of phenotype can be obtained for each F2-derived line. This is especially useful for quantitative traits that are influenced by environment to some degree. In addition to replicating each genotype, subsequent testing of F2-derived lines provides confirmation of phenotype in another environment and in another generation of inbreeding. The procedure outlined above was used to provide solid statistical evidence for the existence and heritability of genes that modify the expression of stc1x. This same procedure can be used to discover and confirm the existence of genes that affect other quantitative traits.

Since stachyose is the main carbohydrate of the soybean raffinose saccharide profile, the following examples rely on variation in stachyose content as the main basis for determining the statistical significance of differences among carbohydrate profiles. The mean and standard deviation for stachyose content of an unmodified stc1x check line (LR28 in most cases) was used as the basis of comparison. A line with a means stachyose content below that of the unmodified stc1x check line by more than three standard deviations was considered to be significantly lower in stachyose than said check line. Using this standard, the phenotypic designation "low2" (see Table 1) is used in Tables 7, 8 and 9 to denote carbohydrate profiles with a stachyose content that is significantly lower than the stachyose content of the unmodified stc1x check line. Germplasm that reduces the accumulation of galactinol in stc1x lines is also disclosed within this specification. In these cases, statistics for both stachyose and galactinol content were used to confirm the discovery and heritability of modifier genes. In Table 9, the phenotypic designation "low3" or "low4" is used to denote carbohydrate profiles that are significantly lower in both stachyose and galactinol than the unmodified stc1x check line. The difference between "low3" and "low4" is based upon the extent of galactinol reduction (see Table 1).

"Soy protein products" are defined as those items produced from soybean seed used in feeds or foods and include, but are not limited to, those items listed in Table 2.

TABLE 2

Soy Protein Products Derived from Soybean Seeds[a]

| Whole Soybean Products | Processed Soy Protein Products |
| --- | --- |
| Roasted Soybeans | Soybean Meal |
| Baked Soybeans | Soy Grits |
| Soy Sprouts | Full Fat and Defatted Flours |
| Soy Milk | Soy Protein Isolates |
|  | Soy Protein Concentrates |
| Speciality Soy Foods/Ingredients | Textured Soy Proteins |
| Soy Milk | Textured Flours and Concentrates |
| Tofu | Textured Concentrates |
| Tempeh | Textured Isolates |

TABLE 2-continued

Soy Protein Products Derived from Soybean Seeds[a]

| Whole Soybean Products | Processed Soy Protein Products |
|---|---|
| Miso | |
| Soy Sauce | |
| Hydrolyzed Vegetable Protein | |
| Whipping Protein | |

[a]See Soy Protein Products: Characteristics, Nutritional Aspects and Utilization (1987). Soy Portein Council "Processing" refers to any physical and chemical methods used to obtain the products listed in Table 2 and includes, but is not limited to heat conditioning, flaking and grinding, extrusion, solvent extraction, or aqueous soaking and extraction of whole or partial seeds. Furthermore, "processing" includes the methods used to concentrate and isolate soy protein from whole or partial seeds, as well as the various traditional Oriental methods in preparing fermented soy food products. Trading Standards and Specifications have been established for many of these products (see National Oilseed Processors Association Yearbook and Trading Rules 1991–1992). Products referred to as being "high protein" or "low protein" are those as described by these Standard Specifications. "NSI" refers to the Nitrogen Solubility Index as defined by the American Oil Chemists' Society Method Ac4 41. "KOH Nitrogen Solubility" is an indicator of soybean meal quality and refers to the amount of nitrogen soluble in 0.036 M KOH under the conditions as described by Araba and Dale [(1990) Poultry Science 69:76–83]. "White" flakes refer to flaked, dehulled cotyledons that have been defatted and treated with controlled moist heat to have an NSI of about 85 to 90. This term can also refer to a flour with a similar NSI that has been ground to pass through a No. 100 U.S. Standard Screen size. "Cooked" refers to a soy protein product, typically a flour, with an NSI of about 20 to 60. "Toasted" refers to a soy protein product, typically a flour, with an NSI below 20. "Grits" refer to defatted, dehulled cotyledons having a U.S. Standard screen size of between No. 10 and 80. "Soy Protein Concentrates" refer to those products produced from dehulled, defatted soybeans by three basic processes: acid leaching (at about pH 4.5), extraction with alcohol (about 55–80%), and denaturing the protein with moist heat prior to extraction with water. Conditions typically used to prepare soy protein concentrates have been described by Pass [(1975) U.S. Pat. No. 3,897,574; Campbell et al., (1985) in New Protein Foods, ed. by Altschul and Wilcke, Academic Press, Vol. 5, Chapter 10, Seed Storage Proteins, pp 302–338]. "Extrusion" refers to processes whereby material (grits, flour or concentrate) is passed through a jacketed auger using high pressures and temperatures as a means of altering the texture of the material. "Texturing" and "structuring" refers to extrusion processes used to modify the physical characteristics of the material. The characteristics of these processes, including thermoplastic extrusion, have been described previously [Atkinson, (1970) U.S. Pat. No. 3,488,770, Horan (1985) In New Protein Foods, ed. by Altschul and Wilcke, Academic Press. Vol. 1A, Chapter 8, pp 367–414]. Moreover, conditions used during extrusion processing of complex foodstuff mixtures that include soy protein products have been described previously [Rokey (1983) Feed Manufacturing Technology III, 222–237; McCulloch, U.S. Pat. No. 4,454,804].

Seeds from the plants of the present invention express an improved soluble carbohydrate content relative to commercial varieties. The improvements result in a reduced total raffinose saccharide content. The carbohydrate profile of these lines are dramatically different from the profiles seen in elite or germplasm lines used in or produced by other soybean breeding programs.

Three separate methods to produce the novel soybean genes of the present invention are taught. The first approach involved exhaustive screening of existing soybean germplasm collections for sources of genes conferring low raffinose saccharide content. This germplasm screen was successful despite the failure of previous attempts by others to select and confirm germplasm with significant reduction of raffinose saccharides. The second approach marks the first successful attempts to induce a mutation conferring low raffinose saccharide content. These first two approaches resulted in the discovery of major stc1x genes that can be used to develop soybean lines that are superior (in terms of reduced raffinose saccharide content) to any lines previously reported. The third approach was a system that involved the crossing of germplasm lines with stc1x lines that ultimately lead to the the discovery of modifier genes that enhance the expression of stc1x genes. These modifiers, in combination with stc1x, reduce raffinose saccharide content below that of unmodified stc1x lines.

After screening approximately 14,000 lines from germplasm collections, a soybean gene stc1a was discovered in line LR28 and shown to confer a reproducibly low total raffinose saccharide content (Example 1). To confirm its value as a source of altered carbohydrate content, the seed composition of LR28 was compared to that of a number of other PI's and elite lines that have been reported in the literature as having the genetic potential for improving the raffinose saccharide content of soybean. This analysis under identical assay conditions indicated that LR28 displayed a substantially reduced raffinose saccharide content compared to any currently known source of germplasm. Inheritance studies indicated that LR28 contains a single recessive to codominant gene (designated stc1a) that confers the low raffinose saccharide trait. Inventors have also demonstrated that high protein content segregates independently of stc1a and that high protein content can be recombined with low raffinose saccharide content by conventional breeding techniques to produce lines having both traits.

The second approach, mutagenesis, resulted in the creation of mutant gene stc1b that confers a low raffinose saccharide phenotype similar to that conferred by stc1a (Example 2). Genetic studies indicated that stc1b is allelic to stc1a. Consequently, it is expected that stc1b can be used as an alternative source of the low raffinose saccharide trait conferred by stc1a. As with stc1a, it is expected that stc1b will be recombined with any other heritable seed trait or agronomic trait of interest. Since the stc1b mutation was induced within the genetic background of an elite variety, it is expected that minimal breeding effort will be required to recombine stc1b with desirable agronomic performance.

While confirming the heritability of the major stc1x genes, modifier gene(s) were discovered that complement stc1x to further reduce raffinose saccharide content. Based on Inventors' experience with the expression of major and modifier genes in different environments, Inventors then developed a protocol for the discovery and confirmation of major genes and modifier genes that affect raffinose saccharide content. This protocol was used to show examples of modifier genes that can be used to reduce the inherent raffinose saccharide content of soybean seeds by up to 97%.

Given the perceived value of low raffinose saccharide content, it is surprising that previously reported sources of low raffinose saccharide germplasm have not been used commercially. The reason for this discrepancy is the fact that previously identified sources of low raffinose saccharides have been artifacts of environmental variation, poor quality seed, or analytical inconsistencies. Careful efforts by the Inventors demonstrated conclusively that previous attempts of others to select germplasm with significant reduction in raffinose saccharide content were unsuccessful. Unfortunately, failure of these germplasm sources to confirm have simply not been reported in the literature and may have resulted in wasted effort on the part of soybean breeders who have used such lines for breeding purposes. Prior to Inventors' discovery of stc1a and stc1b, a more critical evaluation of known lines would actually lead one to believe that genetic variation for low raffinose saccharide content does not exist with soybean. Despite such a forecase, Inventors' exhaustive efforts have resulted in the discovery of truly rare and valuable genes.

If the instant low raffinose saccharide germplasm is crossed with germplasm sources containing other desirable traits, it is expected that a fraction of the resultant progeny will inherit low raffinose saccharide content in combination with the desirable trait(s) from other germplasm sources. Desirable seed traits that will be combined with low raffinose saccharide content include (but are not limited to) high protein content, high methionine content, high lysine content, high oleic acid content, high stearic acid content, low palmitic acid content, low linoleic acid content, low linolenic acid content, lipoxygenase nulls, and trypsin inhibitor nulls. It is also expected that stc1x will be combined with any trait of agronomic significance to develop elite lines. Examples of such agronomic traits include (but are not limited to) emergence vigor, seedling vigor, vegetative vigor, disease resistance, pest resistance, herbicide resistance, drought resistance, lodging resistance, and high seed yield.

To demonstrate the effect of stc1x on the nutritional quality of soybeans, defatted, toasted soybean meals were prepared from lines homozygous for stc1x (low in raffinose saccharide content) and from conventional soybean lines (with normal raffinose saccharide content). The meals were assayed to determine their nitrogen-corrected, True Metagolizable Energy ($TME_N$) content for broilers. Meals from stc1x lines had significantly higher (ca. 12%) $TME_N$ and greater utilization of gross energy compared to meals from the conventional soybean lines. Even relatively modest increases in metabolizable energy content of a major feedstuff such a soybean meal can have major economic benefits for the animal feed and animal production industries, due to the extraordinarily large flocks that most commercial operations maintain. The improvement in quality of soybean meal from stc1x lines should provide an excellent opportunity to further increase the efficiency of animal husbandry throughout the world.

The utility of stc1x lines was further demonstrated by preparing pet foods from defatted, toasted meals from stc1a lines and comparing their raffinose saccharide composition to pet foods produced from meals from conventional soybean lines. Lines homozygous for stc1a produced soybean meal and a food with a substantially lower raffinose saccharide content than those from conventional lines. U.S. Pat. No. 4,454,804 (McCulloch), incorporated by reference herein, discloses methods for the production of such a pet food product. The product typically includes farinaceous ingredients such as wheat, corn, barley, oats, and the like, or their derivatives such as corn meal, hominy, wheat middlings, wheat germ, etc. Typically, the amount of farinaceous ingredients in the expandable mixture comprises between about 30% to 70% by weight of the mixture.

The product may also include one or more proteinaceous ingredients of vegetable, animal or fish origin such as soybean meal, soy grits, meat meal, bone meal, poultry meal, fish scrap and combinations thereof. Typically, the proteinaceous ingredients comprise between about 20% and 50% by weight of the mixture. The balance of the mixture may comprise salts, flavorings, colorings, vitamin supplements, minerals and other like ingredients to form a nutritionally balanced experiences temperatures substantially above 212° F., and preferably between 250° F. and 350° F. The pressures developed within the extruder at the die plate should be above the vapor pressure of water at its extrusion temperature, typically between about 25–600 psi.

In addition, defatted, white flakes were prepared from stc1a lines and conventional lines and their raffinose saccharide contents compared. White flakes from stc1a lines displayed a substantially reduced raffinose saccharide content compared to those from conventional lines. In addition, white flakes from stc1a lines displayed a substantially lower raffinose saccharide content than several commercially obtained soy protein products (flours, textured flour, concentrate, textured concentrate). This improved composition should enable manufacturers of these products to obtain improved quality of their final product. They should achieve the added benefit of increased efficiency in their manufacturing processes as considerable resources are needed to build and operate processing plates that have been designed to reduce the raffinose saccharide content during the manufacture of soy protein concentrates and isolates.

As was seen with the other commercial soy products, the white flakes from stc1a lines have a substantially improved raffinose saccharide content compared to that in the commercial soyfood products. Soyfood manufacturers could achieve many of the same benefits of improved nutritional quality and processing efficiency with the manufacture of other soy protein products described above.

It must be emphasized that the conditions described above were chosen to be representative to those found in commercial operations for the production of a desolventized, toasted high (i.e., >47.5% at 12% moisture) protein meal. The precise conditions used to process the materials will undoubtedly vary from those described in the instant invention, depending on the specific manufacturing process. However, by using conventional methods [see JAOCS (1981) 11, Number 3] to crack, dehull, flake, extract, and desolventize/toast, commercial operations should be able to prepare soy protein products from stc1x lines as easily as they currently do with conventional soybeans. Moreover, soy protein product manufacturers could choose to prepare other soy protein products by employing alternate processing conditions. For example, products with higher oil contents could be produced by not employing solvent extraction (e.g., full-fat products). In addition, alternative solvent extraction conditions (e.g., supercritical gas such as carbon dioxide) or solvents other than hexane (e.g., alcohols, methyl ethyl ketone, acetone, etc.) could be employed. Lower (e.g., minimum 44% protein at 12% moisture) protein products could be produced by altering the conditions used to separate hulls from the cracked meats or by adding hulls back to more highly processed materials. Further, edible products such as soyflours could be produced by using alternate toasting conditions (e.g., flash desolventization). Finally, the properties of soy protein products from stc1x lines could be affected through the use of processes such as, but not limited to, extrusion, jet cooking, or homogenization. Collectively, the results clearly demonstrate that the soybean genes described herein have widespread utility for the production of improved soy protein products from soybeans with inherently low raffinose saccharide content.

EXAMPLES

The present invention is further defined in the following Examples, in which all parts and percentages are by weight and degrees are Celsius, unless otherwise stated. It should be understood that these Examples, while indicated preferred embodiments of the invention, are given by way of illustration only. From the above discussion and these Examples, one skilled in the art can ascertain, and without departing from the spirit and scope thereof, can make various changes and modifications of the invention to adapt it to various usages and conditions. Further, the present invention is not to be limited in scope by the biological materials deposited, since the deposited materials are intended to provide illustrations of materials from which many embodiments may be derived. All such modifications are intended to fall within the scope of the appended claims.

Example 1

Discovery of Soybean Gene, stc1a, Conferring Improved Carbohydrate Composition

Assays for Raffinose Saccharide Content

Prior to analysis for raffinose saccharide content, seeds were allowed to air dry for at least 1 week to a moisture content of approximately 8% and then stored at approximately 40 to 50° C. and 40% relative humidity. Inventors' own measurements of many such air-dried samples indicated that the moisture content did not vary significantly from 8% (range of 7 to 10%) when stored at said conditions.

For each individual raffinose saccharide assay, typically 5 to 10 soybeans from a given plant were ground in a Cyclotech 1093 Sample Mill (Tecator, Box 70 S-25301, Hoganas, Sweden) equipped with a 100 mesh screen to yield a seed powder that was then analyzed. In most cases, raffinose saccharide content was determined for seed or derived products containing an "as is" moisture content of approximately 8%. In these cases, "as is" values were converted to a dry basis (db) by dividing measurements by 0.92. For comparison among certain lines or among certain soy protein products, the ground seed powder was placed in a forced air oven at 45° C. until the samples reached constant weight (0% moisture) prior to analysis. Hence, all raffinose saccharide measurements reported within this specification are on a common dry basis unless otherwise specified. Within this specification, three assays ("enzymatic", "TLC", and "HPLC") were used to determine the raffinose saccharide content. All three were performed on seed powder derived from the aforementioned grinding process.

In preparation for the "enzymatic" assay, after grinding each seed sample, approximately 30 mg of the resultant powder was weighed into a 13×100 mm screw cap tube and 1.6 mL of chloroform and 1.4 mL of methanol:water (4:3, v/v) was added. The precise powder weight of each sample was recorded and used to adjust the following assay results for sample to sample weight differences. The tubes were then capped, placed in racks and shaken on a rotary shaker for 60 min at 1800 rpm at room temperature. After extraction, the contents of the tubes were allowed to settle for 15 min. After settling, a 15 $\mu$L aliquot of the methanol:water phase was placed in a well of a 96 well microtiter plate and dried at 45° C. for 20 min. The dried wells were used as reaction vessels for the coupled "enzymatic" assay which employed α-galactosidase and galactose dehydrogenase as described previously (Schiweck and Busching (1969) Zucker 22:377–384, Schiweck and Busching (1975) Zucker 28:242–243, Raffinose Detection Kitb, Boehringer Mannheim GMBH, Catalog Number 428 167) with modifications of the assay conditions. The modifications of the assay included addition of Bovine Serum Albumin (15 mg/mL) to the assay and α-galactosidase buffers, increasing the temperature and time of the α-galactosidase incubation from room temperature to 45° C. and 30 min, and increasing the time of the galactose dehydrogenase incubation from 20 min to 60 min and using stachyose instead of raffinose for the α-galactoside standard. After incubation, the absorbance at 340 nm of the samples were determined on a BIO-TEK®Model EL340 Microplate reader. The amount of α-galactosides present in the samples were determined by comparison to known quantities of the stachyose standard. To facilitate the analysis of thousands of samples, enzymatic assays were replicated once. Lines that appeared to be low in raffinose saccharide content from the primary assay were subsequently reassayed n triplicate, beginning from the ground see, if sufficient material was available. Lines whose composition was confirmed in the secondary assay were grown to maturity under field conditions and seed from the field-grown plants were assayed again. In cases where more specific information about the raffinose saccharide profile (i.e. amounts of stachyose, raffinose, and galactinol) was required, low raffinose saccharide lines identified by the enzymatic assay were reassayed using the HPLC assay (described below).

To facilitate the rapid selection of low stachyose germplasm, a thin layer chromatography "TLC" assay was developed. For this assay, about 60 mg of ground seed powder was placed into a 13×100 mm screw top test tube, to which 1 ml of 4:3 (v/v) methanol:water and 1 ml of chloroform were added. The tubes were capped, placed in racks and mixed on a rotary shaker for 60 minutes at 25 rpm at room temperature. After extraction the tubes were centrifuged at 2100 rpm for 5 minutes. A 4 $\mu$L sample was taken from the methanol:water layer and placed on a 20×20 cm 'Baker' Silica Gel preadsorbent/channeled TLC plate with a 250 $\mu$m analytical layer. Samples were allowed to dry at room temperature and the plate was then placed in a TLC tank with a 3:4:4 (v/v/v) solution of Ethyl Acetate:Isopropanol:20% Acetic Acid (in water). The solution was allowed to soak up the analytical channels for 10 cm, at which time the plate was removed and allowed to air dry in a fume hood. The plate was then sprayed with an aniline-diphenylamine reagent to identify the carbohydrates in the sample. This reagent was prepared by mixing 1 ml of aniline with 100 mls of acetone, 1 gram of diphenylamine, and 10 mls of phosphoric acid. The plate was then placed in a 100° C. oven for 15 minutes to dry and removed and allowed to cool down before reading the analytical channels. Stachyose and raffinose content in the soybean samples were estimated by comparison to the elution pattern seen in pure standards. In addition, the TLC elution profile of experimental lines was compared to that that seen in lines previously identified as being homozygous for stc1x alleles by the enzymatic assay or the HPLC assay described below.

A high performance anion exchange chromatography/pulsed amperometric assay, referred to herein as the "HPLC" assay, was used for determining the content of individual raffinose saccharides (e.g., stachyose, raffinose, and galactinol) and for confirming the results of either the enzymatic or TLC assays. Conditions for the grinding and extraction of the seed were identical to those used for the previous "enzymatic" assay. A 750 μL aliquot of the aqueous phase was removed and dried under reduced pressure at 80° C. The dried material was then dissolved in 2 mL of water and mixed vigorously for 30 sec. A 100 μL aliquot was removed and diluted to 1 mL with water. The sample was mixed thoroughly again and then centrifuged for 3 min at 10,000×g. Following centrifugation, a 20 μL sample was analyzed on a Dionex™ PA1 column using 150 mM NaOH at 1.3 mL/min at room temperature. The Dionex™ PAD detector was used with E1=0.05 v, E2=0.60 v and E3=−0.60 v and an output range of 3 μA. Galactinol, glucose, fructose, sucrose, raffinose, stachyose and verbascose were well separated by the chromatographic conditions. The carbohydrate content of the samples was determined by comparison to authentic standards. Total raffinose saccharide content in μmol/g dry basis was determined from the following formula:

RSA=(2×STC)+RAF+GAL where:

STC=seed stachyose content in μmol/g dry basis

RAF=seed raffinose content in μmol/g dry basis

GAL=seed galactinol content in μmol/g dry basis

RSA=seed total raffinose saccharide content in μmol/g dry basis

The above abbreviations for stachyose, raffinose, galactinol, and total raffinose saccharide content are used within tables of this specification for brevity. Since stachyose contains two α-linked galactose residues, the calculated RSA value is a reflection of the total number of α-linked galactose residues present in samples as measured by the HPLC method described above. Although HPLC carbohydrate values are reported to the nearest whole number, total raffinose saccharide content was calculated using STC, RAF, and GAL values rounded off to the nearest tenth. Due to rounding error, RSA content reported in tables within this specification, may be slightly different than that calculated using the reported STC, RAF, and GAL whole numbers.

Results obtained from the carbohydrate analyses were subjected to analysis of variance using the software SuperA-NOVA (Abacus Concepts, Inc., 1984 Bonita Avenue, Berkeley, Calif. 94704). When appropriate, Fisher's Protected LSD was used as the post-hoc test for comparison of means. In other comparisons, means were considered statistically significant if the ranges defined by their standard errors (SEM's) did not overlap. In cases where raffinose saccharide means were being compared to the mean of a control line, a mean was considered significantly lower than that of the control if said mean was at least 3 standard deviations below that of the control mean.

Near Infrared Transmittance (NIT) Assay for Seed Protein Content

Seed protein content was determined nondestructively by Near Infrared Transmittance (NIT) using a Tekatur™ Model 1255 Food and Feed Analyzer (Tekatur A B, Box 70, S-263 21, Hoganas Sweden). The protein values used for the calibration equation were determined using the Kjeldahl digestion method (JAOAC (1976) 59:141). The calibration set included 75 soybean samples that ranged from 36.6% to 50.9% protein on a dry matter basis (db). Infratec Calibration Maker software (Infra-Maker: Produced for Tekatur A B by Camo, Norway) was used according to the manufacturer's protocol in the development of the calibration equation. Approximately 10 g of seed per line were used in the analysis.

Screening Soybean Germplasm for Improved Carbohydrate Composition

Using the above carbohydrate assays, a total of ca. 14,000 PI lines from the USDA Soybean Germplasm Collection were assayed for total α-galactoside content and/or total raffinose saccharides content. After primary and secondary enzymatic assays of PI lines, 25 lines (Table 3) were grown in the field to determine whether the low raffinose saccharide phenotype was heritable (expressed in subsequent generations). Of the original 25 PI selections that appeared to be low in raffinose saccharide phenotype, only the phenotype of LR28 was heritable. LR28 displayed the lowest total α-galactoside content after being grown again under field conditions (Table 3). In addition to the data provided in this example, the phenotype of LR28 was confirmed in several more environments (Examples 2 and 3). Presumably, the raffinose saccharide phenotypes of the other 24 PI selections were artifacts created by the age and storage conditions of the seeds assayed. For example, some of the candidates from the initial assays, particularly LR1 and LR2, had poor seed quality and poor germination ability compared to the other candidates. The low raffinose saccharide content of LR1 and LR2 in the initial screen was possibly due to the fact that the seed obtained from the UDSA for screening was old and had metabolized most of its carbohydrate reserves. Such selection artifacts typify the obstacles associated with the selection of lines that have genetic variation for low raffinose saccharide content. It is therefore essential that any germplasm source be regrown and reassayed before it can be confirmed as a heritable source of low raffinose saccharide content.

TABLE 3

Confirmation of LR28 as a Germplasm Source for Low Seed Soluble α-Galactoside Content

| Low Raffinose Saccharide Candidate | PI Identification Number | Secondary Screen Total α-Galactoside μmoles/g | Grown Again in Field Total α-Galactoside μmoles/g |
|---|---|---|---|
| LR1 | PI 416.815 | 71 | 159 |
| LR2 | PI 408.277 | 96 | 173 |
| LR3 | PI 408.310A | 111 | 158 |
| LR4 | PI 423.753A | 111 | 162 |
| LR5 | PI 408.123 | 115 | 159 |
| LR6 | PI 398.649 | 121 | 158 |
| LR7 | PI 408.105A | 121 | 185 |
| LR8 | PI 416.923 | 128 | 191 |
| LR9 | PI 404.159 | 136 | 196 |
| LR10 | PI 398.965 | 140 | 182 |
| LR11 | PI 399.073 | 145 | 157 |
| LR17 | PI 407.805A | 129 | 169 |
| LR18 | PI 407.888 | 122 | 169 |
| LR19 | PI 399.089 | 125 | 163 |
| LR20 | PI 407.921 | 140 | 185 |
| LR21 | PI 408.140B | 140 | 174 |
| LR24 | PI 227.558 | 135 | 208 |
| LR27 | PI 157.490 | 121 | 175 |
| LR28 | PI 200.508 | 93 | 117 |
| LR29 | PI 157.459 | 142 | 163 |
| LR30 | PI 248.512 | 117 | 210 |
| LR31 | PI 253.653 | 129 | 163 |
| LR32 | PI 290.114 | 133 | 192 |
| LR33 | PI OZZIE | 133 | 188 |
| LR34 | PI HAROSOY | 124 | 176 |

Superiority of LR28 to Previously Reported Germplasm

To investigate the novelty of the raffinose saccharide content of LR28, it was compared under identical analytical conditions to a series of elite check lines and to a series of PI lines that had been previously reported as being low in raffinose saccharide content [see Hymowitz, T. et al. Comm. In *Soil Science and Plant Analysis* (1972) 3:367–373, Hymowitz, T. et al. *Agronomy J.* (1972) 64:613–616, Hymowitz, T. and Collins, F. I *Agronomy J.* (1974) 66:239–240, Openshaw, S. J. and Hadley, H. H. *Crop Science* (1978) 18:581–584, Openshaw, S. J. and Hadley H. H *Crop Science* (1981) 21:805–808, and Saravitz (1986) Ph.D. Thesis, North Carolina State University, Horticultural Science Department].

Seeds of LR28, 8 elite check lines (A3205, Acme, Ajma, Altona, Bonus, Fiskeby, Norman, and Portage), and said previously reported PI's were assayed by the HPLC method for total raffinose saccharide content (Table 4). LR28 was substantially lower in total raffinose saccharide content than all elites lines and said previously reported lines of relevance that were tested. All but one of the previously reported PI lines fell within or above the range of total raffinose saccharide content of the elite check lines. The best of the previously reported PI's (PI203.246) was only 3 μmol/g lower in total raffinose saccharide content than the lowest of the elite check lines. All lines were clearly inferior to LR28 which was 47 μmol/g lower in total raffinose saccharide content than the best elite check line. In fact, most of the previously reported PI lines were actually higher in raffinose saccharide content than the range defined by the elite checks. This demonstrates the lack of repeatability of prior attempts to identify low raffinose saccharide germplasm.

When the stachyose content of LR28 was compared to that of the other lines (Table 4), it was quite convincing that LR28 is a truly unique germplasm line. The stachyose content of LR28 was 55% lower than the next lowest line (PI203.246) and approximately 65% lower than the average stachyose content of the elite check lines. This is relevant since stachyose is the most abundant of the raffinose saccharides present in soybeans and is thought to be the most undesirable from a nutritional standpoint [Cristofaro et al. (1974) in Sugars in Nutrition, Ch 20, 313–335].

TABLE 4

Comparison of the Carbohydrate Composition of LR28 With Elite Check Lines and PI's That Have Been Suggested as Germplasm With Low Raffinose Saccharide Content

| Line | RSA | STC | RAF | GAL |
| --- | --- | --- | --- | --- |
| LR28 | 115 | 28 | 8 | 51 |
| A3205 | 162 | 73 | 17 | 0 |
| ACME | 183 | 77 | 30 | 0 |
| AJMA | 185 | 80 | 24 | 0 |
| ALTONA | 182 | 80 | 23 | 0 |
| BONUS | 183 | 81 | 20 | 0 |
| FISKEBY | 192 | 86 | 20 | 0 |
| NORMAN | 186 | 81 | 24 | 0 |
| PORTAGE | 193 | 85 | 23 | 0 |
| PI79.593 | 211 | 89 | 24 | 8 |
| PI79.727 | 177 | 80 | 13 | 3 |
| PI80.488-1 | 206 | 90 | 20 | 6 |
| PI81.761MD | 201 | 89 | 23 | 0 |
| PI81.761YD | 186 | 81 | 25 | 0 |
| PI81.763 | 195 | 87 | 19 | 3 |
| PI81.766 | 228 | 101 | 20 | 7 |
| PI81.768 | 202 | 92 | 18 | 0 |
| PI81.770 | 206 | 94 | 16 | 3 |
| PI81.771 | 204 | 92 | 18 | 1 |
| PI81.772 | 194 | 88 | 14 | 4 |
| PI81.773 | 232 | 104 | 20 | 3 |
| PI81.785 | 237 | 102 | 25 | 8 |
| PI86.002 | 272 | 121 | 25 | 6 |
| PI86.046 | 247 | 109 | 23 | 5 |
| PI135.624 | 212 | 91 | 24 | 6 |
| PI153.292 | 213 | 94 | 25 | 1 |
| PI163.453 | 217 | 96 | 25 | 0 |
| PI189.950 | 238 | 109 | 17 | 5 |
| PI203.246 | 159 | 62 | 17 | 28 |
| PI232.987 | 249 | 112 | 23 | 1 |

TABLE 4-continued

Comparison of the Carbohydrate Composition of LR28 With Elite Check Lines and PI's That Have Been Suggested as Germplasm With Low Raffinose Saccharide Content

| Line | RSA | STC | RAF | GAL |
| --- | --- | --- | --- | --- |
| PI232.989 | 254 | 116 | 21 | 0 |
| PI232.991 | 299 | 134 | 26 | 5 |
| PI326.581 | 198 | 86 | 16 | 10 |
| PI339.731 | 178 | 77 | 21 | 3 |
| PI342.434 | 184 | 83 | 18 | 0 |
| PI361.123A | 188 | 82 | 24 | 0 |
| PI361.123B | 183 | 81 | 22 | 0 |

Inheritance of the Improved Carbohydrate Composition of LR28

To study the inheritance of the low raffinose saccharide phenotype of LR28, the line was crossed with four different elite lines. The four elite lines used were A4715 (Asgrow Seed Co. elite line), X3337 (Asgrow Seed Co. elite line), ST9025 (E. I. du Pont de Nemours and Company elite line), and ST9026 (E. I. du Pont de Nemours and Company elite line). F1 seeds were grown in the greenhouse and allowed to self-pollinate. The resulting F2 seeds were then planted in Isabela, Puerto Rico during the winter of 1991 (the "IP91" environment) and the resultant F2 plants allowed to self-pollinate. F3 seeds derived from individual F2 plants (F2:3 seeds) were assayed for total α-galactoside content using the enzymatic method described in Example 1. Total α-galactoside content was used to score F2 lines for Mendelian genetic segregation studies.

Figure 1B:
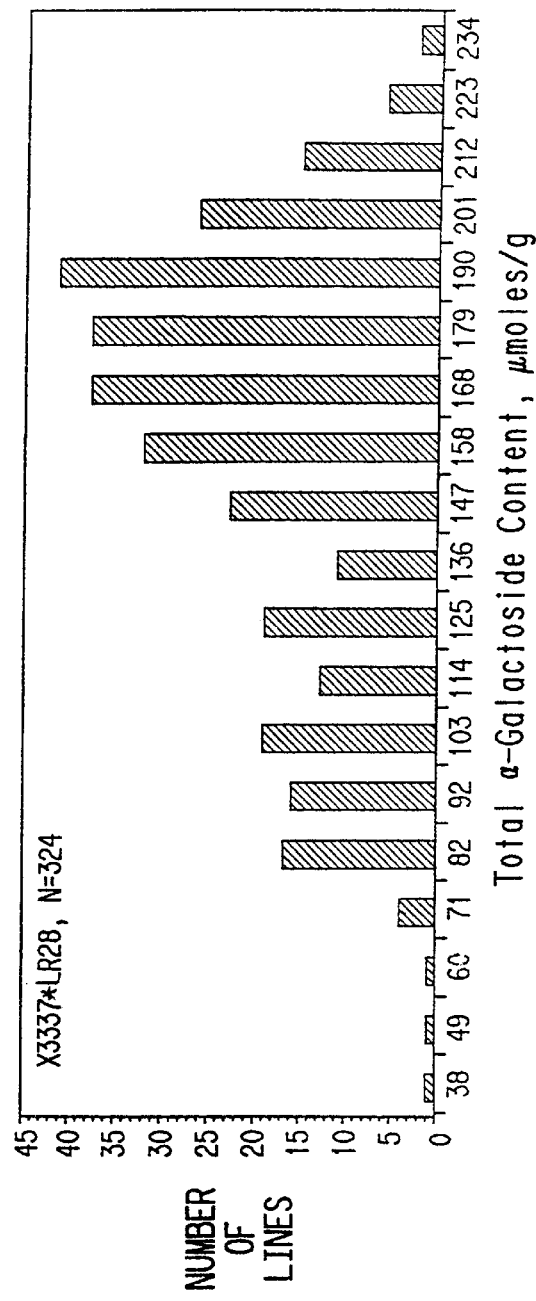
Figure 1C:
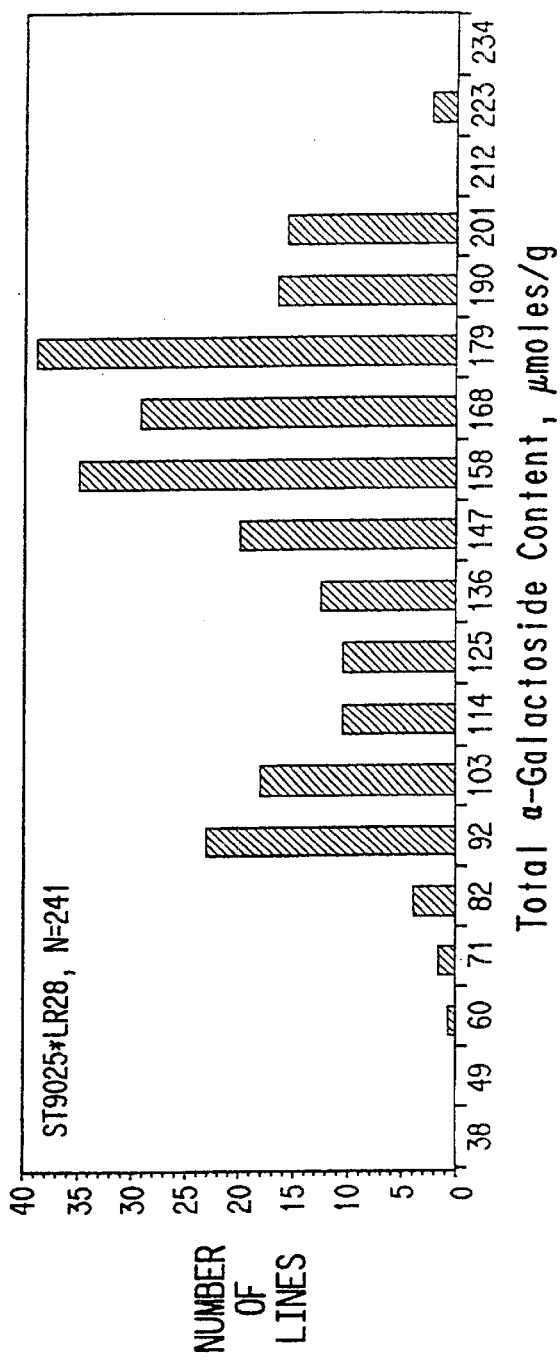
Figure 1D:
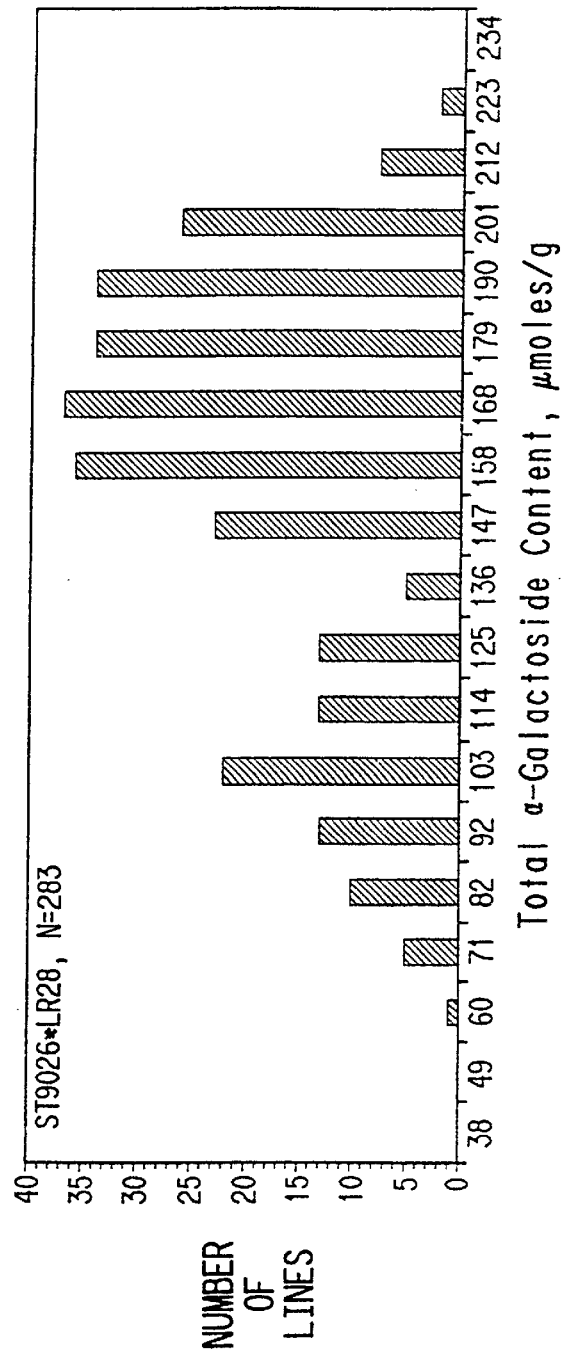

Segregation for total α-galactoside content in all four elite*LR28 crosses (FIGS. 1A–D) followed a bimodal distribution in which the F2 lines could be grouped into one of two discrete classes: those with seed containing less than 120 μmol/g of total α-galactoside ("low" class) and those with seed containing more than 120 μmol/g total α-galactoside (the "high" class). The low class included the range of α-galactoside levels normally observed among single plants of parent LR28. The high class included the range of α-galactoside contents previously observed among single plants of conventional lines and also included the intermediate range of α-galactoside levels that would be expected for lines derived from F2 plants that were heterozygous for any gene(s) conferring low raffinose saccharide content. In all four F2 populations, the ratio of low to high F2 lines was not significantly different than a ratio of 1 to 3 when subjected to $\chi^2$ analysis (Table 5). Since the range of intermediate phenotypes indicative of heterozygous plants was continuous with the remainder of the high class, low raffinose saccharide content is either recessive or codominant in terms of gene action. Segregation between the high and low class was consistent with segregation of two alleles at a single locus where the allele from the conventional lines, herein named "Stc1" (after stachyose), confers high (conventional) raffinose saccharide content and the allele from LR28, herein named "stc1a", confers the low raffinose saccharide phenotype. Results indicate that stc1a must be in the homozygous condition for full expression of the low raffinose saccharide phenotype. The fact that the stc1a homozygotes can be distinguished from heterozygotes (as indicated by a relatively quick enzymatic assay) is of particular importance for breeding applications. This ensures that lines selected below an appropriately low raffinose saccharide threshold will be fixed (in the homozygous condition) for the stc1a allele. Due to the indication that intermediate phenotypes represent heterozygous individuals, it should also be possible to predictably select heterozygous individuals when necessary in certain breeding applications. The predictable inheritance of stc1a will greatly facilitate its transfer into elite lines through conventional breeding techniques. Since all four crosses resulted in the production of low raffinose saccharide segregants, it is believed that the gene will be useful in any genetic background for improving the carbohydrate composition of the seed. Going far beyond previous attempts, Inventors have disovered the only known heritable source of low seed raffinose saccharide content and have characterized the inheritance of the low raffinose saccharide trait.

TABLE 5

Segregation for Raffinose Saccharide Content in Four Elite*LR28 F2 Populations

| Cross | F2 Segregation Class | | $\chi^2$ for 1:3 Ratio | Statistical Significance |
|---|---|---|---|---|
| | "low" | "high" | | |
| A4715*LR28 | 66 | 165 | 1.57 | ns |
| X3337*LR28 | 72 | 252 | 1.33 | ns |
| ST9025*LR28 | 59 | 182 | 0.03 | ns |
| ST9026*LR28 | 65 | 218 | 0.62 | ns |

Development of Lines with Low Raffinose Saccharide Content in Combination with Other Valuable Seed and Agronomic Traits In crosses X3337*LR28, A4715*LR28, ST9025*LR28, and ST9026*LR28, protein content among the individual F2 lines with a total raffinose saccharide content less than 120 $\mu$mol/g ranged from about 41% to greater than 48%. This exceeds the range of protein content observed among plants within the elite lines A4715 (42.7% to 44.7% range) and X3337 (41.1% to 42.6% range) that were grown in the same environment as the F2 lines. LR28 had apparently contributed genes for high protein in addition to stc1a. The correlation between total $\alpha$-galactoside content and protein content within each of the four segregating F2 populations were as follows: $R2=0.029$, 0.000, 0.014, and 0.004 for the crosses A4715*LR28, X3337*LR28, ST9025*LR28, and ST9026*LR28, respectively. None of these correlations were statistically significant. This is good evidence that there is no association between protein content and the stc1a allele. Although there was no association between raffinose saccharide content and protein content, many F2 lines with both low raffinose saccharide content and high protein content (up to 48%) were observed in the elite*LR28 F2 populations. Therefore, it is possible to develop lines with both low raffinose saccharide content and high protein content.

If the instant low raffinose saccharide germplasm is crossed with germplasm sources containing other desirable traits, it is expected that a fraction of the resultant progeny will inherit low raffinose saccharide content in combination with the desirable trait(s) from other said germplasm sources. Desirable seed traits that will be combined with low raffinose saccharide content include (but are not limited to) high protein content, high methionine content, high lysine content, high oleic acid content, high stearic acid content, low palmitic acid content, low linoleic acid content, low linolenic acid content, lipoxygenase nulls, and trypsin inhibitor nulls. It is also expected that the instant low raffinose saccharide germplasm will be combined with any trait of argonomic significance to develop elite lines. Examples of such agronomic traits include (but are not limited to) emergence vigor, seedling vigor, vegetative vigor, disease resistance, pest resistance, herbicide resistance, drought resistance, lodging resistance, and high seed yield.

Example 2

Creation of Mutant Genes Conferring Improved Carbohydrate Composition

Mutagenesis and Selection of Mutants

A number of soybean lines were treated with a chemical mutagen, NMU (N-nitroso-N-methylurea), in an attempt to induce mutations that lower the raffinose saccharide content of soybean seeds. Lines treated included the elite lines Williams 82 and A2543, USDA germplasm lines A5 and N85-2176, and LR13. LR13 was originally a putative mutant of Williams 82 but did not confirm as being significantly lower in raffinose saccharide content than Williams 82 in subsequent tests. The following protocol for the mutagenesis of LR13 is representative of the method by which the above lines were treated with NMU and advanced through subsequent generations to obtain populations that could be screened for low raffinose saccharide mutations.

Approximately 130,000 seeds (22.7 kg) of LR13 (a line essentially identical to Williams 82) were soaked in 150 L of tap water under continuous aeration for 8 hours. Aeration was accomplished by pumping air through standard aquarium "airstones" placed in the bottom of the soaking vessel. Imbibed seeds were drained and transferred to 98 L of a 2.5 mM N-nitroso-N-methylurea (NMU) solution buffered at pH 5.5 with 0.1M phosphate buffer under continuous aeration. Seeds remained in the NMU solution for 3 h and were then put through a series of rinses to leach out the remaining NMU. For the first rinse, treated seeds were transferred to 45 L of tap water for 1 min. For the second rinse, seeds were transferred to 45 L of fresh tap water under continuous aeration for 1 h. For the third rinse, seeds were transferred to 45 L of fresh tap water under continuous aeration for 2 h. For the fourth rinse, seeds were transferred to 45 L of fresh tap water under continuous aeration. One half of the seeds were removed from the fourth rinse after 2 h (sub-population 1) while the other half of the seeds were removed from the fourth rinse after 5 h (sub-population 2). After removal from the fourth rinse, seeds were drained of exogenous water and spread out on cardboard sheets to dry off in the sun for 1 h. The imbibed M1 seeds were then field planted (Isabela, Puerto Rico, U.S.A.) in rows spaced 46 cm apart at a density of approximately 14 seeds per foot within the rows and a depth of 2.5 cm.

Two pools of M2 seeds (from sub-populations 1 and 2) were harvested in bulk from the M1 plants. Approximately 40,000 M2 seeds from sub-population 1 and 52,000 M2 seeds from sub-population 2 were planted at Isabela, Puerto Rico, U.S.A. Within each sub-population, 5 pods from each of 3,000 M2 plants were harvested and bulked to obtain a bulk M3 seed population. M3 bulks were planted at Isabela, Puerto Rico. At maturity, seed from 5000 M3 plants were harvested individually to obtain 5000 M3:4 lines from each sub-population.

During the winter of 1991, a total of at least 8,000 M3:4 lines were screened to measure the content of raffinose saccharides using the enzymatic method described in Example 1. Two M3:4 lines, LR484 and LR33 (derived from the LR13 mutagenesis), were selected as having a lower raffinose saccharide content than elite soybean lines.

In the spring of 1991, M3:4 seeds of LR484 and LR33 were planted at the DuPont Stine Research Farm in Newark, Del., U.S.A. (the "ST91" environment) along with LR28 and elite control lines. In the fall of 1991, the M4:5 seeds harvested from individual plants of LR484, LR33, and control lines were assayed by the HPLC method for carbohydrate content.

During the winter of 1992, additional enzymatic screening of M3:4 lines of LR13 resulted in the selection of several new putative routants including LR3705 and LR4271. After growing single plants of LR3705 and LR4271 in the IP92 environment and confirming their low raffinose saccharide content by HPLC analysis (Table 6), seeds of LR3705 and LR4271 were planted in the spring of 1992 and 1993 at the higher in stachyose content than LR28 but lower in galactinol in all environments tested. Because of this trade-off between stachyose and galactinol, LR484 was very comparable to LR28 in terms of total raffinose saccharide content. Since LR484 contains a mutation that is allelic with the stc1a gene from LR28 (see data later in this example), it is highly possible that the subtle differences between LR484 and LR28 are due to minor genes (independent of stc1x) within the different genetic backgrounds of the two lines.

TABLE 6

Isabela PR Newark, Delaware
HPLC Carbohydrate Phenotypes For Mutant Lines and Checks Grown in 1991, 1992 and 1993

| YEAR | PED | GEN1 | N | STC | RAF | GAL | RSA | GEN2 | N | PLOT | STC | RAF | GAL | RSA | | SSDV |
|---|---|---|---|---|---|---|---|---|---|---|---|---|---|---|---|---|
| | | | | | | | | | | ST91 Environment | | | | | | |
| 91 | A3205 | | | | | | | ELIT | 9 | ST91-37 | 68 | 17 | 0 | 153 | | 10.2 |
| 91 | A3322 | | | | | | | ELIT | 8 | ST91-35 | 102 | 21 | 0 | 225 | | 10.7 |
| 91 | A4715 | | | | | | | ELIT | 9 | ST91-19 | 108 | 18 | 5 | 236 | | 9.3 |
| 91 | LR28 | | | | | | | GR90 | 38 | ST91-82 | 22 | 5 | 50 | 98 | low1 | 2.5 |
| 91 | LR484 | | | | | | | GR91 | 9 | ST91-84 | 27 | 3 | 13 | 69 | low1 | 3.3 |
| 91 | LR33 | | | | | | | GR91 | 8 | ST91-83 | 61 | 18 | 0 | 140 | | 6.5 |
| | | | IP92 Environment | | | | | | | ST92 Environment | | | | | | |
| 92 | A1923 | ELIT | | | | | | ELIT | 5 | ST92-29 | 60 | 12 | 0 | 131 | | 3.6 |
| 92 | A1929 | ELIT | | | | | | ELIT | 5 | ST92-30 | 65 | 11 | 0 | 141 | | 9.2 |
| 92 | A2396 | ELIT | | | | | | ELIT | 10 | ST92-28 | 71 | 12 | 0 | 154 | | 7.9 |
| 92 | A3205 | ELIT | | | | | | ELIT | 5 | ST92-100 | 63 | 12 | 0 | 138 | | 9.2 |
| 92 | A3322 | ELIT | 10 | 84 | 17 | 0 | 186 | ELIT | 10 | ST92-15 | 78 | 14 | 0 | 170 | | 2.8 |
| 92 | A4715 | ELIT | | | | | | ELIT | 5 | ST92-6 | 68 | 8 | 0 | 145 | | 5.8 |
| 92 | LR3705 | GR90 | 5 | 16 | 2 | 27 | 59 | GR90 | 20 | 4 PLOTS | 24 | 3 | 27 | 77 | low1 | 4.5 |
| 92 | LR484 | GR91 | 5 | 22 | 3 | 13 | 61 | GR91 | 18 | 4 PLOTS | 32 | 4 | 16 | 84 | low1 | 3.8 |
| 92 | LR3705 | GR92 | 1 | 41 | 4 | 0 | 86 | GR92 | 1 | ST92-80 | 33 | 4 | 16 | 85 | low1 | |
| 92 | LR4271 | GR92 | 1 | 40 | 4 | 0 | 85 | GR92 | 5 | ST92-79 | 34 | 5 | 11 | 83 | low1 | 15.9 |
| | | | IP93 Environment | | | | | | | ST93 Environment | | | | | | |
| 93 | A1923 | ELIT | | | | | | ELIT | 8 | ST93-208 | 69 | 19 | 0 | 156 | | 3.4 |
| 93 | A1929 | ELIT | | | | | | ELIT | 8 | ST93-204 | 75 | 17 | 0 | 167 | | 4.8 |
| 93 | A2396 | ELIT | | | | | | ELIT | 8 | ST93-212 | 76 | 19 | 0 | 171 | | 3.4 |
| 93 | A3322 | ELIT | | | | | | ELIT | 8 | ST93-224 | 84 | 16 | 0 | 184 | | 2.0 |
| 93 | A4715 | ELIT | | | | | | ELIT | 8 | ST93-232 | 78 | 12 | 0 | 167 | | 7.1 |
| 93 | WILLIAMS82 | ELIT | | | | | | ELIT | 8 | ST93-228 | 72 | 13 | 0 | 156 | | 7.6 |
| 93 | LR28 | GR90 | 5 | 14 | 2 | 18 | 48 | GR90 | 20 | 5 PLOTS | 19 | 4 | 21 | 62 | low1 | 2.2 |
| 93 | LR484 | GR91 | 9 | 17 | 2 | 13 | 49 | GR91 | 18 | 5 PLOTS | 27 | 4 | 12 | 69 | low1 | 8.1 |
| 93 | LR3705 | GR92 | 5 | 30 | 4 | 4 | 69 | GR92 | 10 | 5 PLOTS | 47 | 7 | 7 | 108 | low1 | 4.4 |
| 93 | LR4271 | GR92 | 10 | 21 | 3 | 5 | 50 | GR92 | 20 | 10 PLOTS | 32 | 5 | 9 | 78 | low1 | 5.8 |

GRN1 = 1st Generation grown in the year listed.
GEN2 = 2nd Generation grown in the year listed.
ElIT = Elite control line
GR90 = Germplasm line selected in 1990
GR91 = Germplasm line selected in 1991
GR92 = Germplasm line selected in 1992

DuPont Stine Research Farm in Newark Del. U.S.A. (the "ST92" and "ST9" environments, respectively) side-by-side with elite control lines and low raffinose saccharide control lines LR28 and LR484. Seeds from single plants of LR3705, LR4271, and control lines from the ST92 and ST93 environments were analyzed by HPLC to confirm their low raffinose saccharide content in an environment typical of commercial soybean production.

Results from 5 different enviroments (Table 6), 3 of which are typical of commercial soybean production, confirm that mutant line LR484 produces dramatically less stachyose, raffinose, and total raffinose saccharide content than elite lines. These results alone indicate that LR484 contains heritable genetic variation for low raffinose saccharide content. The differences in carbohydrate profile between LR484 and LR28 were relatively minor compared to the differences between LR484 and the elite lines. LR484 was slightly A deposit of soybean seed designated LR484, was deposited on Oct. 15, 1992 with the American Type Culture Collection, 12301 Parklawn Drive, Rockville, Md., U.S.A., 20851, and assigned the accession number ATCC 75325. The deposit was made under terms of the Budapest Treaty.

LR33 proved to be lower in raffinose saccharides than the elite check lines in ST91 but not nearly as low as either LR28 or LR484. Because of this, LR33 was not pursued as a source of major genes for raffinose saccharide content. However, Inventors did pursue LR33 as a potential source of modifier gene(s) (see Example 3).

The low raffinose saccharide phenotypes (Table 6) of mutants LR3705 and LR4271 confirmed in all 4 environments tested, 2 of which (ST92 and ST93) are typical of commericial soybean production. LR4271 had approximately one half of the stachyose and one third of the raffinose of conventional elite controls. Although this was offset by an increase in galactinol, the total raffinose saccharide content of LR4271 was approximately one half that of conventional elite control lines when grown in environments typical of commercial soybean production. Although LR3705 was comparable to LR4271 in the ST92 environment, its stachyose content was slightly higher in the ST93 environment. Both mutants were significantly lower in raffinose saccharide content than the elite lines. These data provide conclusive evidence that LR3705 and LR4271 contain major genes that reduce raffinose saccharide content. Inventors, therefore, provide two more examples of induced mutations that dramatically reduce the heritable raffinose saccharide content of soybean seeds.

Based on 41 replicated HPLC measurements (each an average of 4 to 10 plants) within this specification, the following observations have been made: (a) when allowed to reach full maturity in an environment typical of commercial soybean production, the typical seed stachyose content of conventional soybean lines was 60 to 80 $\mu$mol/g db with a minimum of 50 $\mu$mol/g db; and (b) when allowed to reach full maturity in an environment typical of commercial soybean production, the typical seed total raffinose saccharide content of conventional soybean lines was 130 to 170 $\mu$mol/g db with a minimum of 120 $\mu$mol/g db. When produced in the same environments, seeds of LR28, LR484, LR4271, and LR3705 were clearly superior to seeds of conventional lines in terms of their low raffinose saccharide phenotype.

Allelism Test and Discovery of Gene stc1b

During the summer of 1991 in Newark, Del., LR484 was crossed with LR28 to determine if the mutation conferring low raffinose saccharide content in LR484 was allelic to stc1a. F1 seeds of the cross LR28*LR484 were harvested in early September of 1991 and planted in the greenhouse to produce F2 seeds that were harvested in December of 1991. After harvest, F2 seeds were promptly shipped to and planted in Isabela, Puerto Rico along with parental check seeds of LR28, LR484, and a conventional line A3322, used as an experimental control. F2-derived F3 seeds (F2:3 seeds) from each F2 plant and seeds from parental check plants were harvested in early 1992 from the IP92 environment and used for the allelism study. Seeds from F2 and check plants were assayed for total $\alpha$-galactoside content by the enzymatic method described in Example 1.

If the mutation in LR484 is allelic with the stc1a allele from LR28, one would expect no segregation among F2 progeny from the LR28*LR484 cross. In addition, one would expect all such F2 plants to produce seeds with low raffinose saccharide content (within the range of the parent lines). If LR484 and LR28 contained nonallelic and independently segregating genes for low raffinose saccharide content, one would expect at least some recombinant F2 plants that produce seed with normal (high) raffinose saccharide content.

The unimodal distribution of F2 phenotypes from the LR28*LR484 cross (FIG. 2) clustered around a mean total $\alpha$-galactoside content of ca. 98 $\mu$mol/g and covered a range of ca. 45 $\mu$mol/g to 145 $\mu$mol/g. This range was consistent with the range displayed by stc1a homozygotes from the elite*LR28 crosses (the "low" mode of the bimodal phenotypic distributions of FIGS. 1A–D). None of the F2 plants produced seed that were in the $\alpha$-galactoside range of normal soybean plants (the elite line A3322 had a mean $\alpha$-galactose content of 208±10 in the same IP92 environment). Results from the LR28*LR484 cross are therefore consistent with a lack of segregation at the Stc1 locus. This indicates that LR484 and LR28 contain allelic genes that both confer the low raffinose saccharide phenotype. The allele in LR484 conferring low raffinose saccharide is herein named "stc1b". Although the check plants of LR484 and LR28 were all low in $\alpha$-galactoside content, LR484 plants were slightly higher in $\alpha$-galactoside content than LR28 (FIG. 2). As discussed previously, when LR484 and LR28 were compared in 5 different environments using the more informative HPLC analysis (Table 6), small differences in phenotype were also observed. These small differences between LR484 and LR28 may be either a consequence of genetic background differences that modify stc1x expression or a difference between the stc1a and stc1b in terms of gene action. The phenotypic range of stc1x homozygotes from the cross LR28*LR484 exceeds the range displayed among plants of the inbred stc1x parent lines (FIG. 2). This is likely due to the fact that more F2 than parental plants were sampled or due to the segregation of background genes (independent of stc1x) that have a minor effect on raffinose saccharide content compared to the effect of the stc1x genes. In the case of the LR28*LR484 cross, the parental lines would be more or less homogeneous (nonsegregating) for said background genes and would, therefore, not dislay within-line segregation for said background genes. The fact that all of the segregants from the cross between LR28 and LR484 were well below the phenotypic range displayed by the conventional check line is clear evidence that LR28 and LR484 contain allelic genes that dramatically reduce raffinose saccharide content.

The discovery of LR28 and LR484 have taught the importance of the Stc1 locus in terms of its control on raffinose saccharide accumulation in soybean seeds. Despite the failure of previous attempts, the Inventors have taught that variation at the Stc1 locus can be obtained through screening germplasm or through mutagenesis. Instant stc1x alleles can be used to dramatically reduce the inherent raffinose saccharide content of soybean seeds.

Example 3

Evidence for Genetic Modifiers of stc1x

Enzymatic analysis of segregating F2-derived lines from the crosses X3337*LR28 and A4715*LR28 (FIG. 1 of Example 1) indicated that these two crosses yielded segregants that were lower in total raffinose saccharide content than that observed for LR28 or segregants from crosses ST9025*LR28 and ST9026*LR28. This was the first observation to suggest that X3337 and A4715 contained genetic elements that, when combined with the stc1x genes, enhance the expression of stc1x to further reduce raffinose saccharide content. However, Inventors cite several reasons to further confirm the existence of such genetic modifiers of stc1x: (a) since stc1x drastically reduces the raffinose saccharide content, further reductions in raffinose saccharide content require more precision to establish statistical significance; (b) since F2 segregation data is based on single (unreplicated) plants that are highly heterozygous, it is difficult to identify F2 plants that are homozygous for both stc1x and relevant modifier gene(s) without a replicated progeny test of said F2 plants; (c) although tropical environments have proven to be useful for the selection of heritable seed traits including the instant low raffinose saccharide germplasm, claims about the phenotypic affect of modifiers of stc1x should be based on seed production in an environment typical of commercial soybean production.

For the aforementioned reasons, Inventors have established the following 7 step "modifier discovery procedure" to discover and confirm the existence of modifier genes that enhance the expression of major genes such as stc1x. This procedure can also be used to discover and confirm modifiers that affect any trait of interest. The method comprises:

1) crossing germplasm lines of any type with unmodified stc1x lines to obtain F1 progeny,
2) self pollinating said F1 progeny for one or more generations to obtain a population of segregating inbred lines,
3) planting said segregating lines in one environment and measuring the raffinose saccharide content of seed produced by each line in that environment,
4) selecting lines from step 3 with lower raffinose saccharide content than unmodified stc1x lines,
5) growing replicated plants of selected lines side-by-side with replicated plants of unmodified stc1x control lines in a second environment that approximates commercial soybean production conditions,
6) measuring the raffinose saccharide content of seed produced by replicated plants of each line grown in said second environment, and
7) using phenotypes from the second environment to identify lines that are inherently and significantly lower in seed raffinose saccharide content than the unmodified stc1x check lines.

Genetic Modifiers of stc1x that Further Reduce Stachyose Content

In Example 1, steps 1 through 3 of the modifier discovery procedure were completed to study the inheritance of the low raffinose saccharide trait of LR28. Steps 4 through 7 of the modifier discovery procedure were performed to confirm the heritability of F2 segregants that were unexpectedly lower in raffinose saccharide content than LR28. HPLC analysis was performed on the F2:3 lines of pedigree X3337*LR28, A4715*LR28, ST9025*LR28, and ST9026*LR28 from the IP91 environment that were lowest in α-galactoside content (enzymatic assay from Example 1). These F2:3 lines represent the class of segregants that are homozygous for the stc1a allele from parent LR28. The HPLC analysis, which is more informative than the enzymatic assay, provided a measure the actual components of the α-galacoside pool (stachyose, raffinose, and galactinol). Selected F2:3 lines from the HPLC analysis were then retested in the F3 generation (to produce F3:4 seed) in 1991 at the DuPont Stine Research Farm in Newark, Del. U.S.A. (the "ST91" environment). Since Delaware is a major region of commercial soybean production, the DuPont Stine Research Farm is quite representative of an environment used for commercial soybean production. Seeds of three conventional soybean lines (A3205, A3322, and A4715) and the unmodified stc1x lines LR28 and LR484 were planted within the same ST91 environment for a side-by-side comparison. In the fall of 1991, at least three (and usually five) F3 plants from each line where harvested from the ST91 environment when the plants had reached full maturity. The HPLC method was used to determine the carboydrate profiles of seeds from each plant. The carbohydrate profiles of the F3:4 progeny of a given F2-derived line were then averaged to get a replicated measure of the phenotype of each F2-derived line. This F3:4 average was used to confirm the phenotype of each line in an environment (ST91) typical of commercial soybean production.

Table 7 shows both the individual F2:3 phenotypes from the IP91 environment and the average F3:4 phenotypes from the ST91 environment. ST91 phenotypes of conventional elite check lines and the unmodified stc1x line LR28 are included in the same Table. "SELECTION" is the specific identity of a segregant in the form of (environment)-(plot number)-(plant number) from the environment where the segregant was originally produced and selected. "N" refers to the number of plants used to the obtain the average phenotype of a line in a given environment. "GEN1" refers to the generation of seeds that were produced in the Puerto Rico environment (step 3 of modifier discovery procedure) while "GEN2" refers to the generation of seeds that were produced in the commercial production environment (step 6 of the modifier discovery procedure). The profile from the commericial production environment is therefore a replicated F3 measure of the phenotype of the single F2 plant selected in the previous generation. A generation of "ELIT" refers to an elite check line. A generation of "GR90" or "GR91" refers to a germplasm line discovered in the year 1990 or 1991, respectively. Table 7 is sorted by generation, then by pedigree, and then by the mean stachyose content of lines grown in the ST91 environment. Data in subsequent examples are arranged in a similar fashion.

Based on a mean of 38 plants in the ST91 environment, the unmodified stc1x check line LR28 had a mean stachyose content of 22±2.5 μmol/g of dry seed. F3:4 lines with a mean stachyose content three standard deviations below that of LR28 (i.e. less than 15 μmol/g stachyose) were considered to be statistically superior to LR28 in terms of their low stachyose phenotype.

Out of 29 F2-derived stc1a lines from the pedigree X3337*LR28, 9 lines had a stachyose content that was significantly less than that of LR28 when grown in replicate in the ST91 environment (see lines designated as "low2" in Table 7). In addition, the average total raffinose saccharide content of these 9 lines was 65 μmol/g compared to 98 μmol/g for LR28. This is conclusive evidence that X3337 contains modifier gene(s) that enhance the expression of stc1a. Since a fairly high proportion (9 out of 29) of the stc1a lines from pedigree X3337*LR28 were significantly better than LR28, it appears that X3337 contains at least one modifier gene with a rather large effect. Since there is quantitative variation among the 9 lines in phenotype, it is difficult to deduce the exact Mendelian genetics of the modifier gene(s) present in X3337. However, the statistical difference between these lines and LR28 is sufficient to prove the heritability of the improved raffinose saccharide phenotype. With the discovery and confirmation of the first modifier(s) of stc1x, the term "low1" has been created to denote the low seed raffinose saccharide phenotype of unmodified stc1x lines such as LR28, and the term "low2" to denote the low seed raffinose saccharide phenotype of stc1x lines that have a significantly lower stachyose content than unmodified stc1x lines when produced in a common environment. Based on experience with several germplasm*LR28 crosses that yield low2 segregants (below), Inventors have outlined the typical phenotypic range for low2 phenotypes (Detailed Description of the Invention).

A4715 also proved to contain genetic modifier(s) of the stc1a gene. From the pedigree A4715*LR28, 7 out of 23 F2-derived lines were significantly lower than LR28 in stachyose content in the ST91 environment. These 7 lines also had an average total raffinose saccharide content of 53 μmol/g compared to 98 μmol/g for LR28. The phenotype of these modified stc1a lines were similar to those of the X3337*LR28 pedigree and is also referred to as a "low2" phenotype (Table 7).

Only 1 line (IP91-3-036) out of the 35 selected lines from pedigree ST9025*LR28 proved to be lower in stachyose content than LR28 when grown in the ST91 environment. Since plenty of low2 lines were obtained from the X3337*LR28 and A4715*LR28 pedigrees, IP91-3-036 was not advanced for further testing. Since the low2 segregant from the ST9025*LR28 cross was a rare segregant, ST9025 appears to be a less desirable source of stc1x modifiers than X3337 or A4715.

None of the 36 selected lines from the pedigree ST9026*LR28 proved to be lower in stachyose content than LR28 when grown in the ST91 environment. This is conclusive evidence that ST9026 does not contain genetic modifiers of the stc1a gene.

The instant modifier discovery procedure was used to determine whether elite lines A2396, A3322, and A5843 contain modifiers of stc1x genes. In the summer of 1992, A2396, A3322, and A5843 were crossed with unmodified stc1x lines derived from the pedigree A3322*LR484 to produce F1 seeds of pedigrees A2396*(A3322*LR484), A3322(2)*LR484, and (A3322*LR484)*A5843, respectively. F1 plants from these three pedigrees were grown in the greenhouse to produce segregating F2 progeny that were planted in Puerto Rico during the winter of 1993 (the "IP93" environment). Seeds of the unmodified stc1x check lines LR28 and LR484 were planted in the IP93 environment as well. In the spring of 1993, F2:3 seeds were harvested from each F2 plant and samples of each F2:3 line were screened for the stc1b gene using the TLC procedure as a preliminary screen. Selections from the TLC screen were then advanced to the more informative HPLC analysis so that the complete raffinose saccharide profile could be determined. F2:3 selections from the IP93 environment along with conventional elite lines, unmodified stc1x lines, and a confirmed low2 selection from X3337*LR28 were planted in the spring of 1993 at the DuPont Stine Research Farm in Newark, Del. U.S.A. (the "ST93" environment). Seeds from individual plants grown in the ST93 environment were assayed by HPLC to determine their total raffinose saccharide content. F3:4 seed from 3 to 10 F3 plants was used to calculate the mean phenotype of each line that was produced in an environment typical of commercial soybean production (ST93).

Although LR28 and LR484 were comparable in terms of total raffinose saccharide content, LR28 had a lower mean seed stachyose content than that of LR484 (Table 8). For this reason, the stachyose phenotype of LR28 (19±2.2) was used as the basis for comparison to unmodified stc1x lines in the ST93 environment. Using three standard deviations below the phenotype of LR28 as the cutoff, all lines with a mean seed stachyose content of less than 13 $\mu$mol/g were considered to be inherently superior to unmodified stc1x check lines in terms of low seed stachyose content.

Out of the seven tested lines of pedigree (A3322*LR484) *A5843, five had a significantly lower stachyose content than stc1x check line LR28 (designated as "low2" in Table 8). The raffinose saccharide profile of the best selections from pedigree (A3322*LR484)*A5843 was similar to that of the low2 check line from the pedigree X3337*LR28 that were grown in the same ST92 environment. Low2 selection had both lower stachyose and lower total raffinose saccharide content than the unmodified stc1x controls. This is conclusive evidence that A5843 contains modifier(s) genes that complement stc1x to further reduce stachyose content to produce the low2 phenotype. This is also conclusive evidence that the low raffinose saccharide phenotype conferred by stc1 can be enhanced with modifier gene(s) in a similar fashion as the allelic gene stc1a. The fact that the low2 phenotype can be achieved regardless of whether stc1a or stc1b is used as the major gene, supports the hypothesis that the differences between the phenotypes of LR28 and LR484 (Table 6) are due to genetic background differences (minor genes) that are independent of the Stc1 locus. The exact genetic relationship between stc1a and stc1b (gene action and interactions with specific modifier genes) is of little concern. The important contribution of the instant invention is provision of germplasm that can be used to develop soybean lines with heritable low seed raffinose saccharide content.

None of the selected lines from the pedigree A2396* (A3322*LR484) or A3322(2)*LR484 proved to be lower in stachyose content than unmodified stc1x check line LR28 when grown in the ST93 environment (Table 8). Based on this data, there is no indication that A2396 or A3322 contain modifiers of stc1x that further reduce seed raffinose saccharide content below the level of LR28.

Genetic Modifiers that Complement Low Raffinose Saccharide Genes in LR3705 and LR4271

In 1992, both LR3705 and LR4271 were crossed with elite line A3322 in an attempt to combine their low raffinose saccharide phenotype with the desirable agronomic performance of A3322 and to confirm the heritability of their low raffinose saccharide trait. F1 seeds from the A3322*LR3705 and A3322*LR4271 crosses were grown in the greenhouse during the fall of 1992 and allowed to self-pollinate to produce F2 seeds. Resultant F2 seeds were planted during the winter of 1993 at Isabela Puerto Rico (the "IP93" environment) and the resultant F2:3 seed families were analyzed by HPLC to determine their raffinose saccharide content. Low raffinose saccharide selections from these F2:3 seed families were made and F3 seeds from said selections were planted in the spring of 1993 at the Dupont Stine Research Farm in Newark Del. (the "ST93" environment) side-by-side with elite lines, LR28, LR484, LR3705, and LR4271 as controls. Resultant F3:4 seeds and control seeds from single plants were then analyzed by HPLC to confirm the heritability of low raffinose saccharide selections from the pedigrees A3322*LR3705 and A3322*LR4271.

Since seeds of LR3705 and LR4271 from the ST93 environment were higher in stachyose and total raffinose saccharide content than both LR28 and LR484, segregants from the crosses A3322*LR3705 and A3322*LR4271 were compared to their mutant parents to determine whether A3322 contains modifier(s) of the major low raffinose saccharide genes (Example 2) in the mutant lines. LR3705 had a stachyose content of 47±4.4 $\mu$mol/g in the ST93 environment. Using three standard deviations as the cutoff for statistical significance, selections from A3322*LR3705 with less than 34 $\mu$mol/g stachyose were considered to be significantly lower in stachyose than their mutant parent LR3705. LR4271 had a stachyose content of 32±5.8 $\mu$mol/g in the ST93 environment. Using three standard deviation as the cutoff, selections from A3322*LR4271 with less than 15 $\mu$mol/g stachyose were considered to be significantly lower in stachyose than their mutant parent LR3705.

All 3 selections of A3322*LR3705 were significantly lower in stachyose than both LR3705 and LR28 (designated "low2" in Table 8). Said selection had higher galactinol accumulation than their mutant patent but the net result was a reduction in total raffinose saccharides by approximately 50%. The phenotypes of the modified selections from A3322*LR3705 fit the definition of low2 provided previously. This is good evidence that A3322 contains genes that modify the expression of low raffinose saccharide gene in LR3705. Although LR3705 appears to be inferior to LR28 and LR484 in terms of its low raffinose saccharide phentotype, when recombined with modifier(s), LR3705 can produce progeny that are superior to unmodified stc1x lines.

Both selections of A3322*LR4271 were significantly lower in stachyose than LR4271 but not significantly lower than LR28 (Table 8). Unlike selections from A3322*LR3705, A3322*LR4271 selections retained the low galactinol content of their mutant parent resulting in an impressive reduction in total raffinose saccharides. Although none passed the statistical test of being significantly lower in stachyose than LR28, based on their total raffinose saccharide content, selections from A3322*LR4271 most closely fit the low2 profile defined previously. This is good evidence that A3322 contains genes that modify the expression of low raffinose saccharide gene in LR4271. Although LR4271 appears to be slightly inferior to LR28 and LR484 in terms of its low raffinose saccharide phenotype, when recombined with modifier(s), LR4271 can produce progeny that are superior to unmodified stc1x lines.

Modifiers of stc1x that Reduce Both Stachyose and Galactinol Content

The instant modifier discovery procedure was used to determine whether elite line A1929 and mutant line LR33 (Example 2) contain modifiers of stc1x genes. In the summer of 1991, A1929 was crossed with an unmodified stc1x line derived from the pedigree ST9025*LR28 to produce F1 seeds of pedigree (ST9025*LR28)*A1929. In the same season, LR33 was crossed with LR28 to produce F1 seeds of pedigree LR33*LR28. F1 plants from these two pedigrees were self pollinated to produce segregating F2 progeny that were planted in Puerto Rico during the winter of 1992 (the "IP92" environment). Seeds of the unmodified stc1x check lines LR28 and LR484 were planted in the IP92 environment as well. In the spring of 1992, F2:3 seeds were harvested from each F2 plant and samples of each F2:3 line were screened for α-galactoside content using the enzymatic method described in Example 1 as a preliminary screen. Low α-galactoside selections from the enzymatic screen were then advanced to the more informative HPLC analysis so that the complete raffinose saccharide profile could be determined. Selections from the IP92 environment (Table 9) along with 30 conventional elite lines were planted in the spring of 1992 at the DuPont Stine Research Farm in Newark, Del. U.S.A. (the "ST92" environment). The ST92 phenotypes (Table 9) were means of at least 3 and usually 5 or more plants grown in an environment typical of commercial soybean production.

In the ST92 environment, LR28 was slightly lower in stachyose and total raffinose saccharide content than LR484 (Table 9). LR28 was therefore used as the unmodified stc1x control line to which new selections were compared for the presence of modifier genes. LR28 had a seed stachyose content of 24±4.0 $\mu$mol/g stachyose in said ST92 environment. Using three standard deviation from said mean as the cutoff, lines with less than 12 $\mu$mol/g seed stachyose content were considered to be significantly lower in seed stachyose content.

Although very few lines of the pedigree (ST9025*LR28)*A1929 were available for testing, 3 out of 4 tested were significantly lower in stachyose than the unmodified stc1x line LR28 when grown in the ST92 environment (Table 9). This stachyose reduction translated into a significant reduction in the total raffinose pool and a profile that fits the previous definition of low2. The ST92 environment provided conclusive evidence that A1929 contains modifier gene(s) that complement stc1x to further reduce raffinose saccharide content.

During the summer of 1992, low2 selections from the pedigree (ST9025*LR28)*A1929 were backcrossed again to elite line A1929 in an attempt to develop low2 lines with improved agronomics. F1 plants of this backcross pedigree (ST9025*LR28)*(2)A1929 were grown in the greenhouse and self pollinated to produce F2 seeds. Said F2 seeds were then planted in Isabela, Puerto Rico during the winter of 1993 "IP93" environment) so that F2:3 seeds could be obtained for segregation analysis. After harvest, F2:3 seed families were prescreened for the stc1x gene by TLC analysis. Said stc1x selections were then assayed for the complete raffinose saccharide profile by the HPLC method. The IP93 raffinose saccharide profile of all stc1x selections from the (ST9025*LR28)*(2)A1929 pedigree were low2 in terms of stachyose (Table 9). Apparently, the modifier gene(s) from A1929 that reduce stachyose content had been fixed (i.e. were no longer segregating). F3 seed of each F2:3 line were then planted during the spring of 1993 at the DuPont Stine Crop Research Farm in Newark, Del. U.S.A. (the "ST93" environment) and allowed to reach maturity and produce F3:4 progeny in the fall of 1993. Three to four F3:4 lines from each F2:3 line were harvested and assayed for raffinose saccharide content by the HPLC method to obtain an average raffinose saccharide profile for each F2-derived line that was grown in an environment typical of commercial soybean production.

The seed stachyose content of LR28 in the ST93 environment was 19±2.2 $\mu$mol/g. Three standard deviations below the mean of 19 (less than 13 $\mu$mol/g) was used as the statistical cutoff for modifiers of stachyose content in this environment. F3:4 means of (ST9025*LR28)*(2)A1929 selections (Table 9) revealed the discovery of a new phenotype termed "low3". This phenotype is characterized as being significantly lower in stachyose content than stc1x check lines and as having a significantly lower galactinol accumulation than low2 lines (Table 9). Therefore confirmation of the low3 phenotype required two separate statistical tests. First, low3 lines had to be significantly lower in stachyose than LR28 (i.e. less than 13 $\mu$mol/g). Second, seed of putative low3 lines had to contain significantly less galactinol than low2 controls. In the ST93 environment, the low2 control line of pedigree X3337*LR28 had a galactinol content of 29±5.0 $\mu$mol/g. Using three standard deviations from this mean as the cutoff, lines with 14 $\mu$mol/g or less of galactinol were considered to have a significantly lower galactinol content than that of confirmed low2 lines. Lines that were both lower in stachyose than LR28 and lower in galactinol than the low2 check line are designated as "low3" in Table 9. These lines represent the new class of low3 phenotype. The low3 phenotype results in a significant improvement of low total raffinose saccharide content when compared to either unmodified stc1x (low1) lines or the low2 lines previously described.

Of the five F2 plants of pedigree LR33*LR28 grown in IP92, one line (IP92-33082-106) confirmed in the F3 generation (ST92 environment) with an even lower raffinose saccharide content than previously observed (Table 9). Not only was the stachyose content extremely low (average of 4 $\mu$mol/g) and better than the stc1x check line LR28, but there was almost none of the galactinol accumulation that is usually associated with stc1x genes. This was the first observation of the "low4" phenotype. Since the appropriate low3 control lines were not available in the ST92 environment, it was not possible to test the statistical significance of this first low4 selection.

In an attempt to cross the low4 phenotype into more agronomically elite backgrounds, low4 selections from the pedigree LR33*LR28 were crossed with elite lines A1923, A2396, A2872, and A3322 during the summer of 1992. F1 seeds of these crosses were grown in the greenhouse during the fall of 1992 and the resulting F2 seeds were grown in Isabela Puerto Rico during the winter of 1993 (the "IP93" environment) to produce F2 plants and their resultant F2:3 seed progeny. Said F2:3 seeds were prescreened for the stc1x gene by TLC analysis and selections were advanced to HPLC analysis to determine their complete raffinose saccharide profile. Based on the IP93 profile of single F2 plants (left side of Table 7), F3 seeds of putative low4 selections were then planted and grown to maturity at the DuPont Stine Research Farm during the summer of 1993 (the "ST93" environment). Conventional elite lines, unmodified stc1x lines, a low2 control of pedigree X3337*LR28, and F5 plants of putative low4 selections from LR33*LR28 were also grown in the ST93 environment as check lines. New low3 selections from the (ST9025*LR28)*(2)A1929 were also available in the ST93 environment to test the statistical difference of low4 selections. Seed from check lines and the selections of (LR33*LR28)*elite crosses were then assayed by HPLC for their total raffinose saccharide content. F3:4 seed from at least 3 F3 plants was used to calculate the mean ST93 phenotype of each line from the (LR33*LR28)*elite crosses.

TABLE 7

Evidence for Genetic Modifiers of stclx in Lines X3337 and A4715

| YEAR | PEDIGREE | SELECTION | GEN1 | N | STC | RAF | GAL | RSA | GEN2 | N | PLOT | STC | RAF | GAL | RSA | SSDV |
|---|---|---|---|---|---|---|---|---|---|---|---|---|---|---|---|---|
|  |  |  |  | IP91 Environment |  |  |  |  |  |  |  | ST91 Environment |  |  |  |  |
| 91 | A3205 |  | ELIT |  |  |  |  |  | ELIT | 9 | ST91-37 | 68 | 17 | 0 | 153 |  | 10.2 |
| 91 | A3322 |  | ELIT |  |  |  |  |  | ELIT | 8 | ST91-35 | 102 | 21 | 0 | 225 |  | 10.7 |
| 91 | A4715 |  | ELIT |  |  |  |  |  | ELIT | 9 | ST91-19 | 108 | 18 | 5 | 236 |  | 9.3 |
| 91 | LR28 |  | GR90 |  |  |  |  |  | GR90 | 38 | ST91-82 | 22 | 5 | 50 | 98 |  | 2.5 |
| 91 | LR484 |  | GR91 |  |  |  |  |  | GR91 | 9 | ST92-84 | 27 | 3 | 13 | 69 |  | 3.3 |
| 91 | X3337*LR28 | IP91-5-344 | F2:3 | 1 | 33 | 12 | 24 | 101 | F3:4 | 5 | ST91-1477 | 5 | 1 | 25 | 37 |  | 1.1 |
| 91 | X3337*LR28 | IP91-5-147 | F2:3 | 1 | 22 | 9 | 30 | 83 | F3:4 | 25 | ST91-1458 | 6 | 4 | 28 | 45 |  | 2.5 |
| 91 | X3337*LR28 | IP91-5-365 | F2:3 | 1 | 19 | 7 | 38 | 84 | F3:4 | 41 | ST91-81 | 7 | 1 | 40 | 55 |  | 3.2 |
| 91 | X3337*LR28 | IP91-5-348 | F2:3 | 1 | 37 | 12 | 28 | 114 | F3:4 | 5 | ST91-1478 | 11 | 2 | 38 | 62 |  | 1.6 |
| 91 | X3337*LR28 | IP91-5-207 | F2:3 | 1 | 22 | 9 | 27 | 80 | F3:4 | 5 | ST91-1085 | 11 | 2 | 42 | 65 |  | 0.7 |
| 91 | X3337*LR28 | IP91-5-339 | F2:3 | 1 | 29 | 11 | 29 | 99 | F3:4 | 5 | ST91-1476 | 12 | 5 | 43 | 68 |  | 3.4 |
| 91 | X3337*LR23 | IP91-6-004 | F2:3 | 1 | 31 | 10 | 34 | 104 | F3:4 | 5 | ST91-1481 | 12 | 5 | 40 | 68 |  | 11.0 |
| 91 | X3337*LR28 | IP91-5-071 | F2:3 | 1 | 27 | 9 | 38 | 101 | F3:4 | 5 | ST91-1446 | 13 | 2 | 62 | 89 |  | 1.6 |
| 91 | X3337*LR23 | IP91-5-297 | F2:3 | 1 | 26 | 11 | 30 | 93 | F3:4 | 5 | ST91-1473 | 14 | 3 | 61 | 92 |  | 5.1 |
| 91 | X3337*LR28 | IP91-5-340 | F2:3 | 1 | 27 | 11 | 30 | 95 | F3:4 | 5 | ST91-1097 | 15 | 3 | 20 | 53 |  | 2.0 |
| 91 | X3337*LR28 | IP91-5-037 | F2:3 | 1 | 22 | 10 | 39 | 92 | F3:4 | 5 | ST91-1443 | 15 | 3 | 66 | 98 |  | 2.5 |
| 91 | X3337*LR28 | IP91-5-263 | F2:3 | 1 | 34 | 11 | 21 | 99 | F3:4 | 4 | ST91-1470 | 17 | 4 | 46 | 83 |  | 9.4 |
| 91 | X3337*LR28 | IP91-5-098 | F2:3 | 1 | 27 | 10 | 43 | 107 | F3:4 | 5 | ST91-1073 | 18 | 3 | 41 | 80 |  | 3.6 |
| 91 | X3337*LR28 | IP91-5-194 | F2:3 | 1 | 22 | 9 | 39 | 92 | F3:4 | 5 | ST91-1084 | 18 | 3 | 48 | 88 |  | 10.7 |
| 91 | X3337*LR28 | IP91-5-270 | F2:3 | 1 | 15 | 8 | 49 | 85 | F3:4 | 5 | ST91-1472 | 18 | 2 | 62 | 98 |  | 5.1 |
| 91 | X3337*LR28 | IP91-5-074 | F2:3 | 1 | 26 | 10 | 34 | 96 | F3:4 | 3 | ST91-1099 | 19 | 3 | 55 | 96 |  | 3.6 |
| 91 | X3337*LR28 | IP91-5-044 | F2:3 | 1 | 26 | 10 | 36 | 97 | F3:4 | 5 | ST91-1447 | 20 | 2 | 53 | 93 |  | 4.9 |
| 91 | X3337*LR28 | IP91-5-091 | F2:3 | 1 | 28 | 10 | 42 | 108 | F3:4 | 5 | ST91-1072 | 21 | 2 | 37 | 83 |  | 4.0 |
| 91 | X3337*LR28 | IP91-5-364 | F2:3 | 1 | 14 | 9 | 45 | 80 | F3:4 | 5 | ST91-1099 | 22 | 2 | 29 | 77 |  | 5.8 |
| 91 | X3337*LR28 | IP91-5-298 | F2:3 | 1 | 21 | 9 | 36 | 86 | F3:4 | 3 | ST91-1094 | 22 | 4 | 29 | 77 |  | 11.0 |
| 91 | X3337*LR28 | IP91-5-274 | F2:3 | 1 | 28 | 10 | 18 | 84 | F3:4 | 5 | ST91-1091 | 22 | 4 | 32 | 81 |  | 4.9 |
| 91 | X3337*LR28 | IP91-5-171 | F2:3 | 1 | 18 | 8 | 37 | 79 | F3:4 | 4 | ST91-1080 | 22 | 2 | 52 | 99 |  | 6.3 |
| 91 | X3337*LR28 | IP91-5-330 | F2:3 | 1 | 27 | 10 | 26 | 90 | F3:4 | 5 | ST91-1475 | 23 | 6 | 33 | 84 |  | 1.6 |
| 91 | X3337*LR28 | IP91-5-318 | F2:3 | 1 | 20 | 9 | 49 | 98 | F3:4 | 4 | ST91-1474 | 25 | 6 | 38 | 94 |  | 9.2 |
| 91 | X3337*LR28 | IP91-5-267 | F2:3 | 1 | 29 | 11 | 29 | 107 | F3:4 | 3 | ST91-1090 | 27 | 5 | 36 | 94 |  | 4.3 |
| 91 | X3337*LR28 | IP91-5-152 | F2:3 | 1 | 21 | 9 | 30 | 82 | F3:4 | 5 | ST91-1078 | 27 | 4 | 37 | 96 |  | 8.5 |
| 91 | X3337*LR28 | IP91-5-268 | F2:3 | 1 | 25 | 9 | 29 | 88 | F3:4 | 4 | ST91-1471 | 29 | 6 | 42 | 106 |  | 1.0 |
| 91 | X3337*LR28 | IP91-5-111 | F2:3 | 1 | 21 | 9 | 30 | 82 | F3:4 | 4 | ST91-1074 | 31 | 6 | 35 | 104 |  | 28.0 |
| 91 | X3337*LR28 | IP91-5-020 | F2:3 | 1 | 29 | 7 | 24 | 90 | F3:4 | 5 | ST91-1442 | 31 | 5 | 39 | 106 |  | 4.5 |
| 91 | A4715*LR28 | IP91-6-126 | F2:3 | 1 | 12 | 8 | 46 | 77 | F3:4 | 15 | ST91-1175 | 6 | 0 | 33 | 46 | low2 | 1.5 |
| 91 | A4715*LR28 | IP91-6-121 | F2:3 | 1 | 32 | 11 | 33 | 108 | F3:4 | 5 | ST91-1498 | 8 | 1 | 35 | 52 | low2 | 4.2 |
| 91 | A4715*LR28 | IP91-6-111 | F2:3 | 1 | 20 | 9 | 49 | 98 | F3:4 | 5 | ST91-1496 | 8 | 1 | 36 | 53 | low2 | 2.5 |
| 91 | A4715*LR28 | IP91-6-120 | F2:3 | 1 | 32 | 11 | 33 | 107 | F3:4 | 5 | ST91-1497 | 10 | 0 | 28 | 48 | low2 | 0.9 |
| 91 | A4715*LR28 | IP91-6-123 | F2:3 | 1 | 28 | 10 | 29 | 95 | F3:4 | 5 | ST91-1500 | 10 | 1 | 31 | 51 | low2 | 2.8 |
| 91 | A4715*LR28 | IP91-6-122 | F2:3 | 1 | 23 | 9 | 32 | 87 | F3:4 | 4 | ST91-1499 | 10 | 1 | 36 | 56 | low2 | 2.1 |
| 91 | A4715*LR28 | IP91-6-168 | F2:3 | 1 | 13 | 7 | 28 | 62 | F3:4 | 3 | ST91-1506 | 13 | 1 | 39 | 65 | low2 | 3.8 |
| 91 | A4715*LR28 | IP91-6-213 | F2:3 | 1 | 24 | 9 | 30 | 86 | F3:4 | 5 | ST91-1180 | 15 | 2 | 45 | 79 |  | 2.2 |
| 91 | A4715*LR28 | IP91-6-010 | F2:3 | 1 | 24 | 16 | 36 | 99 | F3:4 | 5 | ST91-1156 | 16 | 4 | 56 | 93 | low2 | 1.0 |
| 91 | A4715*LR28 | IP91-6-183 | F2:3 | 1 | 21 | 9 | 36 | 87 | F3:4 | 5 | ST91-1507 | 17 | 2 | 38 | 75 | low2 | 3.6 |
| 91 | A4715*LR28 | IP91-6-044 | F2:3 | 1 | 24 | 9 | 32 | 89 | F3:4 | 4 | ST91-1486 | 17 | 9 | 37 | 79 | low2 | 8.8 |

TABLE 7-continued

Evidence for Genetic Modifiers of stclx in Lines X3337 and A4715

| YEAR | PEDIGREE | SELECTION | GEN1 | N | STC | RAF | GAL | RSA | GEN2 | N | PLOT | STC | RAF | GAL | RSA | SSDV |
|---|---|---|---|---|---|---|---|---|---|---|---|---|---|---|---|---|
| 91 | A4715*LR28 | IP91-6-143 | P2:3 | 1 | 29 | 10 | 47 | 113 | F3:4 | 5 | ST91-1178 | 17 | 1 | 73 | 108 | 3.6 |
| 91 | A4715*LR28 | IP91-6-073 | P2:3 | 1 | 23 | 10 | 39 | 93 | F3:4 | 5 | ST91-1490 | 19 | 0 | 46 | 84 | 2.5 |
| 91 | A4715*LR28 | IP91-6-083 | P2:3 | 1 | 25 | 9 | 38 | 97 | F3:4 | 5 | ST91-1491 | 20 | 1 | 54 | 95 | 3.6 |
| 91 | A4715*LR28 | IP91-6-196 | P2:3 | 1 | 22 | 8 | 42 | 95 | F3:4 | 4 | ST91-1511 | 22 | 2 | 43 | 89 | 7.2 |
| 91 | A4715*LR28 | IP91-6-068 | P2:3 | 1 | 24 | 9 | 34 | 89 | F3:4 | 4 | ST91-1169 | 23 | 1 | 45 | 93 | 3.6 |
| 91 | A4715*LR28 | IP91-6-206 | P2:3 | 1 | 33 | 10 | 24 | 100 | F3:4 | 3 | ST91-1512 | 30 | 2 | 37 | 98 | 5.4 |
| 91 | A4715*LR28 | IP91-6-277 | P2:3 | 1 | 28 | 9 | 40 | 107 | F3:4 | 5 | ST91-1516 | 35 | 3 | 57 | 121 | 34.0 |
| 91 | A4715*LR28 | IP91-6-088 | P2:3 | 1 | 17 | 8 | 53 | 95 | F3:4 | 3 | ST91-1492 | 35 | 2 | 34 | 107 | 18.6 |
| 91 | A4715*LR28 | IP91-6-187 | P2:3 | 1 | 22 | 8 | 35 | 86 | F3:4 | 3 | ST91-1509 | 47 | 11 | 13 | 119 | 6.8 |
| 91 | A4715*LR28 | IP91-6-208 | P2:3 | 1 | 38 | 11 | 28 | 114 | F3:4 | 4 | ST91-1513 | 56 | 4 | 44 | 161 | 33.6 |
| 91 | A4715*LR28 | IP91-6-066 | P2:3 | 1 | 13 | 5 | 35 | 67 | F3:4 | 3 | ST91-78 | 81 | 22 | 0 | 183 | 5.2 |
| 91 | ST9025*LR28 | IP91-3-036 | P2:3 | 1 | 26 | 8 | 24 | 83 | F3:4 | 4 | ST91-1105 | 9 | 2 | 48 | 69 | 7.4 low2 |
| 91 | ST9025*LR28 | IP91-3-081 | P2:3 | 1 | 35 | 10 | 28 | 109 | F3:4 | 5 | ST91-1112 | 19 | 1 | 25 | 65 | 3.6 |
| 91 | ST9025*LR28 | IP91-3-241 | P2:3 | 1 | 25 | 10 | 23 | 83 | F3:4 | 5 | ST91-1139 | 21 | 3 | 40 | 86 | 4.2 |
| 91 | ST9025*LR28 | IP91-3-047 | P2:3 | 1 | 20 | 7 | 30 | 76 | F3:4 | 5 | ST91-1107 | 22 | 2 | 20 | 67 | 4.2 |
| 91 | ST9025*LR28 | IP91-3-233 | P2:3 | 1 | 28 | 10 | 16 | 83 | F3:4 | 3 | ST91-1137 | 22 | 3 | 32 | 79 | 10.5 |
| 91 | ST9025*LR28 | IP91-3-177 | P2:3 | 1 | 27 | 10 | 20 | 82 | F3:4 | 5 | ST91-1134 | 23 | 2 | 22 | 70 | 2.3 |
| 91 | ST9025*LR28 | IP91-3-234 | P2:3 | 1 | 29 | 9 | 33 | 100 | F3:4 | 3 | ST91-1108 | 23 | 1 | 24 | 71 | 3.4 |
| 91 | ST9025*LR28 | IP91-3-109 | P2:3 | 1 | 32 | 10 | 24 | 98 | F3:4 | 3 | ST91-1116 | 23 | 3 | 25 | 74 | 1.6 |
| 91 | ST9025*LR28 | IP91-3-175 | P2:3 | 1 | 34 | 11 | 38 | 118 | F3:4 | 5 | ST91-1125 | 23 | 2 | 26 | 74 | 8.3 |
| 91 | ST9025*LR28 | IP91-3-177 | P2:3 | 1 | 36 | 13 | 30 | 115 | F3:4 | 5 | ST91-1127 | 23 | 3 | 26 | 74 | 1.6 |
| 91 | ST9025*LR28 | IP91-3-234 | P2:3 | 1 | 20 | 9 | 27 | 76 | F3:4 | 5 | ST91-1138 | 23 | 2 | 29 | 77 | 3.8 |
| 91 | ST9025*LR28 | IP91-3-107 | P2:3 | 1 | 32 | 10 | 24 | 98 | F3:4 | 5 | ST91-1115 | 24 | 3 | 23 | 73 | 3.6 |
| 91 | ST9025*LR28 | IP91-3-228 | P2:3 | 1 | 29 | 9 | 29 | 98 | F3:4 | 5 | ST91-1135 | 25 | 2 | 20 | 71 | 3.6 |
| 91 | ST9025*LR28 | IP91-3-028 | P2:3 | 1 | 26 | 8 | 16 | 77 | F3:4 | 4 | ST91-1104 | 25 | 3 | 34 | 87 | 5.4 |
| 91 | ST9025*LR28 | IP91-3-039 | P2:3 | 1 | 26 | 8 | 25 | 85 | F3:4 | 5 | ST91-1106 | 25 | 5 | 33 | 87 | 5.8 |
| 91 | ST9025*LR28 | IP91-3-093 | P2:3 | 1 | 36 | 12 | 22 | 105 | F3:4 | 5 | ST91-1113 | 26 | 2 | 30 | 84 | 2.2 |
| 91 | ST9025*LR28 | IP91-3-094 | P2:3 | 1 | 23 | 9 | 35 | 90 | F3:4 | 57 | ST91-80 | 26 | 4 | 34 | 90 | 6.0 |
| 91 | ST9025*LR28 | IP91-3-115 | P2:3 | 1 | 25 | 10 | 20 | 78 | F3:4 | 5 | ST91-1118 | 26 | 1 | 41 | 95 | 13.0 |
| 91 | ST9025*LR28 | IP91-3-075 | P2:3 | 1 | 34 | 11 | 15 | 92 | F3:4 | 5 | ST91-1109 | 27 | 2 | 26 | 81 | 3.6 |
| 91 | ST9025*LR28 | IP91-3-022 | P2:3 | 1 | 25 | 9 | 20 | 78 | F3:4 | 3 | ST91-1102 | 27 | 2 | 47 | 103 | 2.6 |
| 91 | ST9025*LR28 | IP91-3-101 | P2:3 | 1 | 29 | 10 | 23 | 90 | F3:4 | 5 | ST91-1114 | 28 | 2 | 22 | 81 | 6.9 |
| 91 | ST9025*LR28 | IP91-3-261 | P2:3 | 1 | 24 | 9 | 32 | 88 | F3:4 | 5 | ST91-1142 | 28 | 3 | 28 | 86 | 4.9 |
| 91 | ST9025*LR28 | IP91-3-026 | P2:3 | 1 | 37 | 13 | 25 | 110 | F3:4 | 4 | ST91-1103 | 28 | 2 | 35 | 94 | 4.2 |
| 91 | ST9025*LR28 | IP91-3-180 | P2:3 | 1 | 34 | 11 | 32 | 111 | F3:4 | 5 | ST91-1128 | 29 | 1 | 33 | 93 | 5.4 |
| 91 | ST9025*LR28 | IP91-3-258 | P2:3 | 1 | 35 | 10 | 30 | 111 | F3:4 | 4 | ST91-1140 | 29 | 3 | 32 | 93 | 6.3 |
| 91 | ST9025*LR28 | IP91-3-273 | P2:3 | 1 | 22 | 8 | 30 | 82 | F3:4 | 5 | ST91-1143 | 29 | 5 | 45 | 107 | 2.5 |
| 91 | ST9025*LR28 | IP91-3-198 | P2:3 | 1 | 27 | 9 | 20 | 82 | F3:4 | 5 | ST91-1131 | 30 | 3 | 34 | 97 | 7.2 |
| 91 | ST9025*LR28 | IP91-3-159 | P2:3 | 1 | 39 | 12 | 25 | 116 | F3:4 | 23 | ST91-79 | 30 | 6 | 32 | 98 | 20.6 |
| 91 | ST9025*LR28 | IP91-3-232 | P2:3 | 1 | 22 | 8 | 30 | 83 | F3:4 | 5 | ST91-1136 | 31 | 3 | 23 | 88 | 6.0 |
| 91 | ST9025*LR28 | IP91-3-290 | P2:3 | 1 | 34 | 9 | 30 | 99 | F3:4 | 4 | ST91-1144 | 31 | 5 | 35 | 102 | 4.6 |
| 91 | ST9025*LR28 | IP91-3-188 | P2:3 | 1 | 30 | 10 | 25 | 87 | F3:4 | 3 | ST91-1129 | 32 | 2 | 18 | 84 | 4.8 |
| 91 | ST9025*LR28 | IP91-3-133 | P2:3 | 1 | 26 | 11 | 23 | 108 | F3:4 | 4 | ST91-1121 | 34 | 3 | 27 | 96 | 5.0 |
| 91 | ST9025*LR28 | IP91-3-218 | P2:3 | 1 | 37 | 9 | 24 | 74 | F3:4 | 4 | ST91-1132 | 35 | 4 | 28 | 103 | 6.8 |
| 91 | ST9025*LR28 | IP91-3-139 | P2:3 | 1 | 21 | 11 | 30 | 108 | F3:4 | 5 | ST91-1122 | 41 | 2 | 42 | 126 | 4.9 |
| 91 | ST9025*LR28 | IP91-3-190 | P2:3 | 1 | 33 | 9 | 26 | 84 | F3:4 | 5 | ST91-1130 | 66 | 14 | 25 | 169 | 29.8 |
| 91 | ST9026*LR28 | IP91-4-026 | P2:3 | 1 | 25 | 11 | 27 | 95 | F3:4 | 5 | ST91-1004 | 15 | 2 | 31 | 63 | 3.6 |
| 91 | ST9026*LR28 | IP91-4-170 | P2:3 | 1 | 29 | 10 | 29 | 97 | F3:4 | 5 | ST91-1026 | 17 | 3 | 33 | 71 | 5.1 |

TABLE 7-continued

Evidence for Genetic Modifiers of stclx in Lines X3337 and A4715

| YEAR | PEDIGREE | SELECTION | GEN1 | N | STC | RAF | GAL | RSA | GEN2 | N | PLOT | STC | RAF | GAL | RSA | SSDV |
|---|---|---|---|---|---|---|---|---|---|---|---|---|---|---|---|---|
| 91 | ST9026*LR28 | IP91-4-150 | F2:3 | 1 | 28 | 10 | 29 | 93 | F3:4 | 5 | ST91-1025 | 17 | 2 | 36 | 72 | 4.5 |
| 91 | ST9026*LR28 | IP91-4-256 | F2:3 | 1 | 36 | 11 | 35 | 117 | F3:4 | 3 | ST91-1041 | 17 | 4 | 34 | 73 | 0.5 |
| 91 | ST9026*LR28 | IP91-4-149 | F2:3 | 1 | 26 | 9 | 35 | 96 | F3:4 | 5 | ST91-1024 | 18 | 2 | 43 | 79 | 4.5 |
| 91 | ST9026*LR28 | IP91-4-210 | F2:3 | 1 | 29 | 9 | 36 | 103 | F3:4 | 5 | ST91-1033 | 19 | 2 | 32 | 73 | 3.8 |
| 91 | ST9026*LR28 | IP91-4-288 | F2:3 | 1 | 38 | 12 | 18 | 107 | F3:4 | 5 | ST91-1046 | 20 | 5 | 29 | 73 | 5.1 |
| 91 | ST9026*LR28 | IP91-4-224 | F2:3 | 1 | 30 | 10 | 30 | 101 | F3:4 | 5 | ST91-1039 | 20 | 4 | 32 | 75 | 3.1 |
| 91 | ST9026*LR28 | IP91-4-044 | F2:3 | 1 | 27 | 9 | 32 | 95 | F3:4 | 5 | ST91-1006 | 20 | 3 | 36 | 80 | 4.0 |
| 91 | ST9026*LR28 | IP91-4-220 | F2:3 | 1 | 36 | 12 | 34 | 117 | F3:4 | 5 | ST91-1037 | 20 | 4 | 39 | 84 | 1.1 |
| 91 | ST9026*LR28 | IP91-4-294 | F2:3 | 1 | 37 | 12 | 26 | 112 | F3:4 | 5 | ST91-1048 | 21 | 6 | 29 | 77 | 0.4 |
| 91 | ST9026*LR28 | IP91-4-290 | F2:3 | 1 | 35 | 11 | 34 | 115 | F3:4 | 5 | ST91-1047 | 21 | 4 | 32 | 79 | 4.5 |
| 91 | ST9026*LR28 | IP91-4-190 | F2:3 | 1 | 33 | 10 | 33 | 110 | F3:4 | 5 | ST91-1029 | 22 | 3 | 35 | 82 | 6.3 |
| 91 | ST9026*LR28 | IP91-4-184 | F2:3 | 1 | 32 | 10 | 37 | 110 | F3:4 | 5 | ST91-1028 | 22 | 4 | 40 | 88 | 2.0 |
| 91 | ST9026*LR28 | IP91-4-104 | F2:3 | 1 | 35 | 11 | 28 | 109 | F3:4 | 5 | ST91-1018 | 23 | 4 | 31 | 80 | 2.2 |
| 91 | ST9026*LR28 | IP91-4-274 | F2:3 | 1 | 30 | 10 | 24 | 95 | F3:4 | 5 | ST91-1044 | 23 | 4 | 31 | 81 | 4.5 |
| 91 | ST9026*LR28 | IP91-4-148 | F2:3 | 1 | 36 | 11 | 30 | 112 | F3:4 | 5 | ST91-1023 | 23 | 3 | 31 | 81 | 3.1 |
| 91 | ST9026*LR28 | IP91-4-223 | F2:3 | 1 | 32 | 11 | 35 | 109 | F3:4 | 4 | ST91-1038 | 23 | 6 | 39 | 91 | 3.8 |
| 91 | ST9026*LR28 | IP91-4-214 | F2:3 | 1 | 33 | 10 | 34 | 109 | F3:4 | 5 | ST91-1035 | 24 | 2 | 27 | 78 | 2.9 |
| 91 | ST9026*LR28 | IP91-4-012 | F2:3 | 1 | 27 | 9 | 22 | 85 | F3:4 | 5 | ST91-1003 | 24 | 3 | 32 | 83 | 6.3 |
| 91 | ST9026*LR28 | IP91-4-212 | F2:3 | 1 | 28 | 9 | 30 | 96 | F3:4 | 5 | ST91-1034 | 24 | 2 | 40 | 90 | 4.7 |
| 91 | ST9026*LR28 | IP91-4-096 | F2:3 | 1 | 30 | 11 | 27 | 98 | F3:4 | 5 | ST91-1015 | 25 | 4 | 31 | 84 | 2.7 |
| 91 | ST9026*LR28 | IP91-4-180 | F2:3 | 1 | 32 | 11 | 33 | 107 | F3:4 | 5 | ST91-1027 | 25 | 2 | 41 | 92 | 5.4 |
| 91 | ST9026*LR28 | IP91-4-046 | F2:3 | 1 | 30 | 9 | 28 | 97 | F3:4 | 5 | ST91-1007 | 25 | 8 | 43 | 99 | 3.6 |
| 91 | ST9026*LR28 | IP91-4-099 | F2:3 | 1 | 27 | 10 | 38 | 102 | F3:4 | 5 | ST91-1017 | 25 | 3 | 50 | 104 | 2.7 |
| 91 | ST9026*LR28 | IP91-4-118 | F2:3 | 1 | 31 | 11 | 20 | 91 | F3:4 | 5 | ST91-1020 | 26 | 2 | 24 | 78 | 3.8 |
| 91 | ST9026*LR28 | IP91-4-142 | F2:3 | 1 | 39 | 13 | 21 | 111 | F3:4 | 5 | ST91-1022 | 26 | 3 | 33 | 87 | 8.5 |
| 91 | ST9026*LR28 | IP91-4-112 | F2:3 | 1 | 37 | 11 | 21 | 104 | F3:4 | 5 | ST91-1019 | 26 | 3 | 34 | 89 | 6.7 |
| 91 | ST9026*LR28 | IP91-4-262 | F2:3 | 1 | 37 | 12 | 23 | 109 | F3:4 | 3 | ST91-1042 | 26 | 4 | 34 | 89 | 2.9 |
| 91 | ST9026*LR28 | IP91-4-031 | F2:3 | 1 | 29 | 10 | 32 | 99 | F3:4 | 6 | ST91-1005 | 26 | 4 | 40 | 96 | 3.7 |
| 91 | ST9026*LR28 | IP91-4-093 | F2:3 | 1 | 33 | 11 | 29 | 107 | F3:4 | 6 | ST91-1014 | 27 | 4 | 34 | 91 | 7.3 |
| 91 | ST9026*LR28 | IP91-4-055 | F2:3 | 1 | 30 | 10 | 33 | 102 | F3:4 | 5 | ST91-1008 | 27 | 7 | 38 | 98 | 2.0 |
| 91 | ST9026*LR28 | IP91-4-075 | F2:3 | 1 | 24 | 11 | 24 | 111 | F3:4 | 5 | ST91-1011 | 29 | 7 | 30 | 96 | 4.7 |
| 91 | ST9026*LR28 | IP91-4-098 | F2:3 | 1 | 38 | 11 | 36 | 102 | F3:4 | 5 | ST91-1016 | 30 | 4 | 36 | 101 | 13.6 |
| 91 | ST9026*LR28 | IP91-4-079 | F2:3 | 1 | 29 | 10 | 28 | 114 | F3:4 | 5 | ST91-1012 | 39 | 9 | 34 | 108 | 8.0 |
| 91 | ST9026*LR28 | IP91-4-266 | F2:3 | 1 | 28 | 10 | 30 | 97 | F3:4 | 5 | ST91-1043 | 46 | 9 | 15 | 116 | 22.1 | low2 = significantly lower in stachyose than LR28 control

TABLE 8

Evidence for Genetic Modifiers of Low Raffinose Saccharide Content in A5843 and A3322

| YEAR | PEDIGREE | SELECTION | GEN1 | N | STC | RAF | GAL | RSA | GEN2 | N | PLOT | STC | RAF | GAL | RSA | SSDV |
|---|---|---|---|---|---|---|---|---|---|---|---|---|---|---|---|---|
| | | | | | IP93 Environment | | | | | | | ST93 Environment | | | | |
| 93 | A1923 | | ELIT | | | | | | ELIT | 8 | ST93-208 | 69 | 19 | 0 | 156 | 3.4 |
| 93 | A1929 | | ELIT | | | | | | ELIT | 8 | ST93-204 | 75 | 17 | 0 | 167 | 4.8 |
| 93 | A2396 | | ELIT | | | | | | ELIT | 8 | ST93-212 | 76 | 19 | 0 | 171 | 3.4 |
| 93 | A2835 | | ELIT | | | | | | ELIT | 8 | ST93-216 | 74 | 20 | 0 | 168 | 5.7 |
| 93 | A2872 | | ELIT | | | | | | ELIT | 8 | ST93-220 | 80 | 19 | 0 | 180 | 3.7 |
| 93 | A3322 | | ELIT | | | | | | ELIT | 8 | ST93-224 | 84 | 16 | 0 | 184 | 2.0 |
| 93 | A4715 | | ELIT | | | | | | ELIT | 8 | ST93-232 | 78 | 12 | 0 | 167 | 7.1 |
| 93 | WILLIAMS82 | | ELIT | | | | | | ELIT | 8 | ST93-228 | 72 | 13 | 0 | 156 | 7.6 |
| 93 | LR28 | | GR90 | 5 | 14 | 2 | 18 | 48 | GR90 | 20 | 5 PLOTS | 19 | 4 | 21 | 62 | 2.2 |
| 93 | LR484 | | GR91 | 9 | 17 | 2 | 13 | 49 | GR91 | 18 | 9 PLOTS | 27 | 4 | 12 | 69 | 8.1 |
| 93 | LR3705 | | GR92 | 5 | 30 | 4 | 4 | 69 | GR92 | 10 | 5 PLOTS | 47 | 7 | 7 | 108 | 4.4 |
| 93 | LR4271 | | GR92 | 10 | 21 | 3 | 5 | 50 | GR92 | 20 | 10 PLOTS | 32 | 5 | 9 | 78 | 5.8 |
| 93 | X3337*LR28 | | F5:6 | 3 | 9 | 1 | 19 | 38 | F6:7 | 10 | 3 PLOTS | 8 | 2 | 29 | 47 | 2.8 |
| 93 | (A3322*LR484)*A5843 | IP93-30875-9 | F2:3 | 1 | 9 | 9 | 0 | 27 | F3:4 | 3 | ST93-767 | 8 | 1 | 27 | 45 | 1.0 |
| 93 | (A3322*LR484)*A5843 | IP93-30877-57 | F2:3 | 1 | 8 | 0 | 30 | 47 | F3:4 | 5 | ST93-777 | 8 | 2 | 37 | 54 | 0.9 |
| 93 | (A3322*LR484)*A5843 | IP93-30875-39 | F2:3 | 1 | 8 | 9 | 26 | 39 | F3:4 | 4 | ST93-765 | 10 | 3 | 24 | 47 | 1.2 |
| 93 | (A3322*LR484)*A5843 | IP93-30878-50 | F2:3 | 1 | 7 | 0 | 29 | 44 | F3:4 | 4 | ST93-778 | 10 | 3 | 37 | 60 | 0.6 |
| 93 | (A3322*LR4&4)*A5843 | IP93-30875-75 | F2:3 | 1 | 9 | 1 | 0 | 20 | F3:4 | 4 | ST93-768 | 10 | 2 | 40 | 61 | 1.0 |
| 93 | (A3322*LR484)*A5843 | IP93-30875-3 | F2:3 | 1 | 2 | 11 | 25 | 39 | F3:4 | 7 | ST93-764 | 25 | 4 | 18 | 71 | 6.1 |
| 93 | (A3322*LR484)*A5843 | IP93-30875-2 | F2:3 | 1 | 2 | 11 | 21 | 35 | F3:4 | 3 | ST93-763 | 26 | 3 | 21 | 75 | 4.5 |
| 93 | A2396*(A3322*LR484) | IP93-38869-22 | F2:3 | 1 | 11 | 1 | 22 | 45 | F3:4 | 6 | ST93-381 | 24 | 5 | 11 | 64 | 2.7 |
| 93 | A2396*(A3322*LR484) | IP93-38869-14 | F2:3 | 1 | 8 | 2 | 29 | 46 | F3:4 | 4 | ST93-380 | 25 | 5 | 17 | 72 | 1.8 |
| 93 | A2396*(A3322*LR484) | IP93-38869-78 | F2:3 | 1 | 12 | 3 | 31 | 57 | F3:4 | 4 | ST93-386 | 26 | 7 | 9 | 68 | 3.2 |
| 93 | A2396*(A3322*LR484) | IP93-30869-23 | F2:3 | 1 | 15 | 2 | 28 | 60 | F3:4 | 10 | ST93-382 | 28 | 5 | 9 | 70 | 2.8 |
| 93 | A2396*(A3322*LR484) | IP93-30869-13 | F2:3 | 1 | 14 | 1 | 19 | 49 | F3:4 | 9 | ST93-379 | 28 | 6 | 10 | 73 | 4.5 |
| 93 | A2396*(A3322*LR484) | IP93-30869-39 | F2:3 | 1 | 7 | 0 | 29 | 44 | F3:4 | 4 | ST93-384 | 33 | 6 | 9 | 80 | 10.4 |
| 93 | A2396*(A3322*LR484) | IP93-30869-44 | F2:3 | 1 | 12 | 1 | 28 | 54 | F3:4 | 5 | ST93-385 | 55 | 11 | 5 | 126 | 15.4 |
| 93 | A2396(2)*LR484 | IP93-30870-4 | F2:3 | 1 | 17 | 3 | 21 | 57 | F3:4 | 3 | ST93-781 | 18 | 3 | 22 | 62 | 1.6 |
| 93 | A2396(2)*LR484 | IP93-30872-38 | F2:3 | 1 | 13 | 2 | 22 | 51 | F3:4 | 4 | ST93-2403 | 22 | 5 | 21 | 71 | 3.8 |
| 93 | A2396(2)*LR484 | IP93-30870-57 | F2:3 | 1 | 17 | 3 | 21 | 57 | F3:4 | 4 | ST93-790 | 23 | 6 | 24 | 76 | 2.8 |
| 93 | A3322(2)*LR484 | IP93-30870-6 | F2:3 | 1 | 16 | 3 | 24 | 59 | F3:4 | 4 | ST93-782 | 24 | 4 | 18 | 70 | 2.4 |
| 93 | A3322(2)*LR484 | IP93-30757-26 | F2:3 | 1 | 10 | 1 | 31 | 52 | F3:4 | 7 | 8T93-501 | 8 | 1 | 35 | 53 | 0.9 | low2 |
| 93 | A3322*LR3705 | IP93-30757-21 | F2:3 | 1 | 9 | 0 | 29 | 47 | F3:4 | 3 | ST93-499 | 8 | 2 | 38 | 57 | 1.6 | low2 |
| 93 | A3322*LR3705 | IP93-30757-12 | F2:3 | 1 | 10 | 2 | 25 | 47 | F3:4 | 3 | ST93-495 | 11 | 1 | 40 | 64 | 1.2 | low2 |
| 93 | A3322*LR4271 | IP93-30752-13 | F2:3 | 1 | 16 | 1 | 25 | 58 | F3:4 | 8 | ST93-526 | 14 | 2 | 7 | 38 | 1.7 | * |
| 93 | A3322*LR4271 | IP93-30753-1 | F2:3 | 1 | 18 | 2 | 22 | 59 | F3:4 | 7 | ST93-582 | 14 | 2 | 9 | 39 | 1.9 | * |

*= not signif. lower in stachyose than LR28 but lower in galactinol and total raffinose saccharides

TABLE 9

Evidence for Genetic Modfiers of stclx in Lines A1929 and LR33

| YEAR | PEDIGREE | SELECTION | GEN1 | N | STC | RAF | GAL | RSA | GEN2 | N | PLOT | STC | RAF | GAL | RSA | | SSDV |
|---|---|---|---|---|---|---|---|---|---|---|---|---|---|---|---|---|---|
| | | | | | IP92 Environment | | | | | | | ST92 Environment | | | | | |
| 92 | A1662 | | | | | | | | ELIT | 5 | ST92-31 | 75 | 12 | 1 | 164 | | 9.2 |
| 92 | A1923 | | | | | | | | ELIT | 5 | ST92-29 | 60 | 12 | 0 | 131 | | 3.6 |
| 92 | A1929 | | | | | | | | ELIT | 5 | ST92-30 | 65 | 11 | 0 | 141 | | 9.2 |
| 92 | A2396 | | | | | | | | ELIT | 10 | ST92-28 | 71 | 12 | 0 | 154 | | 7.9 |
| 92 | A2416 | | | | | | | | ELIT | 5 | ST92-148 | 62 | 11 | 2 | 137 | | 5.1 |
| 92 | A2506 | | | | | | | | ELIT | 5 | ST92-23 | 63 | 12 | 1 | 138 | | 2.9 |
| 92 | A2543 | | | | | | | | ELIT | 5 | ST92-25 | 71 | 11 | 0 | 152 | | 2.2 |
| 92 | A2835 | | | | | | | | ELIT | 5 | ST92-18 | 68 | 14 | 0 | 150 | | 2.2 |
| 92 | A2872 | | | | | | | | ELIT | 5 | ST92-20 | 76 | 13 | 0 | 164 | | 3.4 |
| 92 | A2943 | | | | | | | | ELIT | 5 | ST92-103 | 65 | 12 | 0 | 142 | | 4.7 |
| 92 | A3200 | | | | | | | | ELIT | 5 | ST92-16 | 73 | 16 | 0 | 163 | | 4.7 |
| 92 | A3205 | | | | | | | | ELIT | 5 | ST92-100 | 63 | 12 | 0 | 138 | | 9.2 |
| 92 | A3304 | | | | | | | | ELIT | 5 | ST92-12 | 77 | 16 | 0 | 170 | | 1.6 |
| 92 | A3322 | | | | | | | | ELIT | 10 | ST92-15 | 78 | 14 | 0 | 170 | | 2.8 |
| 92 | A3510 | | | | | | | | ELIT | 5 | ST92-11 | 76 | 15 | 0 | 168 | | 2.7 |
| 92 | A3733 | | | | | | | | ELIT | 5 | ST92-97 | 73 | 13 | 0 | 158 | | 6.7 |
| 92 | A3935 | | | | | | | | ELIT | 5 | ST92-10 | 63 | 10 | 0 | 136 | | 7.8 |
| 92 | A4341 | | | | | | | | ELIT | 5 | ST92-8 | 61 | 10 | 0 | 131 | | 3.6 |
| 92 | A4415 | | | | | | | | ELIT | 5 | ST92-7 | 56 | 8 | 2 | 121 | | 3.1 |
| 92 | A4595 | | | | | | | | ELIT | 5 | ST92-75 | 72 | 12 | 1 | 157 | | 2.7 |
| 92 | A4715 | | | | | | | | ELIT | 5 | ST92-6 | 68 | 8 | 0 | 145 | | 5.8 |
| 92 | A5403 | | | | | | | | ELIT | 4 | ST92-4 | 64 | 11 | 0 | 139 | | 1.0 |
| 92 | A5560 | | | | | | | | ELIT | 10 | ST92-4 | 68 | 8 | 0 | 144 | | 6.6 |
| 92 | BURLISON | | | | | | | | ELIT | 5 | ST92-19 | 72 | 13 | 0 | 157 | | 2.0 |
| 92 | DP415 | | | | | | | | ELIT | 4 | ST92-71 | 69 | 6 | 1 | 146 | | 5.0 |
| 92 | HUTCHESON | | | | | | | | ELIT | 14 | ST92-242 | 65 | 9 | 0 | 139 | | 10.5 |
| 92 | KASOTA | | | | | | | | ELIT | 5 | ST92-150 | 72 | 11 | 0 | 154 | | 4.7 |
| 92 | P9273 | | | | | | | | ELIT | 5 | ST92-22 | 77 | 14 | 0 | 168 | | 8.5 |
| 92 | P9303 | | | | | | | | ELIT | 5 | ST92-101 | 55 | 10 | 1 | 120 | | 2.5 |
| 92 | P9392 | | | | | | | | ELIT | 5 | ST92-9 | 75 | 15 | 0 | 166 | | 2.9 |
| 92 | LR28 | | GR90 | 5 | 16 | 2 | 27 | 59 | GR90 | 20 | 4 PLOTS | 24 | 3 | 27 | 77 | | 4.0 |
| 92 | LR484 | | GR91 | 5 | 22 | 3 | 13 | 61 | GR91 | 18 | 4 PLOTS | 32 | 4 | 16 | 84 | | 3.8 |
| 92 | (ST9025*LR28)*A1929 | IP92-33013-045 | F2:3 | 1 | 8 | 2 | 33 | 50 | F3:4 | 7 | ST92-360 | 8 | 1 | 45 | 62 | low2 | 0.8 |
| 92 | (ST9025*LR28)*A1929 | IP92-33013-038 | F2:3 | 1 | 15 | 3 | 29 | 64 | F3:4 | 5 | ST92-1851 | 9 | 2 | 33 | 54 | low2 | 1.3 |
| 92 | (ST9025*LR28)*A1929 | IP92-33013-044 | F2:3 | 1 | 8 | 1 | 18 | 36 | F3:4 | 8 | ST92-359 | 10 | 2 | 22 | 42 | low2 | 3.1 |
| 92 | (ST9025*LR28)*A1929 | IP92-33013-028 | F2:3 | 1 | 29 | 4 | 25 | 87 | F3:4 | 6 | ST92-1849 | 17 | 3 | 22 | 59 | low2 | 3.4 |
| 92 | LR33*LR28 | IP92-33082-106 | F2:3 | 1 | 11 | 3 | 10 | 34 | F3:4 | 6 | ST92-35 | 4 | 3 | 6 | 17 | * | 1.0 |
| 92 | LR33*LR28 | IP92-33382-110 | F2:3 | 1 | 21 | 4 | 14 | 59 | F3:4 | 5 | ST92-351 | 14 | 2 | 15 | 45 | | 5.8 |
| 92 | LR33*LR28 | IP92-33082-144 | F2:3 | 1 | 24 | 3 | 37 | 88 | F3:4 | 5 | ST92-354 | 21 | 4 | 31 | 77 | | 4.9 |
| 92 | LR33*LR28 | IP92-33082-092 | F2:3 | 1 | 23 | 4 | 13 | 62 | F3:4 | 5 | ST92-353 | 25 | 3 | 18 | 71 | | 6.0 |
| 92 | LR33*LR28 | IP92-33082-142 | F2:3 | 1 | 27 | 3 | 24 | 81 | F3:4 | 5 | ST92-350 | 27 | 3 | 28 | 84 | | 6.7 |
| | | | | | IP93 Environment | | | | | | | ST93 Environment | | | | | |
| 93 | A1923 | | ELIT | | | | | | ELIT | 8 | ST93-208 | 69 | 19 | 0 | 156 | | 3.4 |
| 93 | A1929 | | ELIT | | | | | | ELIT | 8 | ST93-204 | 75 | 17 | 0 | 167 | | 4.8 |

TABLE 9-continued

Evidence for Genetic Modfiers of stclx in Lines A1929 and LR33

| YEAR | PEDIGREE | SELECTION | GEN1 | N | STC | RAF | GAL | RSA | GEN2 | N | PLOT | STC | RAF | GAL | RSA | | SSDV |
|---|---|---|---|---|---|---|---|---|---|---|---|---|---|---|---|---|---|
| 93 | A2396 | | ELIT | | | | | | ELIT | 8 | ST93-212 | 76 | 19 | 0 | 171 | | 3.4 |
| 93 | A2835 | | ELIT | | | | | | ELIT | 8 | ST93-216 | 74 | 20 | 0 | 168 | | 5.7 |
| 93 | A2872 | | ELIT | | | | | | ELIT | 8 | ST93-220 | 80 | 19 | 0 | 180 | | 3.7 |
| 93 | A3322 | | ELIT | | | | | | ELIT | 8 | ST93-224 | 84 | 16 | 0 | 184 | | 2.0 |
| 93 | A4715 | | ELIT | | | | | | ELIT | 8 | ST93-232 | 78 | 12 | 0 | 167 | | 7.1 |
| 93 | WILLIAMS82 | | ELIT | | | | | | ELIT | 8 | ST93-228 | 72 | 13 | 0 | 156 | | 7.6 |
| 93 | LR28 | | GR90 | 5 | 14 | 2 | 18 | 48 | GR90 | 20 | 5 PLOTS | 19 | 4 | 21 | 62 | | 2.2 |
| 93 | LR484 | | GR91 | 9 | 17 | 2 | 13 | 49 | GR91 | 18 | 9 PLOTS | 27 | 4 | 12 | 69 | | 8.1 |
| 93 | LR3705 | | GR92 | 5 | 30 | 4 | 4 | 69 | GR92 | 10 | 5 PLOTS | 47 | 7 | 7 | 108 | | 4.4 |
| 93 | LR4271 | | GR92 | 10 | 21 | 3 | 5 | 50 | GR92 | 20 | 10 PLOTS | 32 | 5 | 9 | 78 | | 5.8 |
| 93 | X3337*LR28 | | F5:6 | 3 | 9 | 1 | 19 | 38 | F5:7 | 10 | 3 PLOTS | 8 | 2 | 29 | 47 | | 2.8 |
| 93 | (ST9025*LR28)*(2)A1929 | IP93-30589-6 | F2:3 | 1 | 5 | 1 | 16 | 21 | F3:4 | 4 | ST93-354 | 3 | 1 | 10 | 17 | low3 | 1.0 |
| 93 | (ST9025*LR28)*(2)A1929 | IP93-30859-20 | F2:3 | 1 | 5 | 1 | 18 | 30 | F3:4 | 4 | ST93-358 | 4 | 2 | 11 | 20 | low3 | 1.2 |
| 93 | (ST9025*LR28)*(2)A1929 | IP93-30859-17 | F2:3 | 1 | 6 | 1 | 21 | 33 | F3:4 | 4 | ST93-356 | 4 | 3 | 10 | 20 | low3 | 0.0 |
| 93 | (ST9025*LR28)*(2)A1929 | IP93-30859-27 | F2:3 | 1 | 6 | 1 | 22 | 35 | F3:4 | 4 | ST93-359 | 4 | 1 | 15 | 24 | low2 | 1.6 |
| 93 | (ST9025*LR28)*(2)A1929 | IP93-30860-7 | F2:3 | 1 | 3 | 0 | 21 | 28 | F3:4 | 4 | ST93-372 | 4 | 3 | 19 | 30 | low2 | 1.0 |
| 93 | (ST9025*LR28)*(2)A1929 | IP93-30859-5 | F2:3 | 1 | 4 | 1 | 14 | 23 | F3:4 | 4 | ST93-353 | 5 | 4 | 12 | 25 | low3 | 2.8 |
| 93 | (ST9025*LR28)*(2)A1929 | IP93-30860-32 | F2:3 | 1 | 5 | 2 | 17 | 29 | F3:4 | 4 | ST93-378 | 5 | 3 | 14 | 25 | low3 | 1.0 |
| 93 | (ST9025*LR28)*(2)A1929 | IP93-30859-43 | F2:3 | 1 | 6 | 2 | 17 | 31 | F3:4 | 4 | ST93-363 | 5 | 3 | 13 | 25 | low3 | 0.8 |
| 93 | (ST9025*LR28)*(2)A1929 | IP93-30860-23 | F2:3 | 1 | 2 | 0 | 17 | 20 | F3:4 | 4 | ST93-374 | 5 | 3 | 16 | 28 | low2 | 1.0 |
| 93 | (ST9025*LR28)*(2)A1929 | IP93-30860-6 | F2:3 | 1 | 3 | 1 | 18 | 24 | F3:4 | 3 | ST93-371 | 5 | 3 | 16 | 28 | low2 | 0.5 |
| 93 | (ST9025*LR28)*(2)A1929 | IP93-30859-35 | F2:3 | 1 | 6 | 1 | 18 | 31 | F3:4 | 4 | ST93-360 | 5 | 2 | 17 | 29 | low2 | 1.0 |
| 93 | (ST9025*LR28)*(2)A1929 | IP93-30859-42 | F2:3 | 1 | 6 | 1 | 21 | 33 | F3:4 | 4 | ST93-362 | 5 | 2 | 18 | 31 | low2 | 0.8 |
| 93 | (ST9025*LR28)*(2)A1929 | IP93-30860-5 | F2:3 | 1 | 3 | 1 | 28 | 34 | F3:4 | 4 | ST93-370 | 5 | 2 | 23 | 35 | low2 | 1.0 |
| 93 | (ST9025*LR28)*(2)A1929 | IP93-30859-57 | F2:3 | 1 | 5 | 1 | 17 | 29 | F3:4 | 3 | ST93-365 | 6 | 2 | 12 | 25 | low3 | 2.9 |
| 93 | (ST9025*LR28)*(2)A1929 | IP93-30860-30 | F2:3 | 1 | 4 | 1 | 17 | 26 | F3:4 | 4 | ST93-376 | 6 | 3 | 14 | 28 | low3 | 1.2 |
| 93 | (ST9025*LR28)*(2)A1929 | IP93-30859-60 | F2:3 | 1 | 5 | 1 | 17 | 28 | F3:4 | 4 | ST93-367 | 6 | 3 | 19 | 34 | low2 | 2.8 |
| 93 | (ST9025*LR28)*(2)A1929 | IP93-30860-12 | F2:3 | 1 | 3 | 1 | 22 | 28 | F3:4 | 4 | ST93-373 | 6 | 4 | 18 | 35 | low2 | 2.2 |
| 93 | (ST9025*LR28)*(2)A1929 | IP93-30859-1 | F2:3 | 1 | 6 | 1 | 15 | 29 | F3:4 | 4 | ST93-352 | 6 | 1 | 26 | 38 | low2 | 1.0 |
| 93 | (ST9025*LR28)*(2)A1929 | IP93-30860-31 | F2:3 | 1 | 4 | 1 | 23 | 33 | F3:4 | 4 | ST93-377 | 8 | 4 | 23 | 43 | low2 | 1.0 |
| 93 | LR33*LR28 | IP93-31019-2 | F4:5 | 1 | 12 | 7 | 1 | 32 | F5:6 | 2 | ST93-107 | 2 | 5 | 0 | 8 | low4 | 0.7 |
| 93 | LR33*LR28 | IP93-31060-2 | F4:5 | 1 | 4 | 1 | 0 | 8 | F5:6 | 4 | ST93-62 | 2 | 6 | 0 | 9 | low4 | 1.2 |
| 93 | LR33*LR28 | IP93-31019-6 | F4:5 | 1 | 4 | 5 | 0 | 14 | F5:6 | 2 | ST93-111 | 2 | 7 | 0 | 11 | low4 | 0.0 |
| 93 | LR33*LR28 | IP93-31059-3 | F4:5 | 1 | 5 | 5 | 0 | 15 | F5:8 | 2 | ST93-75 | 2 | 8 | 0 | 12 | low4 | 1.4 |
| 93 | LR33*LR28 | IP93-31059-2 | F4:5 | 1 | 6 | 3 | 0 | 15 | F5:6 | 4 | ST93-74 | 3 | 9 | 0 | 14 | low4 | 0.8 |
| 93 | LR33*LR28 | IP93-31059-1 | F4:5 | 1 | 5 | 4 | 0 | 15 | F5:6 | 3 | ST93-73 | 3 | 10 | 0 | 11 | low4 | 0.5 |
| 93 | LR33*LR28 | IP93-31060-1 | F4:5 | 1 | 3 | 2 | 0 | 8 | F5:6 | 4 | ST93-61 | 4 | 5 | 0 | 13 | low4 | 4.8 |
| 93 | LR33*LR28 | IP93-31019-1 | F4:5 | 1 | 8 | 5 | 1 | 22 | F5:6 | 2 | ST93-106 | 5 | 7 | 0 | 15 | low4 | 0.7 |
| 93 | LR33*LR28 | IP93-31019-5 | F4:5 | 1 | 2 | 1 | 0 | 5 | F5:6 | 2 | ST93-110 | 6 | 7 | 0 | 18 | low4 | 2.1 |
| 93 | LR33*LR28 | IP93-31019-4 | F4:5 | 1 | 9 | 5 | 1 | 24 | F5:6 | 2 | ST93-109 | 6 | 8 | 0 | 19 | low4 | 3.5 |
| 93 | LR33*LR28 | IP93-31019-3 | F4:5 | 1 | 10 | 4 | 1 | 25 | F5:6 | 2 | ST93-108 | 8 | 8 | 0 | 23 | low4 | 7.8 |
| 93 | LR33*LR28 | IP93-31059-4 | F4:5 | 1 | 6 | 4 | 0 | 15 | F5:6 | 2 | ST93-76 | 24 | 9 | 0 | 56 | | 32.5 |
| 93 | A1923*(LR33*LR28) | IP93-30836-16 | F2:3 | 1 | 0 | 0 | 0 | 1 | F3:4 | 3 | ST93-244 | 0 | 2 | 0 | 2 | low4 | 0.0 |
| 93 | A1923*(LR33*LR28) | IP93-30836-11 | F2:3 | 1 | 2 | 3 | 0 | 6 | F3:4 | 5 | ST93-243 | 0 | 5 | 0 | 5 | low4 | 0.4 |
| 93 | A1923*(LR33*LR28) | IP93-30831-26 | F2:3 | 1 | 4 | 3 | 0 | 10 | F3:4 | 4 | ST93-291 | 0 | 4 | 0 | 5 | low4 | 0.6 |
| 93 | A1923*(LR33*LR28) | IP93-30824-11 | F2:3 | 1 | 4 | 2 | 0 | 10 | F3:4 | 3 | ST93-212 | 0 | 4 | 0 | 5 | low4 | 0.5 |
| 93 | A1923*(LR33*LR28) | IP93-30835-15 | F2:3 | 1 | 2 | 2 | 0 | 5 | F3:4 | 4 | ST93-241 | 1 | 4 | 0 | 5 | low4 | 0.0 |
| 93 | A1923*(LR33*LR28) | IP93-30826-36 | F2:3 | 1 | 4 | 1 | 0 | 9 | F3:4 | 4 | ST93-277 | 1 | 3 | 0 | 5 | low4 | 0.8 |

TABLE 9-continued

Evidence for Genetic Modifers of stclx in Lines A1929 and LR33

| YEAR | PEDIGREE | SELECTION | GEN1 | N | STC | RAF | GAL | RSA | GEN2 | N | PLOT | STC | RAF | GAL | RSA | RSA | SSDV |
|---|---|---|---|---|---|---|---|---|---|---|---|---|---|---|---|---|---|
| 93 | A1923*(LR33*LR28) | IP93-30825-24 | F2:3 | 1 | 3 | 3 | 0 | 10 | F3:4 | 3 | ST93-276 | 2 | 7 | 0 | 10 | low4 | 0.5 |
| 93 | A1923*(LR33*LR28) | IP93-30836-5 | F2:3 | 1 | 1 | 3 | 0 | 6 | F3:4 | 5 | ST93-242 | 2 | 5 | 3 | 11 | low4 | 2.0 |
| 93 | A1923*(LR33*LR28) | IP93-30834-6 | F2:3 | 1 | 2 | 3 | 0 | 6 | F3:4 | 4 | ST93-240 | 3 | 7 | 0 | 11 | low4 | 1.8 |
| 93 | A1923*(LR33*LR28) | IP93-30831-23 | F2:3 | 1 | 3 | 3 | 0 | 8 | F3:4 | 3 | ST93-289 | 4 | 6 | 0 | 15 | low4 | 3.8 |
| 93 | A1923*(LR33*LR28) | IP93-30829-23 | F2:3 | 1 | 2 | 1 | 0 | 5 | F3:4 | 4 | ST93-285 | 6 | 6 | 0 | 17 | low4 | 1.2 |
| 93 | A1923*(LR33*LR28) | IP93-30829-9 | F2:3 | 1 | 3 | 4 | 2 | 11 | F3:4 | 4 | ST93-284 | 7 | 10 | 1 | 25 | low4 | 2.2 |
| 93 | A1923*(LR33*LR28) | IP93-30829-28 | F2:3 | 1 | 5 | 1 | 2 | 13 | F3:4 | 6 | ST93-286 | 17 | 7 | 8 | 48 | low4 | 11.5 |
| 93 | A1923*(LR33*LR28) | IP93-30719-27 | F2:3 | 1 | 8 | 1 | 6 | 23 | F3:4 | 4 | ST93-278 | 21 | 5 | 11 | 56 |  | 5.0 |
| 93 | A2396*(LR33*LR28) | IP93-30839-36 | F2:3 | 1 | 3 | 1 | 0 | 8 | F3:4 | 3 | ST93-400 | 0 | 1 | 0 | 1 | low4 | 0.0 |
| 93 | A2396*(LR33*LR28) | IP93-30839-31 | F2:3 | 1 | 0 | 2 | 0 | 3 | F3:4 | 4 | ST93-398 | 1 | 4 | 0 | 5 | low4 | 0.8 |
| 93 | A2396*(LR33*LR28) | IP93-30839-38 | F2:3 | 1 | 3 | 2 | 0 | 9 | F3:4 | 3 | ST93-401 | 2 | 4 | 0 | 7 | low4 | 2.1 |
| 93 | A2396*(LR33*LR28) | IP93-30839-6 | F2:3 | 1 | 1 | 4 | 0 | 6 | F3:4 | 4 | ST93-395 | 3 | 10 | 0 | 16 | low4 | 1.4 |
| 93 | A2396*(LR33*LR28) | IP93-30837-50 | F2:3 | 1 | 14 | 5 | 6 | 32 | F3:4 | 3 | ST93-393 | 4 | 6 | 0 | 15 | low4 | 2.2 |
| 93 | A2396*(LR33*LR28) | IP93-30721-4 | F2:3 | 1 | 4 | 0 | 0 | 9 | F3:4 | 3 | ST93-392 | 11 | 4 | 17 | 43 | low2 | 2.6 |
| 93 | A2396*(LR33*LR28) | IP93-30720-20 | F2:3 | 1 | 0 | 1 | 0 | 7 | F3:4 | 4 | ST93-390 | 16 | 6 | 3 | 40 |  | 22.2 |
| 93 | A2872*(LR33*LR28) | IP93-30725-3 | F2:3 | 1 | 4 | 2 | 0 | 9 | F3:4 | 4 | ST93-254 | 0 | 3 | 0 | 3 | low4 | 0.0 |
| 93 | A2872*(LR33*LR28) | IP93-30845-39 | F2:3 | 1 | 1 | 2 | 0 | 4 | F3:4 | 3 | S193-248 | 1 | 4 | 0 | 4 | low4 | 0.6 |
| 93 | A2872*(LR33*LR28) | IP93-30846-48 | F2:3 | 1 | 2 | 1 | 0 | 5 | F3:4 | 4 | ST93-251 | 0 | 2 | 0 | 4 | low4 | 1.6 |
| 93 | A2872*(LR33*LR28) | IP93-30845-22 | F2:3 | 1 | 3 | 2 | 0 | 6 | F3:4 | 3 | ST93-246 | 1 | 4 | 0 | 6 | low4 | 0.5 |
| 93 | A2872*(LR33*LR28) | IP93-30857-30 | F2:3 | 1 | 3 | 5 | 0 | 11 | F3:4 | 6 | ST93-267 | 1 | 6 | 0 | 8 | low4 | 0.7 |
| 93 | A2872*(LR33*LR28) | IP93-30850-48 | F2:3 | 1 | 4 | 4 | 0 | 12 | F3:4 | 4 | ST93-259 | 1 | 6 | 0 | 8 | low4 | 0.6 |
| 93 | A2872*(LR33*LR28) | IP93-30725-10 | F2:3 | 1 | 3 | 3 | 0 | 9 | F3:4 | 4 | ST93-255 | 2 | 5 | 0 | 9 | low4 | 0.0 |
| 93 | A2872*(LR33*LR28) | IP93-30845-36 | F2:3 | 1 | 3 | 3 | 2 | 11 | F3:4 | 4 | ST93-257 | 2 | 8 | 0 | 12 | low4 | 2.0 |
| 93 | A2872*(LR33*LR28) | IP93-30858-40 | F2:3 | 1 | 0 | 0 | 0 | 0 | F3:4 | 4 | ST93-247 | 3 | 2 | 15 | 24 | low2 | 0.6 |
| 93 | A2872*(LR33*LR28) | IP93-30723-5 | F2:3 | 1 | 2 | 4 | 5 | 13 | F3:4 | 8 | ST93-271 | 16 | 6 | 3 | 40 |  | 13.3 |
| 93 | A3322*(LR33*LR28) | IP93-30724-2 | F2:3 | 1 | 0 | 3 | 0 | 4 | F3:4 | 4 | ST93-295 | 0 | 4 | 0 | 5 | low4 | 0.6 |
| 93 | A3322*(LR33*LR28) | IP93-30723-8 | F2:3 | 1 | 2 | 1 | 0 | 4 | F3:4 | 3 | ST93-306 | 2 | 2 | 0 | 6 | low4 | 1.0 |
| 93 | A3322*(LR33*LR28) | IP93-30843-41 | F2:3 | 1 | 5 | 2 | 0 | 11 | F3:4 | 4 | ST93-296 | 2 | 5 | 0 | 9 | low4 | 3.8 |
| 93 | A3322*(LR33*LR28) | IP93-30842-27 | F2:3 | 1 | 2 | 4 | 0 | 8 | F3:4 | 4 | ST93-311 | 4 | 5 | 0 | 12 | low4 | 3.6 |
| 93 | A3322*(LR33*LR28) | IP93-30844-36 | F2:3 | 1 | 3 | 2 | 1 | 10 | F3:4 | 3 | ST93-309 | 8 | 8 | 0 | 23 | low4 | 1.2 |
| 93 | A3322*(LR33*LR28) | IP93-30844-36 | F2:3 | 1 | 3 | 2 | 2 | 9 | F3:4 | 3 | ST93-312 | 61 | 16 | 0 | 139 |  | 42.8 |

*= appropriate controls were not available in ST92 environment to test significance of low4 phenotype The majority of the low4 selections from the IP93 environment confirmed their low4 phenotype when grown out in replicate in the ST93 environment. Since the low4 phenotype is characterized as having a stachyose content significantly less than an unmodified stc1x line (LR28) and a galactinol content significantly less than that of low3 types, two separate statistical tests were needed to confirm the statistical significance of the low4 phenotype. The first test was comparing the stachyose content to that of LR28 as previously explained. Lines with mean seed stachyose content of less than 13 $\mu$mol/g passed the fast test. The second test was comparing the galactinol content to that of low3 types. This was done by obtaining an average and standard deviation for galactinol content of lines of pedigree (ST9025*LR28)*(2)A1929 previously identified as low3 above. In the ST93 environment, low3 lines of pedigree (ST9025*LR28)*(2)A1929 (designation "low3" in Table 9) had a mean galactinol content of 12±2.8 $\mu$mol/g. Therefore, lines with a galatinol content three or more standard deviations below this mean (i.e. less than 4 $\mu$mol/g galactinol) passed the second test. Low4 lines passing both statistical tests (mean seed stachyose less than 13 $\mu$mol/g and mean seed galactinol less than 4 $\mu$mol/g) are identified with as "low4" in Table 9.

Low4 selections from the (LR33*LR28)*elite pedigrees were as low in raffinose saccharide content as the original low4 selections from the LR33*LR28 pedigree. This proves that the low4 phenotype can be easily maintained in subsequent backcrosses. Low4 selections from the pedigrees LR33*LR28, A1923*(LR33*LR28), A2396*(LR33*LR28), A2872*(LR33*LR28), and A3322*(LR33*LR28) were typically less than 10 $\mu$mol/g in stachyose, less than 10 umol/g in raffinose, and had little or no galactinol. The low4 phenotype was observed from all pedigrees involving LR33*LR28 regardless of which elite line was used in the subsequent backcross. Since the LR33*LR28 cross alone yielded low4 types, the low4 modification of the stc1x gene is clearly coming from LR33 and does not require modifiers from the elite lines. ST92, IP93, and ST93 data provide conclusive evidence that LR33 contains modifier(s) that reduce both the stachyose and galactinol content of stc1x lines. This resulted in a total seed raffinose saccharide content that was typically less than 20 $\mu$mol/g and more commonly in the 5 to 15 $\mu$mol/g range. Since conventional elite lines grown in the same commercial environment had an average seed total raffinose saccharide content of 169 $\mu$mol/g, the disclosed low4 phenotype resulted in a 90 to 97% reduction in seed raffinose saccharide content.

Example 4

Utilization of Genetic Variation for the Production of Improved Soy Protein Products Preparation of Soy Products: Full-Fat Flakes, Defatted White Flakes, and Desolventized, Toasted Meals Soybean meals were prepared from 5 elite and 11 stc1x lines under laboratory or pilot plant conditions from field grown samples that ranged from ca. 5 to 500 pounds. The processing conditions employed were designed to mimic closely those used by commercial manufacturers of deffated flakes and desolventized, toasted soybean meals [see JACOS (1981) Vol 58, Number 3]. Different processing equipment was used, depending on the quantities of seed available. Commercial conditions can not be mimicked exactly due to inherent differences in the equipment used in a laboratory setting compared to those found in a commercial facility. Nevertheless, the conditions employed, if not the exact equipment, approximate those used commercially.

For small batched of grain (less than 10 pounds) soybeans were tempered to between 8 and 10% moisture at 54° C. and then cracked in a 10"·12" cracking roller mill (Ferrell-Ross, Oklahoma City, Okla., U.S.A.). Rolls were 10" in diameter and 12" wide and had 8 and 10 grooves/inch (sawtooth), turning at about 700 and 1100 rpm (revolutions per minute), respectively. The gap between the rolls was set to be about 0.05". Hulls were removed by air aspiration using a 'Carter Dockage Tester' (Simon-Day, Winnipeg, Manitoba). Samples were passed through twice to insure hull removal. Alternatively, hulls were removed with a Kice multi-pass aspirator (Kice Industries, Wichita, Kan., U.S.A.). The dehulled meats were flaked using 18"·18" flaking rolls (E. R. and F. Turner Ltd.), turning at 290 and 285 rpm respectively, and set with a gap of 0.003" (minimum). Full-fat flakes were extracted for 6 h in a soxhlet extractor (12 or 20 L, depending on sample size). Following extraction, the defatted meals were air desolventized for a minimum of 48 h at room temperature in a fume hood. Following desolventization, the moisture content of the defatted meals were determined gravimetrically [AOCS Method Ba 2a-38], water was added to bring the sample to 10% moisture content, and the resultant sample was mixed in a 6 L Waring blender. Following mixing, the samples was transferred to a sealed plastic bucket and allowed to equilibrate overnight. Defatted meals were then toasted to have a KOH nitrogen solubility within the range of 75±10% [Araba and Dale (1990) Poultry Science 69:76–83] using a combination of heating in a 650 watt microwave oven with a 4000v DC magnetron (2450 MHz) and a convection oven set to 115° C. The residence time in the microwave oven was typically 4.5 min and 45 min in the convection oven, but some samples were heated for longer periods of time to insure similar KOH nitrogen solubility among samples.

Alternatively, defatted flakes were prepared by passing 49° C. hexane over a bed of flakes within a stainless steel vessel using a solvent:flake ratio of 6:1. Six cycles of extraction were used to reduce the oil content to less than the standard specification of 0.5%. Following extraction, the flakes were allowed to desolventize overnight at room temperature in a fume hood. Following desolventization, moisture was added at a ratio of 160 mL/kg flakes. The flakes were mixed during the addition of water to insure uniform hydration and were then tempered for 5 min at 27° C. The tempered flakes were toasted at 149° C. for 45 min in a heated jacket nut roaster. Following the roasting period, the vessel was opened for 5 min to allow any excess moisture that may have accumulated during the toasting to escape. At this stage the desolventized, toasted meals were ready for use in animal feeding studies.

Nitrogen-Corrected, True Metabolizable Energy Assays

Depending on the particle size distribution toasted meals were fed directly or as 1:1 mixtures with ground corn in order to facilitate administration of the materials to the test birds. The mixtures were assayed for Nitrogen-corrected, True Metabolizable Energy content (TME$_N$) using a modification of the protocol described previously [Dale and Fuller (1987) Special Report No. 319, University of Georgia College of Agriculture, Cooperative Extension Service]. In the case of samples fed as 1:1 mixtures with ground corn, the ground corn alone was also precision fed in order to correct for the metabolizable energy of this portion of the mixture. Single comb, white leghorn cockerels, placed in individual cages with raised wire floors were fasted for 24 h prior to the initiation of the study. Test material was administered directly into the crop and excreta were quantitatively collected for 48 h into plastic trays placed under each cage.

Depending on the amount of material available for testing, nine or ten birds were used for each test material and a separate group were fasted throughout the study to correct for endogenous losses. Water was provided ad libitum throughout the study. Following the collection period, the excreta were dried in a forced air oven at 65° C. and the energy content of the excreta, as well as the defatted meals was determined by bomb calorimetry. Moisture content of the excreta and the defatted meals was determined using AOCS Method Ba 2a-38. Gross energy content of the excreta and defatted meals were determined using a Parr bomb calorimeter. Gross energy content and $TME_N$ of the defatted meals were expressed on a dry matter basis to normalize small differences in moisture seen among samples. The efficiency of utilization of gross energy content was determined from the quotient of $TME_N$ and gross energy. The results obtained from the animal feeding studies were subjected to analysis of variance.

Defatted meals from stc1x lines were found to have significantly higher (ca 12%) $TME_N$ and Gross Energy Utilization than meals produced from conventional cultivars (Table 10). These results clearly indicate the utility of lines containing stc1x compared to soybeans that are currently being used in commerce.

TABLE 10

Raffinose Saccharide Content, $TME_N$, Gross Energy, and Gross Energy Utilization Efficiency of Defatted Soybean Meals Prepared from Conventional and stc1x Lines

| Genotype | Number of Lines | STC μmol/g | RSA μmol/g | $TME_N$ | Gross Energy kcal/kg | Gross Energy kcal/kg | $TME_N$ |
|---|---|---|---|---|---|---|---|
| Conventional | 5 | 126 | 274 | 2688 | 4813 | 0.56 | |
| stc1x | 11 | 20** | 76** | 3007** | 4813 | 0.63** | |

**Indicates that stc1x mean is significantly different than control mean at p < 0.01

Preparation of a Pet Food with Improved Carbohydrate Composition

Preparation of Desolventized, Toasted Soybean Meals

For preparation of larger quantities of material, about 450 to 500 pounds each of two samples (one a conventional variety and the second a blend of stc1a lines) were tempered to between 8 and 10% moisture at 85° C. in a Model 103 Belt-O-Matic Drier (BNW Industries, Mentone, Ind., U.S.A.) and then cracked in a 10"·12" cracking roller mill (Ferrell-Ross, Oklahoma City, Okla., U.S.A.). Rolls were 10" in diameter and 12" wide and had 10 and 6 grooves/inch, turning at 587 and 417 rpm, respectively. The gap between the rolls was set to 0.022". Hulls were removed by air aspiration using a Kice multi-pass aspirator (Kice Industries, Wichita, Kan., U.S.A.). The dehulled meats were heated in a 22" diamete·16" deep, bottom agitated French Cooker (French Oil Mill Machinery, Piqua, Ohio, U.S.A.) for about 35 min using a steam jacket. The meats were agitated by a stirring arm during this step in the process. The final temperature of the meats was about 54° C. Following heating, the meats were flaked using 12"·12" flaking rolls (Ferrell-Ross, Oklahoma City, Okla., U.S.A.), turning at 300 and 450 rpm respectively, and set with a gap of 0.012". Full-fat flakes were extracted in a Crown Model 4 Extractor (Crown Iron Works, Minneapolis, Minn., U.S.A.) using a solvent ratio of about 1.5 to 1 and a temperature of about 52° C. Following extraction, the defatted meals were desolventized in a Crown Desolventizer Toaster between 210° F. and 220° F. to obtain optimum toasting of the desolventized meal.

Following preparation of the desolventized, toasted meals, samples of the meals were analyzed for raffinose saccharide content using the HPLC method described in Example 1. The results of this analysis are presented in Table 11.

TABLE 11

Raffinose Saccharide Content of Unprocessed Soybeans and Desolventized, Toasted Meals Processed from a Conventional Soybean Variety and stc1a Lines

| Sample | RAF | STC | RSA |
|---|---|---|---|
| Whole Soybean: | | | |
| Conventional | 22 | 126 | 274 |
| stc1a | 3 | 19 | 80 |
| Soybean Meal: | | | |
| Conventional | 36 | 199 | 435 |
| stc1a | 5 | 26 | 107 |

Preparation of Pet Foods with Improved Stachyose Content

Following preparation of the desolventized, toasted soybean meals, rations were formulated to prepare extruded dry, expanded foods under conditions similar to those commonly used in commercial operations. Soybean meal is a common ingredient used by many dry, expanded food manufacturers and the inclusion rate of soybean meal can vary depending on the desires of the manufacturer. As a result, extruded dry, expanded foods were prepared with two levels of inclusion of soybean meal in order to produce rations which cover the range of soybean meal inclusion percentage that is commonly observed in commercial products. The product formulas used for preparation of the pet foods are shown in Table 12.

TABLE 12

Ingredient Formulas Used in the Preparation of Pet Foods with Decreased Stachyose Content

| | Diet | | | |
|---|---|---|---|---|
| | 1 | 2 | 3 | 4 |
| Ingredient | % Inclusion | | | |
| Corn | 63.53 | 63.53 | 48.34 | 48.34 |
| Conventional Soybean Meal | 0.00 | 25.97 | 0.00 | 40.96 |
| stc1a Soybean Meal | 25.97 | 0.00 | 40.96 | 0.00 |
| Meat Meal | 6.59 | 6.59 | 6.59 | 6.59 |
| DiCal (38% Ca) | 1.76 | 1.76 | 1.50 | 1.50 |
| Calcium Carbonate | 0.36 | 0.36 | 0.36 | 0.36 |
| Salt | 0.55 | 0.55 | 0.55 | 0.55 |
| Animal Fat | 0.80 | 0.80 | 1.30 | 1.30 |
| Vitamin Premix | 0.22 | 0.22 | 0.22 | 0.22 |
| Mineral Premix | 0.11 | 0.11 | 0.11 | 0.11 |
| Choline-Cl, 60% | 0.11 | 0.11 | 0.07 | 0.07 |
| Total | 100.00 | 100.00 | 100.00 | 100.00 |

The pet foods were prepared using conditions similar to those employed in commercial operations [Rokey (1983) Feed Manufacturing Technology III, 222–237; McCulloch, (1984) U.S. Pat. No. 4,454,804] using a Wenger Model TX-52 single-screw extruder using a die with a 5/32" diameter orifice (Wenger Manufacturing, INC, Sabetha, Kan., U.S.A.). In order to establish optimum conditions during the extrusion process, an initial run was performed using the formula employed in Diet 1 above, with the exception that a conventional soyflour was used in place of the desolventized, toasted soybean meal. Corn was ground using a Fitzmill Model D (Fitzpatrick CO, Cincinnati, Ohio, U.S.A.) at 4536 rpm with a screen (3.2 mm openings) and then blended with the remaining ingredients for 5 min. The final mix was then ground in the Fitzmill using a 20 mesh screen. The conditions used during the extrusion and drying process for the 4 diets are indicated in Table 13.

TABLE 13

Conditions Used During Extrusion and Drying in the
Manufacture Pet Foods from Conventional and stc1x Lines

| | Diet | | | |
|---|---|---|---|---|
| | 1 | 2 | 3 | 4 |
| Raw Material Information | | | | |
| Raw Material Moisture, mcwb | 9.60 | 9.66 | 7.58 | 9.42 |
| Raw Material Rate, pph | 210 | 210 | 210 | 210 |
| Feed Screw Speed, rpm | 20 | 20 | 20 | 20 |
| Preconditioning Information | | | | |
| Mixing Cylinder Speed, rpm | 165 | 165 | 165 | 165 |
| Steam to Mixing Cylinder, ppm | 0.16 | 0.16 | 0.16 | 0.16 |
| Water to Mixing Cylinder, ppm | 0.27 | 0.27 | 0.27 | 0.27 |
| Mixing Cylinder Temp. ° F. | 170 | 170 | 170 | 170 |
| Moisture Entering Extruder, mcwb | 18.47 | 19.87 | 19.32 | 19.26 |
| Extrusion Information | | | | |
| Shaft Speed, rpm | 385 | 385 | 385 | 385 |
| Motor Load, % | 18 | 17 | 19 | 18 |
| Steam Flow to Extruder, ppm | 0.13 | 0.13 | 0.13 | 0.13 |

Using the formulas and processing conditions described above, the four pet foods were prepared. Meals prepared from the stc1a line and the conventional variety were observed to be completely compatible with the equipment used in the preparation of the dry, expanded food. Following preparation of the dry, expanded foods, samples were analyzed for their raffinose saccharide content using the HPLC method described in Example 1. In addition, several commercially available dry, expanded dog foods were analyzed for their raffinose saccharide content for use in comparison to the pet foods prepared in the instant invention. The composition of the pet foods are shown in Table 14. The results indicated that even when used at soybean meal inclusion rates of ca. 41%, pet foods prepared from soybean meal from stc1a lines contained substantially less raffinose, stachyose and total raffinose saccharides than those from the conventional variety and the commercial pet foods. Meals, flours and grits prepared from soybean have application in a broad number of pet food products including, but not limited to dry, semi-moist and canned foods. For example, these soy protein products are also used in the manufacture of snack foods for pets. The soy protein products derived from stc1x lines described in the present invention should have broad applicability in all of the pet products that currently utilize soy protein products from conventional soybeans.

TABLE 14

Raffinose Saccharide Content of Pet Foods
Produced from Soybean Meal Processed from stc1a Lines

| Pet Food | RAF | STC | RSA |
|---|---|---|---|
| Diet 1 (stc1a) | 3 | 6 | 25 |
| Diet 3 (stc1a) | 3 | 10 | 38 |
| Diet 2 Conventional | 6 | 24 | 57 |
| Diet 4 (Conventional) | 9 | 39 | 88 |

TABLE 14-continued

Raffinose Saccharide Content of Pet Foods
Produced from Soybean Meal Processed from stc1a Lines

| Pet Food | RAF | STC | RSA |
|---|---|---|---|
| Purina Dog Chow | 6 | 16 | 38 |
| Dealer's Choice | 18 | 18 | 47 |
| Kibbles & Bits | 21 | 21 | 52 |

Preparation of Edible Soy Products with Improved Carbohydrate Composition

In order to determine the commercial utility of soy protein products produced from stc1x lines, an assortment of commercially available soy protein products (soy flours, soy concentrates, etc.) were purchased from local retail sources, air dried (or lyophilized if the commercial product contained a high water content) and analyzed for raffinose saccharide content. The precise details for the manufacture of these products is confidential and therefore unknown to Inventors. However, it is known that many of these commercial products have been processed, in part, specifically to reduce the raffinose saccharide content of the conventional soybean component used.

Defatted soy flakes were prepared from about 3 pound samples of stc1a lines using the same processing conditions used for small batches as described above. The resultant white flakes were then analyzed for raffinose saccharide content using the HPLC method described in Example 1. The results are presented in Table 15.

TABLE 15

Raffinose Saccharide Content of White Flakes
Prepared From stc1a Lines

| Sample | RAF | STC | RSA |
|---|---|---|---|
| Whole Soybean: | | | |
| AI9181 (stc1a) | 2 | 12 | 63 |
| ST9181 (stc1a) | 2 | 13 | 65 |
| ST911458 (stc1a) | 2 | 12 | 64 |
| D92-08 (conventional) | 14 | 71 | 162 |
| D92-10 (conventional) | 17 | 93 | 204 |
| White Flakes: | | | |
| AI9181 (stc1a) | 3 | 15 | 87 |
| ST9181 (stc1a) | 4 | 20 | 102 |
| ST911458 (stc1a) | 2 | 13 | 67 |
| D92-08 (Conventional) | 20 | 106 | 233 |
| D92-10 (Conventional) | 18 | 87 | 193 |
| Commercial Soy Protein Products: | | | |
| Central Soya, Ft. Wayne, IN, USA | | | |
| SoyaFluff (flour) | 33 | 132 | 297 |
| Centex (textured flour) | 32 | 125 | 282 |
| Promocaf (concentrate) | 7 | 50 | 106 |
| Response (textured conc.) | 5 | 35 | 75 |
| Solnuts, Inc., Hudson, IA, USA | | | |
| Halves | 13 | 48 | 108 |
| Soyflour (Full-Fat) | 16 | 47 | 110 |
| Diced | 17 | 61 | 138 |

As was seen previously with preparation of desolventized, toasted meals, white flakes prepared from stc1a lines displayed a substantially improved raffinose saccharide content compared to those prepared from conventional lines. These results indicate that white flakes produced from stc1x lines should have broad commercial applicability for a wide variety of soy protein products currently produced using white flakes as a starting material. These include, but are not limited to, flours and concentrates. This is supported by the observation in the present invention that white flakes produced from stc1a lines displayed a superior raffinose saccharide content to several commercially available soyflours (both full-fat and textured) and soy protein concentrates. The white flakes from stc1a lines were even found to have a lower raffinose saccharide content than that seen in even more highly processed soy protein concentrates made from conventional soybeans.

What is claimed is:

1. A soy protein product obtained from the processing of soybean seeds of a soybean plant homozygous for at least one gene that confers a heritable phenotype a seed stachyose content of less than 35 µmol/g, provided that the soybean plant is not a member of the line LR28 wherein such product is undenatured and defatted.

2. The soy protein product of claim 1 wherein such product is desolventized and toasted and has a true metabolizable energy content of greater than 2850 Kcal/kg.

3. The soy protein product of claim 1 wherein such product is heat processed, defatted and flash-desolventized.

4. The soy protein product of claim 1 wherein such product is heat processed, and defatted.

5. The heat-processed, defatted soy protein product of claim 4 wherein the soy product has a Nitrogen Solubility Index of greater than 60 and less than or equal to 95.

6. The heat-processed, defatted soy protein product of claim 4 wherein the soy product has a Nitrogen Solubility Index of from 20 to 60.

7. The heat-processed, defatted soy protein product of claim 4 wherein the soy product has a Nitrogen Solubility Index of less than 20.

* * * * *